United States Patent
Ashraf

(10) Patent No.: US 10,443,044 B2
(45) Date of Patent: Oct. 15, 2019

(54) GENERATING CARDIAC PROGENITOR CELLS FROM PLURIPOTENT STEM CELLS USING ISOXAZOLE OR ISOXAZOLE LIKE COMPOUNDS

(71) Applicant: Muhammad Ashraf, Cincinnati, OH (US)

(72) Inventor: Muhammad Ashraf, Cincinnati, OH (US)

(73) Assignee: IPS Heart, Houston, TX (US)

( * ) Notice: Subject to any disclaimer, the term of this patent is extended or adjusted under 35 U.S.C. 154(b) by 330 days.

(21) Appl. No.: 15/201,292

(22) Filed: Jul. 1, 2016

(65) Prior Publication Data

US 2017/0002329 A1    Jan. 5, 2017

Related U.S. Application Data

(63) Continuation-in-part of application No. 14/951,354, filed on Nov. 24, 2015, and a continuation-in-part of application No. 14/255,789, filed on Apr. 17, 2014, now abandoned.

(51) Int. Cl.
| | |
|---|---|
| *C12N 5/074* | (2010.01) |
| *C12N 5/077* | (2010.01) |
| *A61K 31/42* | (2006.01) |
| *A61K 35/545* | (2015.01) |

(52) U.S. Cl.
CPC ............ *C12N 5/0696* (2013.01); *A61K 31/42* (2013.01); *A61K 35/545* (2013.01); *C12N 5/0657* (2013.01); *C12N 2501/999* (2013.01); *C12N 2506/45* (2013.01)

(58) Field of Classification Search
CPC ............................ C12N 5/0696; C12N 5/0657; C12N 2501/72; C12N 2501/999; C12N 2506/45; A61K 31/42; A61K 35/28; A61K 35/34; A61K 35/545; A61K 45/06; A61L 27/3804; A61L 27/3873
See application file for complete search history.

(56) References Cited

U.S. PATENT DOCUMENTS

| | | | |
|---|---|---|---|
| 5,059,614 | A | 10/1991 | Lepage et al. |
| 6,638,369 | B1 | 10/2003 | Tucker et al. |
| 8,318,951 | B2 | 11/2012 | Olson et al. |
| 9,078,919 | B2 | 7/2015 | Olson et al. |
| 9,163,235 | B2 | 10/2015 | Van Rooij et al. |
| 2004/0072345 | A1 | 4/2004 | Altaba et al. |
| 2010/0041054 | A1 | 2/2010 | Mack |
| 2010/0184051 | A1 | 7/2010 | Hochedlinger et al. |
| 2011/0201110 | A1 | 8/2011 | Tezuka et al. |
| 2012/0197189 | A1 | 8/2012 | Guldner et al. |
| 2012/0301438 | A1 | 11/2012 | Cheng |
| 2013/0035374 | A1 | 2/2013 | Morrisey |
| 2013/0178506 | A1 | 7/2013 | Dioum et al. |
| 2013/0189781 | A1 | 7/2013 | Goodell et al. |
| 2014/0005251 | A1 | 1/2014 | Weijzen et al. |
| 2015/0297638 | A1 | 10/2015 | Ashraf |
| 2016/0032289 | A1 | 2/2016 | Hardee et al. |
| 2016/0076001 | A1 | 3/2016 | Ashraf |

FOREIGN PATENT DOCUMENTS

| | | |
|---|---|---|
| WO | WO-99/02507 | 1/1999 |
| WO | WO-2013/024410 A1 | 2/2013 |
| WO | WO-2015/160982 | 10/2015 |

OTHER PUBLICATIONS

Zhu et al., Bioorganic & Med. Chem., 26: 3065-3075, 2018.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Shiraki et al, Genes to Cells, 13:731-746, 2008.*
Wobus et al. (1997) J MoL Cell Cardiology 29:1525.*
Xu et al. (2002) Circulation Research 91:50t.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Brunt et al.; Can. J. Physiol. Pharmacol., 90: 327-335, 2012.*
Naldini; Nature Reviews: Genetics, 12: 301-315, 2011.*
Nguyen et al. Advanced Drug Delivery Reviews, 62: 1175-1186, 2010.*
Wang et al., Stem Cells International, pp. 1-13, 2015.*
Atkinson, Stuart P., "Rejuvenating Old Stem Cells—miRNA KO is the Way?", Stem Cells Journal Online Community, http://www.stemcellsportal.com/article-scans/rejuvenating-old-stem-cells---mirna-ko-way, Oct. 10, 2016. 2 pages.
Okada et al., "Abrogation of Age-Induced MicroRNA-195, Rejuvenates the Senescent Mesenchymal Stem Cells by Reactivating Telomerase", Stem Cells 2015;00:00-00 www.StemCells.com, 12 pages.
U.S. Office Action dated Jul. 27, 2017, from U.S. Appl. No. 14/951,354.
Wilson, et al., MicroRNA Profiling of Human-Induced Pluripotent Stem Cells, 2009, Stem Cells and Development, 18(5): 749-757 and Supplemental Material.

(Continued)

*Primary Examiner* — Thaian N Ton
(74) *Attorney, Agent, or Firm* — Boulware & Valoir

(57) ABSTRACT

This disclosure provides a chemically modified induced pluripotent stem (iPS) cell derived from parental cells and methods for generating the chemically induced pluripotent stem (iPS) cells, as well as cardiac progenitor cells capable of producing cells of multiple sub-lineages. The iPS cells are useful in method for or regenerating cardiac muscle tissue or to promote the replacement of cardiac scar tissue or to rejuvenating cardiac muscles in a patient in need thereof and to treat cardiac disease.

12 Claims, 28 Drawing Sheets

Specification includes a Sequence Listing.

(56) References Cited

OTHER PUBLICATIONS

Nishino K. et al., "DNA Methylation Dynamics in Human Induced Pluripotent Stem Cells Over Time", 2011, PLoS Genet 7(5): e1002085, 14 pages.
Russell Angela J. "Regenerative Medicinal Chemistry: The in Situ Control of Stem Cells", ACS Med. Chem. Lett. 2013, 4, 365-368.
Final Office Action for U.S. Appl. No. 14/255,789, dated Dec. 2, 2016.
Non-Final Office Action for U.S. Appl. No. 14/951,354, dated Nov. 28, 2016.
U.S. Appl. No. 14/591,354.
Amato, RJ, "Inhibition of DNA methylation by antisense oligonucleotide MG98 as cancer therapy", Clin. Gentoruin Cancer, Dec. 5, 2007,(7):422-426.
Chappell et al., MYC/MAX Control ERK signaling and pluripotency by regulation of dual-specificity phosphatases 2 and 7, Genes & Dev., 2013, 27:725-733.
Cibelli et al., "Parthenogenetic Stem Cells in Nonhuman Primates", Science, 2002, 295(5556):819.
Desponts et al., "Using small molecules to improve generation of induced pluripotent stem cells from somatic cells", Methods in Molecular Biology, 2010, vol. 636, pp. 207-218.
Durrani et al., "Skeletal myoblasts for cardiac repair", Regen. Med., 2010, 5(6):919-932.
Goffin et al., "DNA methyltransferase inhibitors-state of the art", Ann. Oncol. Nov. 13, 2002(11):1699-1716.
Huangfu et al., "Induction of pluripotent stem cells by defined factors is greatly improved by small-molecule compounds", Nat Biotechnol., Jul. 2008;26, (7):795-7.
Igura et al., "Identification of small juvenile stem cells in aged bone marrow and their therapeutic potential for repair of the ischemic heart", Am J Physiol Heart Circ Physiol., Nov. 1, 2013, 305(9):H1354-62.
International Search Report and Written Opinion of the International Searching Authority (ISA/US) in International Application No. PCT/US2015/026016, dated Jul. 21, 2015, 13 pages.
Kim et al., "Cardiac stem cells with electrical stimulation improve ischemic heart function through regulation of connective tissue growth factor and miR-378", Cardiovasc Res., Nov. 1, 2013, 100(2):241-51.
Lichner et al., "The miR-290-295 cluster promotes pluripotency maintenance by regulating cell cycle phase distribution in mouse embryonic stem cells", Differentiation, Jan. 2011, 81(1):11-24.
Nakagawa et al., "Generation of induced pluripotent stem cells without Myc from mouse and human fibroblasts", Nat. Biotechnol., 2008, 26(1):101-106. Advance online publication Nov. 30, 2007.
Ni, T.T. et al. (2011) "Discovering small molecules that promote cardiomyocyte generation by modulating Wnt signaling," Chem Biol. 18(12):1658-1668.
Ni, T.T. et al., "Discovering Small Molecules that Promote Cardiomyocyte Generation by Modulating Wnt Signaling", Chemistry & Biology, Dec. 23, 2011, 18, 1658-1668.
Okita et al., "Generation of germline-competent induced pluripotent stem cells", Nature 2007 448:313-317.
Pasha et al., "Efficient non-viral reprogramming of myoblasts to stemness with a single small molecule to generate cardiac progenitor cells", PLoS One, 2011, 6(8):e23667.
Ren Y et al., 2011. Small molecule Wnt inhibitors enhance the efficiency of BMP-4-directed cardiac differentiation of human pluripotent stem cells. J. Mol. Cell. Cardiol. 51:280-87.
Russell, J.L. et al., "Targeting native adult heart progenitors with cardiogenic small-molecules," ACS Chem Biol., 2012, 7(6):1067-1076.
Sadek et al., "Cardiogenic small molecules that enhance myocardial repair by stem cells", Proc Natl Acad Sci U S A., Apr. 22, 2008, 105(16):6063-8.
Science Daily, "A simple new way to induce pluripotency: ACID", Nature, Jan. 29, 2104 (sciencedaily.com/releases/2014/01/14012918445.
Shi et al., "A combined chemical and genetic approach for the generation of induced pluripotent stem cells", Cell Stem Cell., Jun. 5, 2008, 2(6):525-8.
Sigma-Aldrich Co., LLC, "Product Information for MISSION Synthetic miRNA Inhibitors", 2013, 2 pages.
Sigma-Aldrich, Search term: "Isoxazole," http://www.sigmaaldrich.com. Last accessed Aug. 7, 2016.
Takahaski et al., "Induction of Pluripotent Stem Cells from Adult Human Fibroblasts by Defined Factors", Cell, Nov. 30, 2007, 131:861-872. Advance online publication Nov. 20, 2007.
Takahaski et al., "Induction of Pluripotent Stem Cells from Mouse Embryonic and Adult Fibroblast Cultures by Defined Factors", Cell, Aug. 25, 2006, 126:663-76.
Non-Final Office Action for U.S. Appl. No. 14/255,789, dated May 31, 2016.
Varna et al., "Nonhuman primate parthenogenetic stem cells", Proc. Natl. Acad. Sci. USA, 2003, 100(Suppl.1)11911-6.
Yu et al., "Induced Pluripotent Stem Cell Lines Derived from Human Somatic Cells", Science, Dec. 21, 2007, vol. 318, 1917-1920. Science advance online publication Nov. 20, 2007.
Zhu et al., "Reprogramming of human primary somatic cells by and chemical compounds", Cell Stem Cell, 2010, vol. 7, No. 6, pp. 651-655.

\* cited by examiner

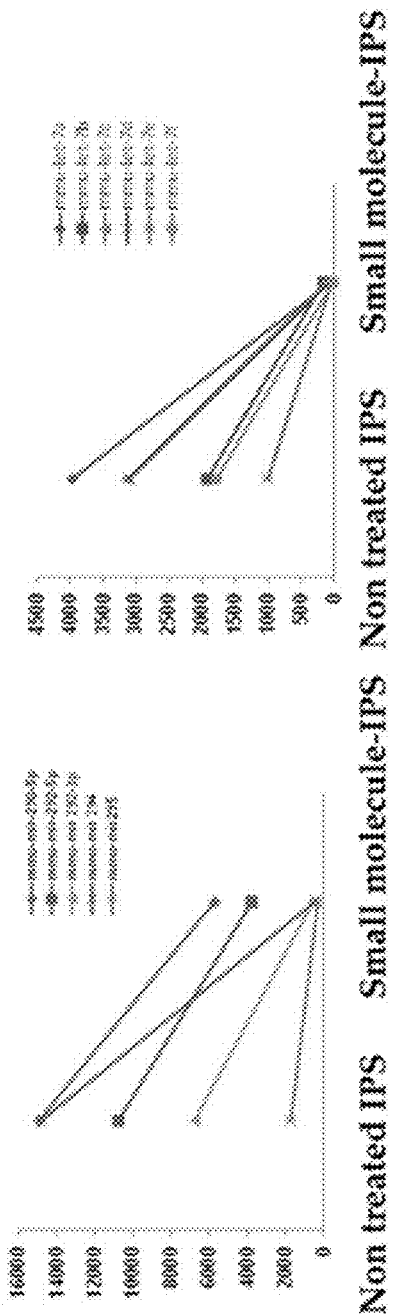
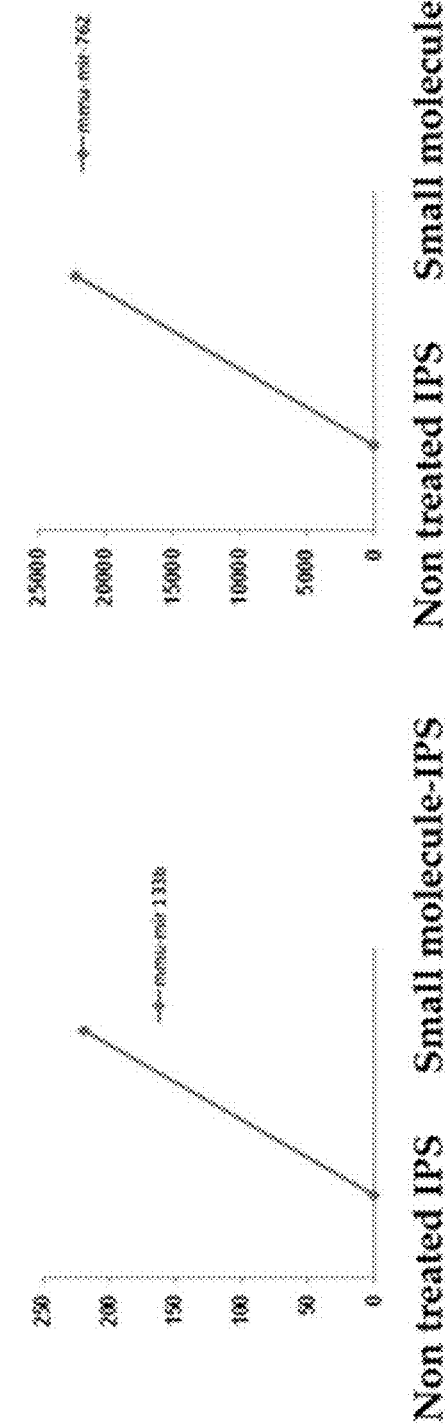
FIG. 7A
FIG. 7B
FIG. 7C
FIG. 7D

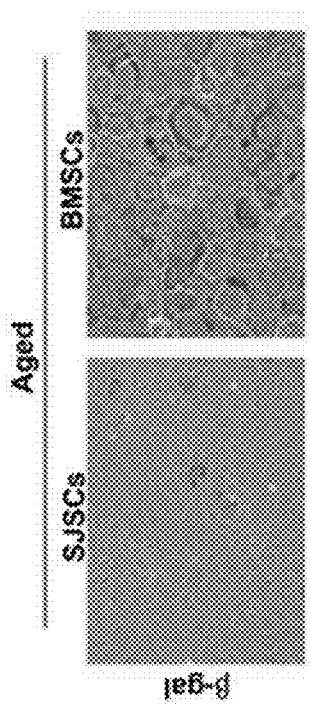
FIG. 9G
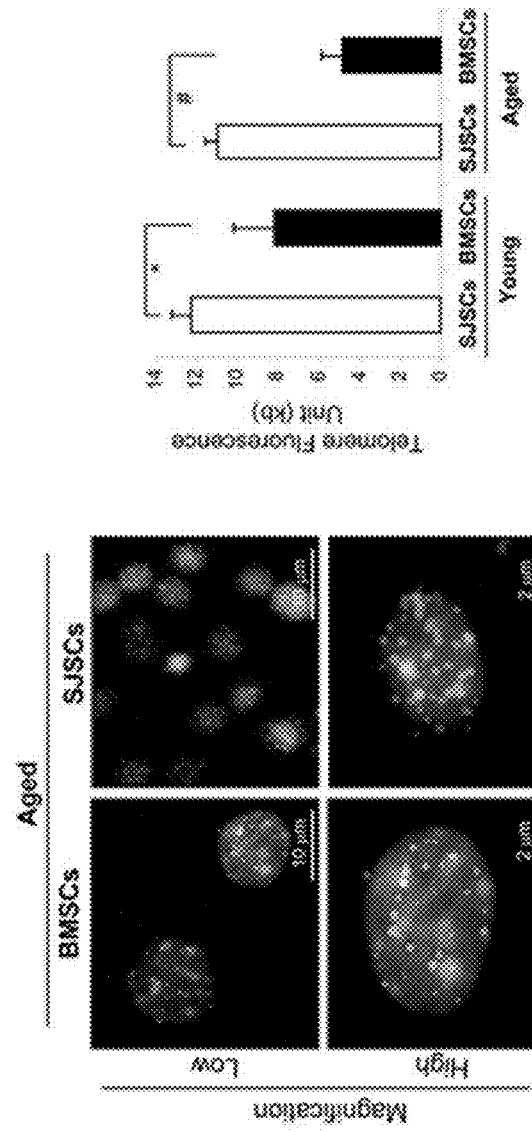
FIG. 9I
FIG. 9H

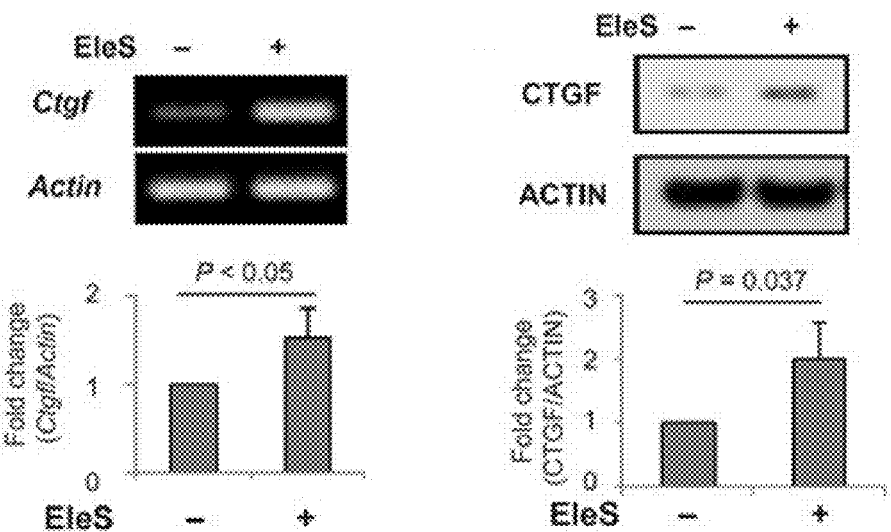
FIG. 11A
FIG. 11B
FIG. 11C
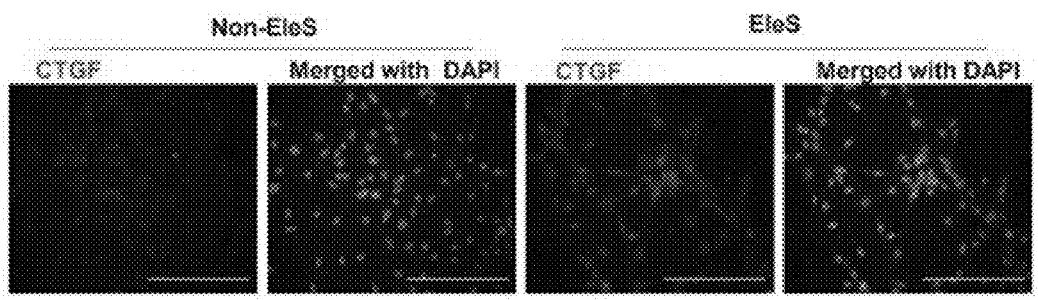
FIG. 11D

GENERATING CARDIAC PROGENITOR CELLS FROM PLURIPOTENT STEM CELLS USING ISOXAZOLE OR ISOXAZOLE LIKE COMPOUNDS

CROSS-REFERENCE TO RELATED APPLICATIONS

This application is a continuation-in-part under 35 U.S.C. § 120 of U.S. application Ser. No. 14/255,789, filed Apr. 17, 2014, and U.S. application Ser. No. 14/951,354, filed Nov. 24, 2015, the content of each of which is incorporated herein by reference in its entirety.

The instant application contains a Sequence Listing which has been submitted electronically in ASCII format and is hereby incorporated by reference in its entirety. Said ASCII copy, created on Sep. 9, 2016, is named 107808-0151_SL.txt and is 666 bytes in size.

BACKGROUND

Throughout this disclosure, various technical and patent publications are referenced to more fully describe the state of the art to which this invention pertains, the full bibliographic citations for some of the publications are found at the end of the specification, immediately preceding the claims. All publications noted in the present specification are incorporated by reference, in their entirety, into this application.

Induced pluripotent stem (iPS) cells are important source for progenitors, such as cardiac progenitors, for drug discovery and the treatment of disease, e.g., infracted myocardium. Due to inherent properties of iPS cells to form teratomas, it becomes very important to generate iPS cells without producing tumors for use in clinics. Given the importance of these concerns, efforts have been made to improve the reprogramming efficiency and several methods have been devised for the non-viral generation of iPS cells. Various growth factors and chemical compounds, such as DNA methyltransferase inhibitor (5'-azacytidine and RG108), histone deacetylase inhibitors (e.g., valproic acid), histone methyltransferase inhibitor (BIX-01294), Wnt3A, and ALK5 inhibitor, have been found to improve the induction efficiency. (1-6) With different experimental manipulations, iPS cells can be induced to cardiac lineage cells prior to their transplantation. These procedures are labor intense and not efficient in producing unlimited number of cells for the treatment of CVS diseases. Thus, a need exists for methods to produce safe iPS cells for the use in the clinic and for drug development. This invention satisfies this need and provides related advantages as well.

SUMMARY OF THE DISCLOSURE

This disclosure provides a chemically induced pluripotent stem (iPS) cell, progenitor cell, or stem cell characterized by DNA hypomethylation. In one aspect, the cell is modified by contacting the iPS or stem cell with an effective amount of an isoxazole or isoxazole similar compound. In another aspect, the amount of an isoxazole or isoxazole similar compound is an effective amount to derive a progenitor cell, such as a cardiac progenitor cell. In yet one aspect, the iPS cell is derived from a parent cell selected from the group consisting of a bone marrow cell, an adipose derived stem cell, a mesenchymal stem cell, a bone marrow stromal cell, an hematopoietic stem cell, a myoblast, a cord blood cell, a small juvenile stem cell, a cardiac progenitor cell, an adult peripheral blood cell, a mononuclear cell, or a skin fibroblast. In one aspect, the modified iPS, progenitor or stem cells (having been contacted with an effective amount of isoxazole or isoxazole similar compound, are, in one aspect, further characterized in that the cell expresses or overexpresses one or more cardiac genes or markers, non-limiting examples of such include Nkx-2.5, ISL1, GATA4, αMHC, Sarcomeric actin, Gαi, miR-133, miR-762, CCL7, CXCR2, CXC5, integral membrane protein 2A, and ephrin A3. In another aspect, the chemically treated cell under expresses one or more pluripotent genes or markers, non-limiting examples of such include one or more of miR-290-295 cluster, let-7 family, Max and/or under expresses one or more DNA methyltransferase genes, including but not limited to Dnmt1 and/or Dnmt3b.

In one aspect, the iPS, progenitor or stem cell was created by a method comprising, or alternatively consisting essentially of, or yet further consisting of, contacting a parent cell with an effective amount of a DNA methyltransferase inhibitor to upregulate Oct4. Non-limiting examples of DNA methyltransferase inhibitors include 5'-azacytidine, 5-aza-2'-deoxycytidine, MG98, zebularine and RG108. In one aspect, the iPS, progenitor, or stem cell was created by a method that excludes the insertion of exogenous genes into the parent cell, such as by viral transduction of pluripotency transgenes. In another aspect, the iPS, progenitor, or stem cell was created by a method that comprises the insertion of pluripotency transgenes, with or without viral transduction of those genes.

In a yet further embodiment, the parent cells are progenitor cells, non-limiting examples of such include without limitation, a cardiac progenitor cell. In one aspect, the parental cells are progenitor cells, e.g., cardiac progenitor cells that were preconditioned with an effective amount of electrical stimulation. In another aspect, the parent cells are stem cells that express one or more of Sca-1, pluripotency and cardiac genes as described herein. In another aspect, the parent cells are juvenile or young stem cells that can be identified by low expression of miR-195 as compared to a cell that does not express the characteristics of a young or juvenile cell as described herein. In a further aspect, the parent cell is further characterized by low expression of one or more marker selected from miR-29b, miR-205, miR-378, and miR-542-3p as compared to a cell that does not express the characteristics of a young or juvenile cell as described herein.

Further provided by this disclosure is a population of chemically-treated iPSC, stem or progenitor cells, treated as noted above. In a further aspect, this disclosure is a population of cardiac lineage cells or cardiac progenitors having the characteristics as described above. In one aspect, the population is substantially homogenous or heterogeneous or clonal. In another aspect, the population produces one or more of cardiomyocytes, cardiac cells, endothelial cells, vascular endothelial cells or smooth muscle cells.

Also provided is a method for preparing one or more of: a cardiomyocyte, an endothelial cell, a vascular endothelial cell, a smooth muscle cell, a cardiac lineage cell from a stem cell or progenitor cell, including but not limited to an iPS cell, comprising, or alternatively consisting essentially of, or yet further consisting of, contacting the stem, progenitor or iPS cell with an effective amount of an isoxazole compound or isoxazole similar compound. Yet further provided is a method for preparing cells of multiple linages, e.g. a cardiomyocyte, an endothelial cell, a vascular endothelial cell, a smooth muscle cell, cardiac lineages from a cell selected from a progenitor cell, a iPS cell, and a stem cell, comprising, or alternatively consisting essentially of, or yet further consisting of, contacting the cell with an effective amount of an isoxazole compound or isoxazole similar compound. The contacting may be performed in vitro or in vivo. Non-limiting examples of stem cells are selected from a bone marrow cell, a myoblast, a cord blood, a cardiac progenitor cell, a hematopoietic stem cell, a bone marrow stromal cell, a mesenchymal stem cell, an electrically stimulated progenitor (e.g. an electrically stimulated cardiac progenitor), a SJSC, and an adult peripheral blood cell, also described in the literature as a mononuclear cell (e.g., a peripheral blood mononuclear cell (PMBC). In one aspect, when the iPS cells are cultured to produce a cardiac lineage cell, the methods provided herein produce a cardiac lineage cell that expresses or overexpresses one or more cardiac genes or markers. Non-limiting examples of the one or more cardiac gene or marker are Nkx-2.5, ISL1, GATA4, αMHC, Sarcomeric actin, Gαi, mir-133, mir-762, CCL7, CXCR2, CXC5, integral membrane protein 2A and ephrin A3. In addition or alternatively, the cardiac lineage cells under expresses one or more pluripotent genes or markers. Non-limiting examples of the one or more pluripotency gene or marker are one or more of miR-290-295 cluster, let-7 family and/or expresses one or more DNA methyltransferase genes, Dnmt1, Dnmt3b, and Max. As apparent to the skilled artisan, the methods disclosed herein produce cardiac lineage cells, cardiac progenitors, striated cardiomyocyte fibers having a beating, striated phenotype, transforming the mature cardiomyocyte cells into a cardiomyocyte-like heart muscle fiber having a beating, striated phenotype and regenerated heart muscle via chemically modified/treated IPS cells. Thus, the methods are useful to produce and use these cells diagnostically and/or therapeutically. As such, this disclosure overcomes limitation of current cardiomyocyte differentiation methods generate that produce a cell population at a low yield and/or a heterogeneous cell population consisting of atrial, pacemaker and ventricular cardiomyocytes. Prior art methods to pure populations required genetic manipulation with viral vectors that enable either drug selection or sorting which do not satisfy the criteria for therapeutic applications. In yet other prior art methods, the stem cells are exposed to a variety of growth factors or are inefficient. In contrast to prior art methods, this disclosure produces consistent, high yield and therapeutically-relevant cell populations that in turn, are useful in cell-replacement therapies or transplantations and can be used for the prevention or treatment of cardiovascular diseases and disorders. They also are useful in pre-clinical and diagnostic applications such as for screening compounds for toxicity and screening for new agonist, antagonist or other small molecule or genetically-related methods, for eventual clinical application.

Cells of other lineages are prepared by modification of the culture conditions of the cells after treatment with the effective amount of isoxazole or isoxazole-like compound. As shown in FIG. 14C, cardiac progenitor cell are cultured with an effective amount of RPMI/B27 (without insulin) for about 7 days, and then cultured in RPMI/B27 for about 7 days. The cells can be differentiated into smooth muscle cells by culturing the cardiac progenitor cells in an effective amount of DMEM-F12 with TGFβ1 and PDGFBB. The cardiac progenitor cells can be differentiated into endothelial cells, e.g., vascular endothelial cells by culturing the cells in an effective amount of EGM-1 for an effective amount of time.

In one particular aspect, the stem cell is an iPS cell. In one aspect, the method to prepare the iPSC comprises, or alternatively consists essentially of, or yet further consists of, contacting a parent cell with an effective amount of a DNA methyltransferase inhibitor to upregulate Oct4. Non-limiting examples of DNA methyltransferase inhibitors include 5'-azacytidine, 5-aza-2'-deoxycytidine, MG98, zebularine and RG108. In one aspect, the iPS cell was created by a method that excludes the insertion of exogenous genes into the parent cell. In one aspect, the method is performed in vitro, in a cell culture or alternatively, the method is practiced in vivo by administering to a tissue containing the parental cell with an effective amount of the DNA methyltransferase inhibitor. The administration by any appropriate method, e.g., by direct injection into the tissue containing the cells, is useful to reduce cell death in the ischemic area/improve heart function. In addition and/or alternatively, the parental cells are primed by electrical stimulation, that in one aspect comprises from about 1 hour (hr) to 5 hours, or alternatively from about 2 hrs to 4 hours, or alternatively for about 3 hrs duration at 1.0 to about 2.0 V, or alternatively from about 1.4 to about 1.7V, or alternatively from about 1.5V per 1.5 cm to about 2.0 cm, or alternatively from about 1.6 cm to about 1.7 cm, or alternatively from about 1.8 cm.

Further provided herein are methods to prepare populations of cells, such as substantially homogenous or heterogeneous or clonal population of cells, as described herein. They can be further modified by comprising, or alternatively consisting essentially of, or yet further consisting or a detectable label, by inserting into the cell the detectable label. In one aspect, further provided herein are methods to derive from the population one or more of cardiomyocytes, endothelial cells, or smooth muscle cells.

Yet further provided is a method for regenerating tissue, such as smooth muscle tissue, endothelial tissue, or cardiac muscle tissue or to promote the replacement of cardiac scar tissue in a patient in need thereof, by administering to the patient one or more of an effective amount of isoxazole, an isoxazole similar compound and/or an effective amount of the isolated cell as described herein. When administered to cardiac tissue, these methods reduce cell death in the ischemic area and/or improve heart function and therefore also provide methods for achieving these medical benefits as well.

Yet further provided is a method for rejuvenating cardiac muscle tissue or to promote the restoring and/or elevation of oxygen and/or nutrients and/or the like to cardiac tissue for treating cardiac disease in each patient in need thereof, by administering to the patient one or more of an effective amount of isoxazole, an isoxazole similar compound and/or an effective amount of the isolated cell as described herein.

Yet further provided is a method for treating cardiac disease in a patient in need thereof, by administering to the patient an effective amount of isoxazole, an isoxazole similar compound and/or an effective amount of the isolated cell or the population of cells as described herein.

Patients treated by the disclosed methods include a mammalian patient. Non-limiting examples of such include a murine, an equine, a bovine, a feline, a canine or a human patient. Cells may be autologous or allogeneic to the patient.

Yet further provided are kits to prepare the cells or administer the therapies as described herein, including the compositions or agents and instructions for use.

BRIEF DESCRIPTION OF THE FIGURES

In FIG. 3A, apoptosis was determined by TUNEL assay. Fewer TUNEL positive cells/microscopic field were observed in small molecule, isoxazole or isoxazole like compounds pretreated IPS as compared to control non-treated IPS cells. In FIG. 3B, an increase in mitogenic response of small molecule treated IPS was significantly noted in comparison with non-treated IPS cells. All values were expressed as mean±SEM, * $p<0.05$ vs. control.

FIG. 5A shows immunostaining of cardiac specific gene Nkx-2.5 and α Sarcomeric actin in small molecule treated IPS cells (merged images with DAPI), (original magnifications; 400×). FIG. 5B is RT-PCR analysis of cardiomyocyte specific marker, Nkx-2.5, in small molecule treated IPS cells in comparison with non-treated IPS cells. Small molecule, isoxazole or isoxazole like compounds treated IPS cells shows significant upregulation of Nkx-2.5 as isoxazole or isoxazole like compounds compared to non-treated IPS cells.

FIGS. 7A-7E show miR-microarray analysis of small molecule, isoxazole like compounds treated IPS vs non-treated IPS cells. Microarray analysis showing miR expression profile in non-treated IPS cells was quite different from small molecule treated IPS cells. (FIGS. 7A-7D) Critical miRs known for reprogramming and differentiation as observed in non-treated and small molecule treated IPS cells. miR Microarray analysis showed upregulation of cardiac specific miR-133, miR-762 and down regulation of pluripotency associated miR-290-295 cluster and let-7 family in small molecule treated IPS cells. FIG. 7E shows GPCR signaling in small molecule, isoxazole, or an isoxazole similar compound treated SIPs cells. Western blot analysis shows significant upregulation of Gα (pan) in small molecule treated IPS cells as compared to the non-treated IPS cells which was blocked by the concomitant use of GPCR blocker, pertussis toxin.

FIG. 8E, FIG. 8F.

FIGS. 9A-9I show the characterization of small juvenile stem cells (SJSCs) from heterogeneous bone marrow-derived stem cells (BMSCs) from young and old mouse described in Experiment No. 2. FIGS. 9A and 9B show that both aged and young SJSCs were positive for CD29, CD44, CD59, and CD90 but negative for CD45 and CD117 B. In FIG. 9C, cell growth curves show that the cell proliferation rate was higher in SJSCs than in BMSCs. Compared with aged BMSCs, aged SJSCs showed higher expression of pluripotency markers such as octamer-binding transcription factor 4 (Oct-4), Nanog, sex-determining region Y box 2 (Sox-2), Kruppel-like factor 4 (Klf-4), and Rex-1. FIG. 9D shows that cardiogenic differentiation markers such as Gata-4 and myocyte-specific enhancer factor 2C (Mef2c). FIG. 9E shows that antiaging markers such as sirtuin 1 (Sirt1) and telomerase reverse transcriptase (Tert) are expressed. In FIG. 9F, marker expression as examined by RT-PCR. In FIG. 9G, SJSCs from aged bone marrow showed less senescence-associated β-galactosidase (β-gal) expression compared with other cells in aged BM. FIG. 9H is confocal microscopy showing that aged SJSCs had a higher density of telomeres compared with aged BMSCs. FIG. 9I is quantitative fluorescence in situ hybridization (FISH) analysis demonstrated that SJSCs maintain longer telomeres compared with BMSCs. Telomere shortening was delayed in aged SJSCs compared with aged BMSCs.

FIG. 10A is a brief description of the procedure of CSCs isolation. FIG. 10B shows Sca-1$^+$ expression in isolated CSCs was validated by immunocytochemistry and flowcytometry. (light grey=Sca-1$^+$; dark grey=DAPI). In FIG. 10C, Discoidin domain receptor 2 (DDR2) and prolyl-4-hydroxylase beta (P4HB) antibodies were rarely positive in CSC cultures. FIG. 10D shows that expression of a hematopoietic progenitor marker (c-kit), pluripotency markers (Oct-4, Sox2, Nanog), a stem cell side population marker (Bcrp1), early cardiac lineage markers (Nkx-2.5, GATA4, MEF2C), and a vascular progenitor marker (Flk1) in isolated Sca-1$^+$ cell colonies as analyzed by RT-PCR. "C" notation above the columns stands for cultured colonies and their identity numbers. They maintained about 80~90% of Sca-1$^+$ positive cells from passage 5 to 30, measured by flow cytometry. All experiments were performed within this passage. Bar=100 µm.

FIGS. 11A-11D show that connective tissue growth factor ("CTGF") is a major downstream factor for electrically stimulated-induced focal adhesion kinase (FAK)-AKT ("FAK/AKT") pathways. CTGF is a major downstream factor for EleS-induced FAK/AKT pathways. FIG. 11A shows the results of real-time PCR-based gene expression profiling performed for extracellular matrix ("ECM") and cell adhesion molecules. Four of each up-regulated and down-regulated genes were selected based on fold change. In FIGS. 11B and 11C, mRNA expression of connective tissue growth factor ("CTGF") was confirmed by conventional RT-PCR and real-time PCR (n=5). FIG. 11D shows CTGF positivity by immunocytochemistry was higher in electrically stimulated cardiac stem cells ("EleS CSCs")

when compared with non-electrically stimulated cardiac stem cells ("Non-EleS CSCs").

Figure 12A:
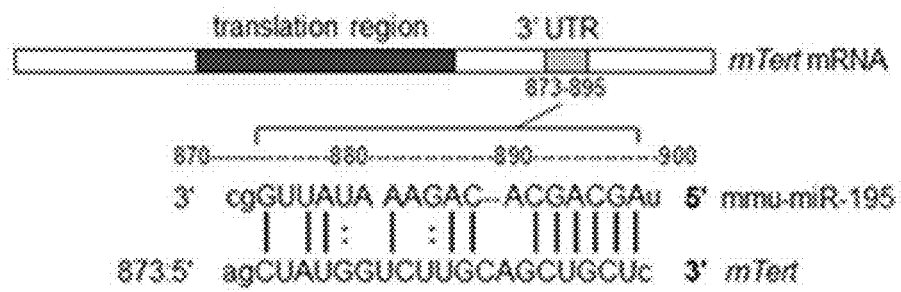
Figure 12B:
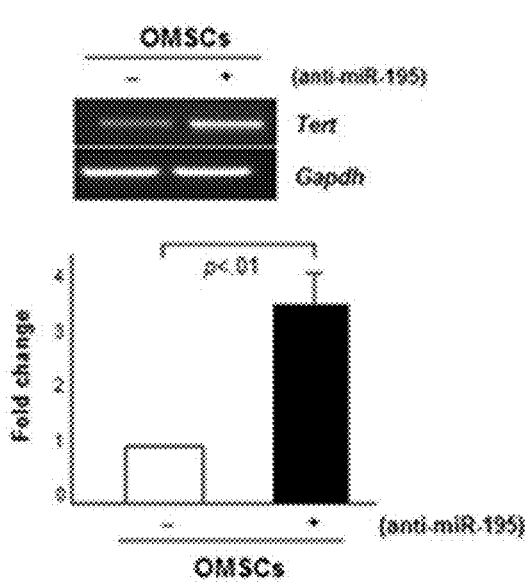
Figure 12C:
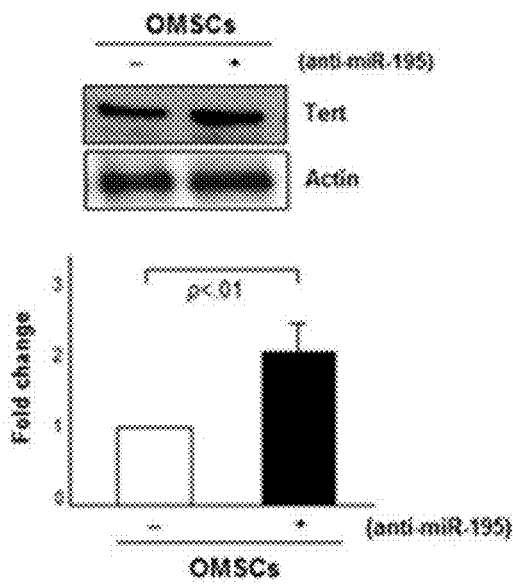
Figure 12D:
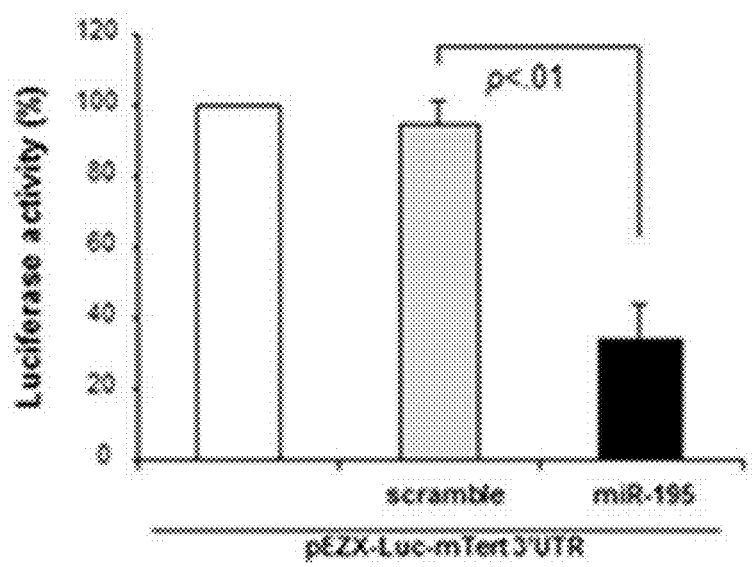

FIGS. 12A-12D show that "Tert" is a direct target of miR-195 in stem cell aging. FIG. 12A shows computational analysis predicted "mTert" (SEQ ID NO. 2) as a potential target of mmu-miR-195 (SEQ ID NO. 1). FIGS. 12B and 12C show transfection of OMSCs with anti-miR-195 restored expression of Tert mRNA as well as telomere specific protein TRF2, as examined by reverse transcriptase polymerase chain reaction and Western blot, respectively. FIG. 12D shows cotransfection with pEZX-Luc vector containing mTert 3' UTR and a plasmid encoding miR-195 showed decreased luciferase activity (p<0.01 vs. pEZX-miR-SC transfected cells). Transfection efficiency was normalized by Renilla luciferase activity. Acronyms: OMSCs, old mesenchymal stem cells; Tert, telomerase reverse transcriptase; UTR, untranslated region.

Figure 13A:
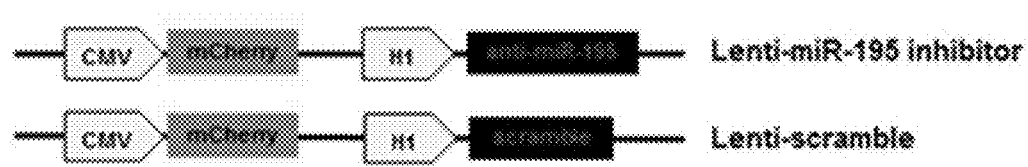
Figure 13B:
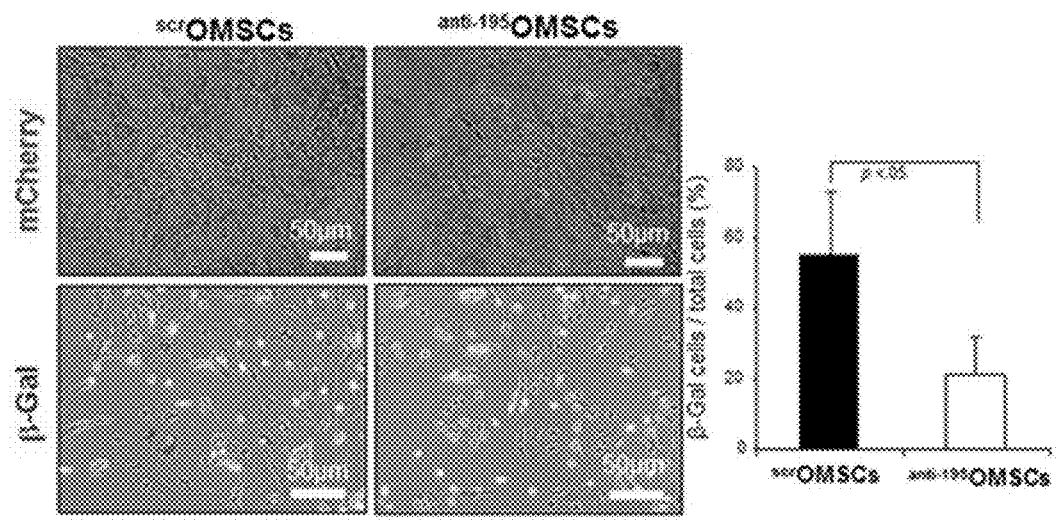
Figure 13C:
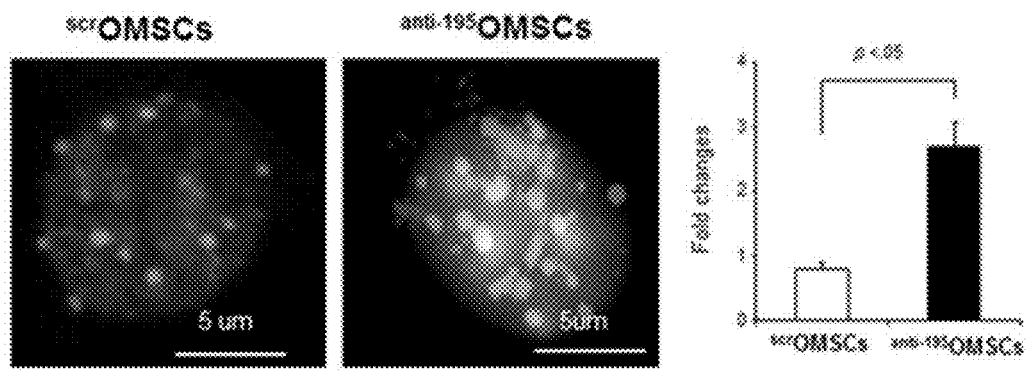
Figure 13D:
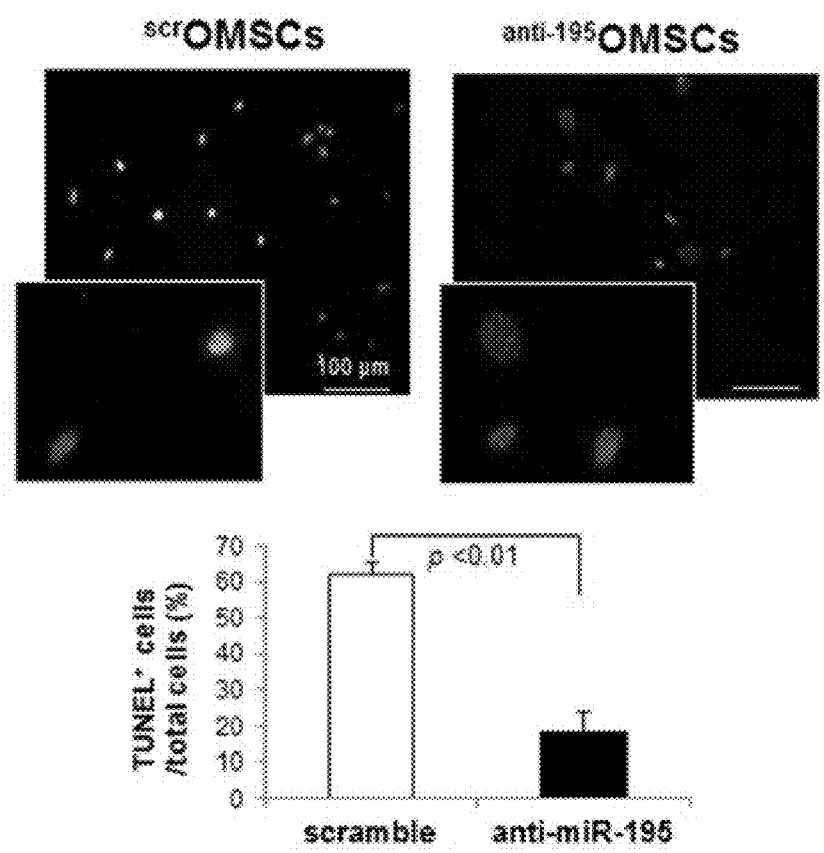
Figure 13E:
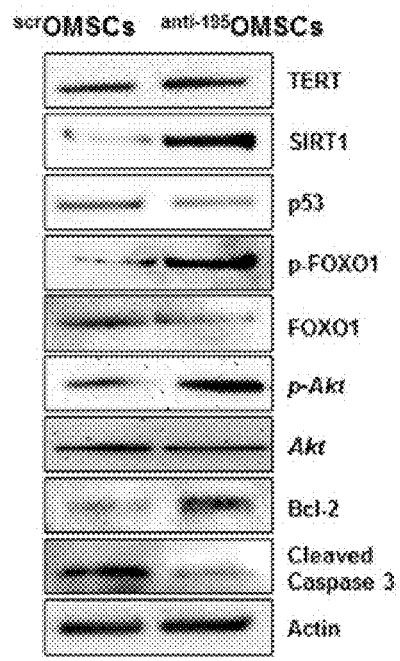
Figure 13F:
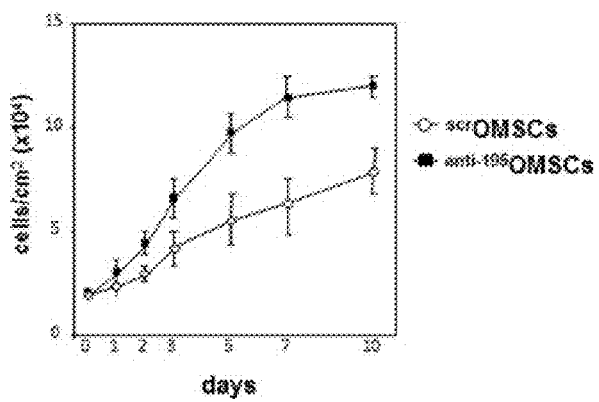
Figure 13G:
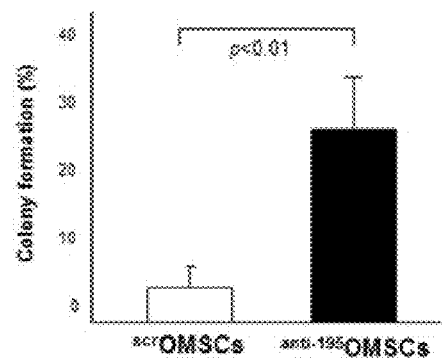

FIGS. 13A-13G show abrogation of miR-195 rejuvenates OMSCs by telomere relengthening and antiaging markers reactivation. FIG. 13A shows the structures of Lenti-miR-195 inhibitor and Lenti-scramble vectors which contain mCherry reporter gene (red signal). FIG. 13B shows abrogation of miR-195 significantly reduced senescence-associated b-gal expression in OSMCs as compared to scramble transfected OMSCs. FIG. 13C shows significant telomere relengthening of OMSCs upon transfection with miR-195 inhibitor. FIG. 13D shows that miR-195 inhibition markedly reduced terminal deoxynucleotidyl transferase dUTP nick end labeling-positive apoptotic cell death in OMSCs. FIG. 13E shows that expressions of TERT [not shown], SIRT1, and Bcl-2 as well as phosphorylation of p-FOXO1 and p-Akt were significantly increased by transfection of anti-miR-195 in OMSCs whereas expression of p53 and cleaved caspase 3 was reduced by miR-195 abrogation. FIGS. 13F and 13G show knockdown of miR-195 significantly restored cell proliferative abilities in OMSCs as examined by cell proliferation assay and colony formation assay. Acronyms: OMSCs, old mesenchymal stem cells; SIRT1, sirtuin (silent mating type information regulation 2 homolog) 1; Bcl-2, B cell lymphoma 2 protein, FOXO1, forkhead box protein 01 also known as forkhead in rhabdomyosarcoma is a protein, and p-FOXO1 is phospho-forkhead box protein O1, Akt, protein kinase B (PKB), also known as Akt, p-Akt is phospho-Akt.

Figure 14A:
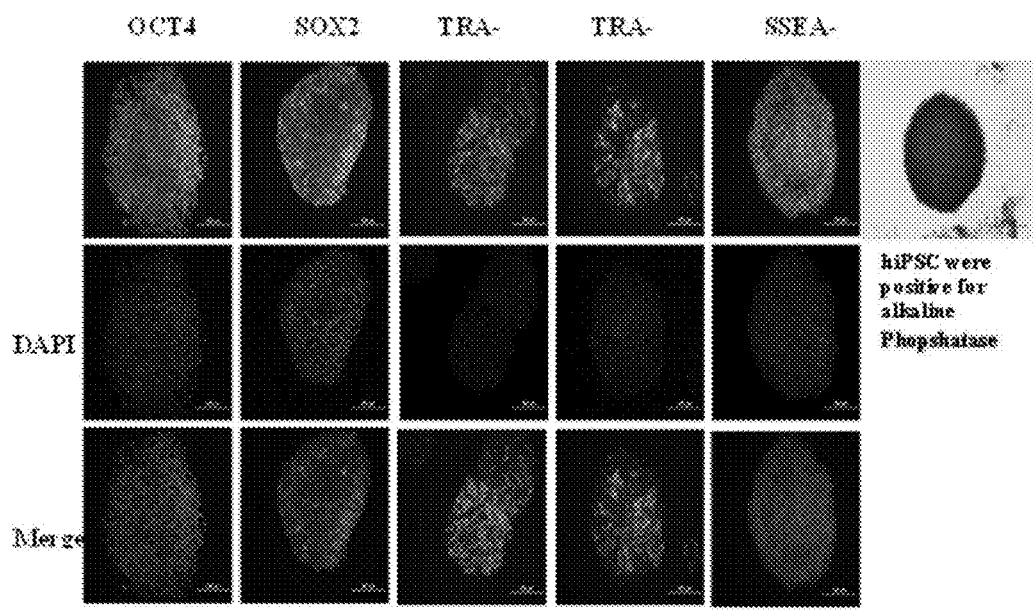
Figure 14B:
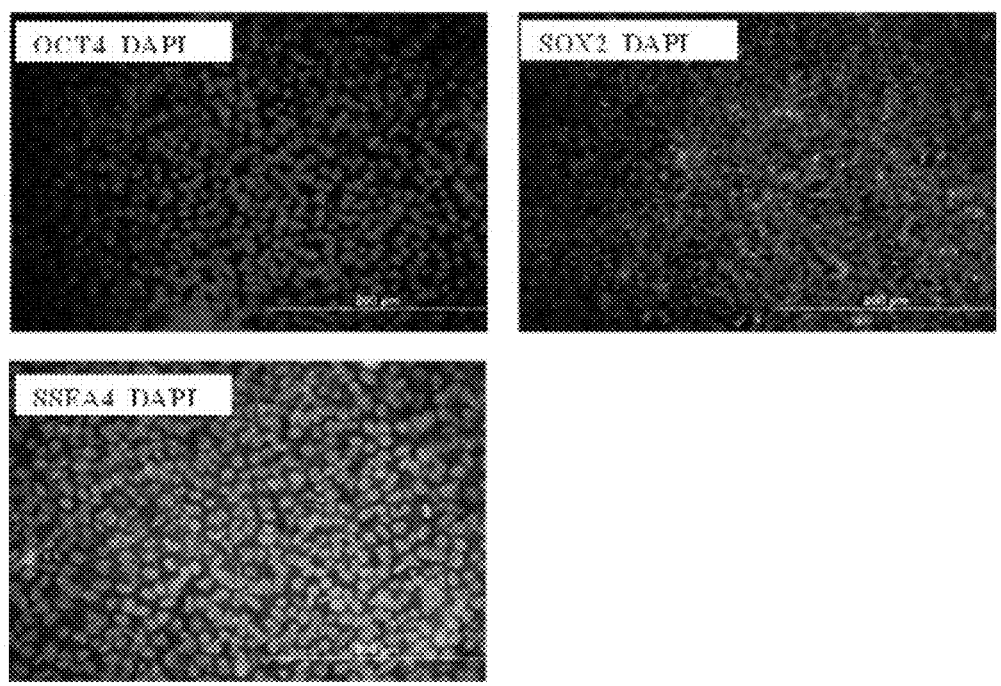
Figure 14C:
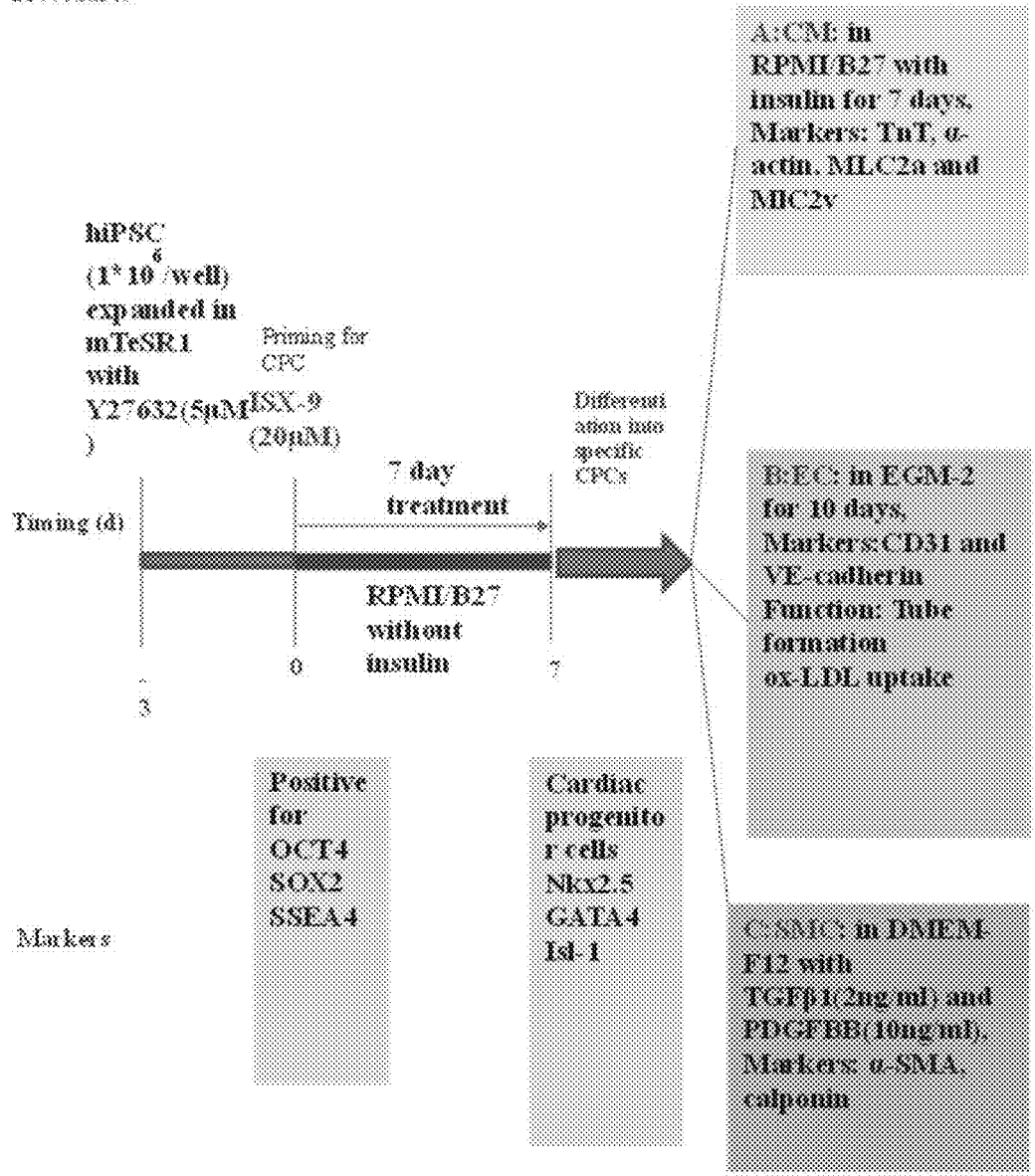
Figure 14D:
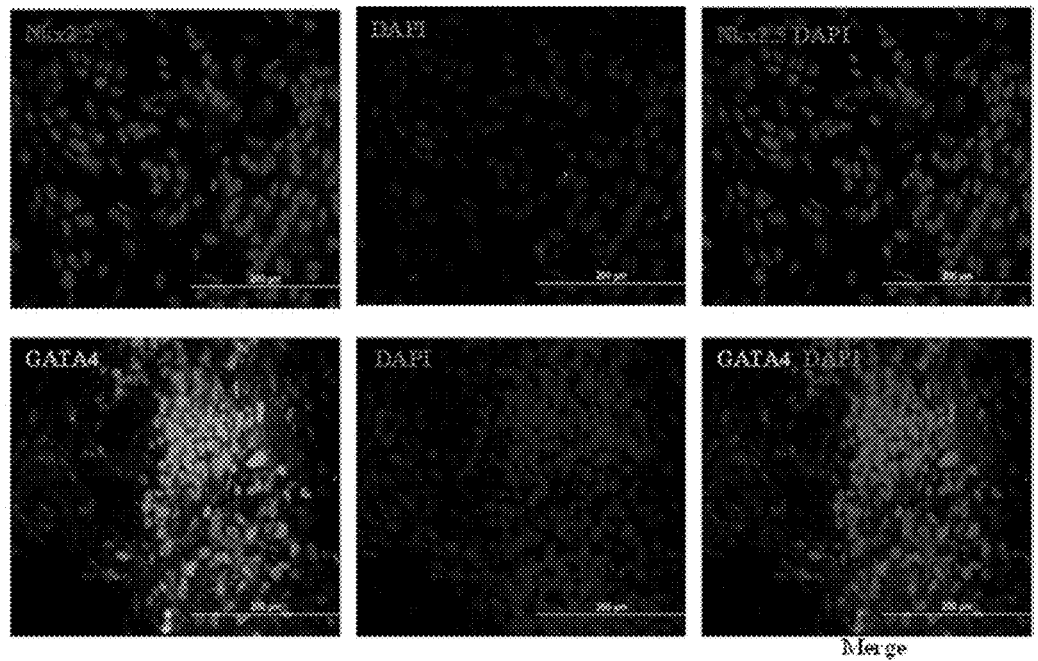
Figure 14E:
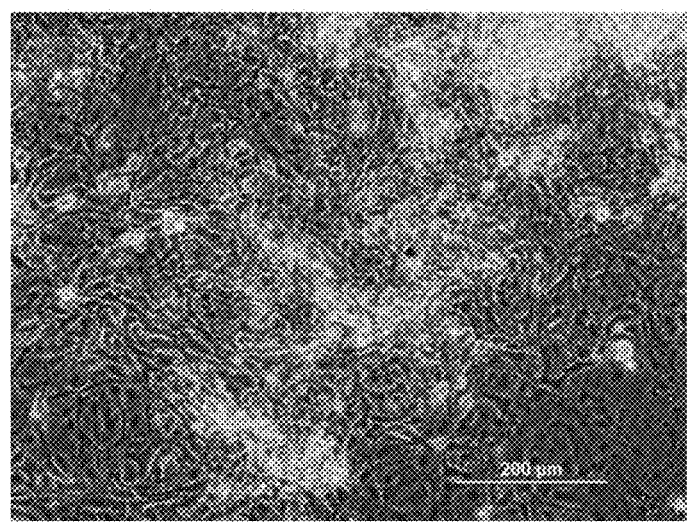
Figure 14F:
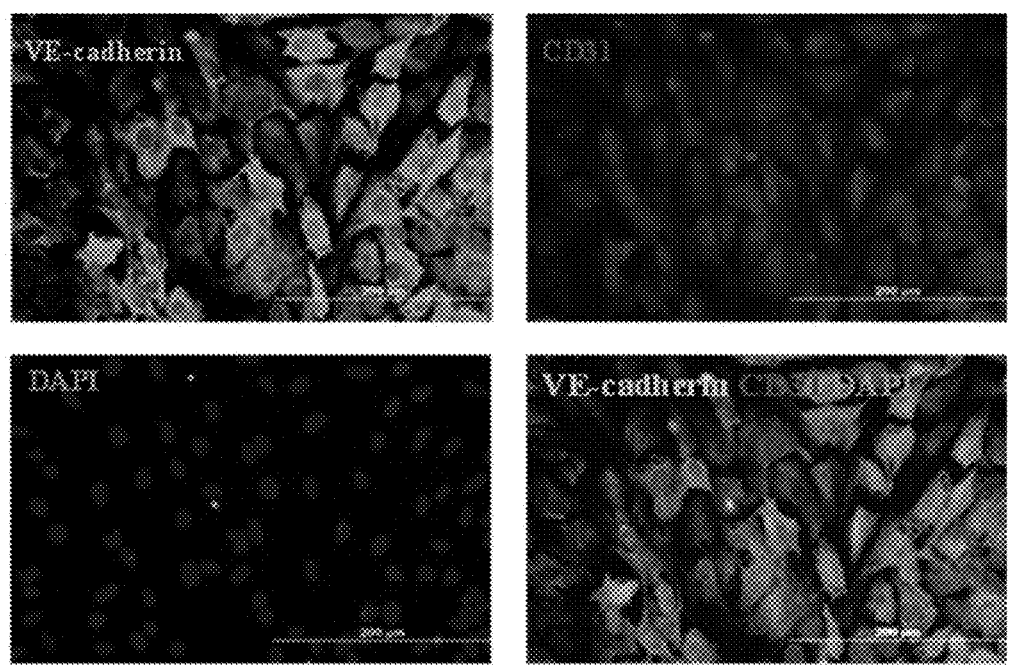
Figure 14G:
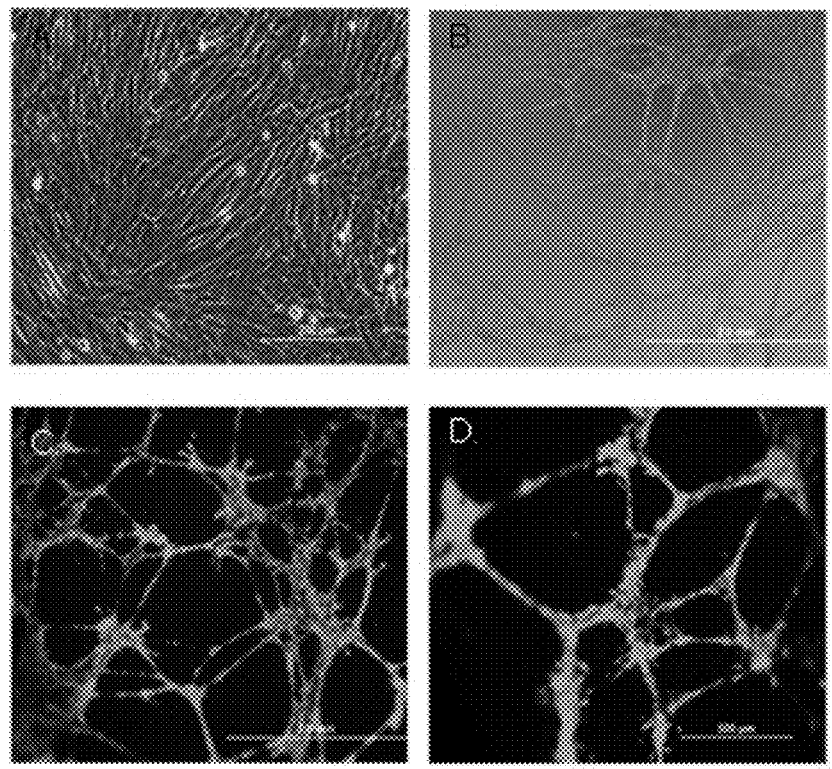
Figure 14H:
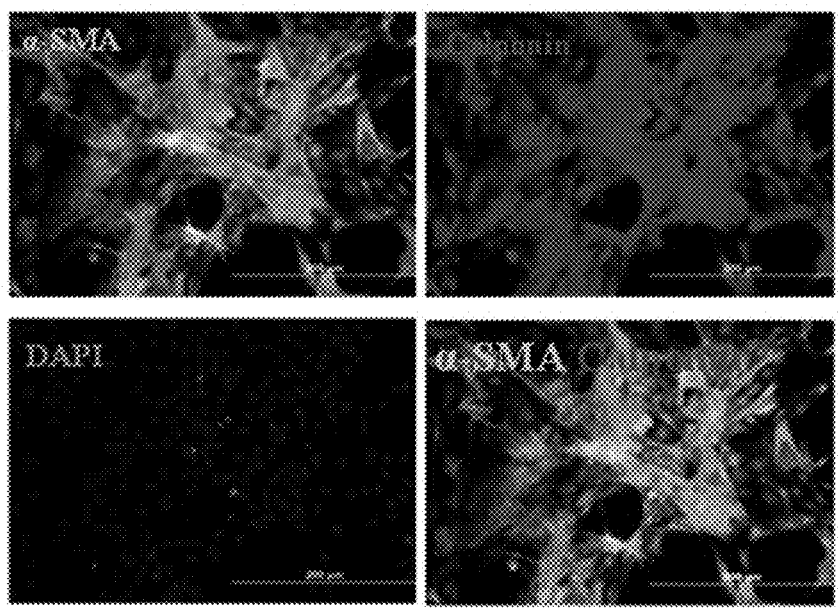

FIGS. 14A-14H show isoxazole or isoxazole like compounds mediated generation of cardiac progenitor cells from human induced pluripotent stem cells in vitro. FIGS. 14A-14B show the characterization of human iPS cells for the expression of pluripotency markers of Oct4, Sox2, Tra-1-60, Tra-1-81, and SSEA4 by immmunostaining (merged images with DAPI). FIG. 14C shows an exemplary brief description of the procedure of the generation of cardiac progenitor cells from hiPS cells and subsequent generation of cells of multiple cell lineages therefrom. FIG. 14D shows the characterization of cardiac progenitor cells with expression of the markers of Nkx2.5 and GATA4 by immunostaining (merged images with DAPI). FIG. 14E shows the differentiation of human iPS cells into beating cardiomyocytes. FIG. 14F shows in vitro differentiation of human iPS cells into vascular progenitor cells as demonstrated by the expression of VE-cadherin and CD31 by immunofluorescence analysis. FIG. 14G shows tube formation by vascular progenitor cells labeled with calcein-AM dye. FIG. 14H shows in vitro differentiation of human iPS cells into smooth muscle progenitor cells as shown by α-SMA and calponin immunostaining.

Figure 15A:
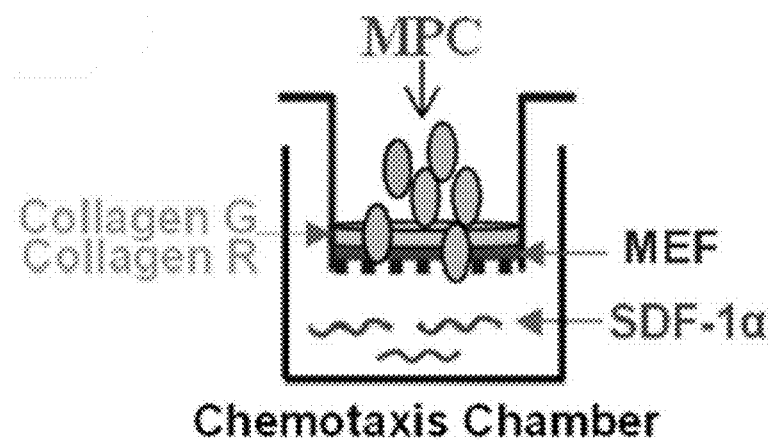
Figure 15B:
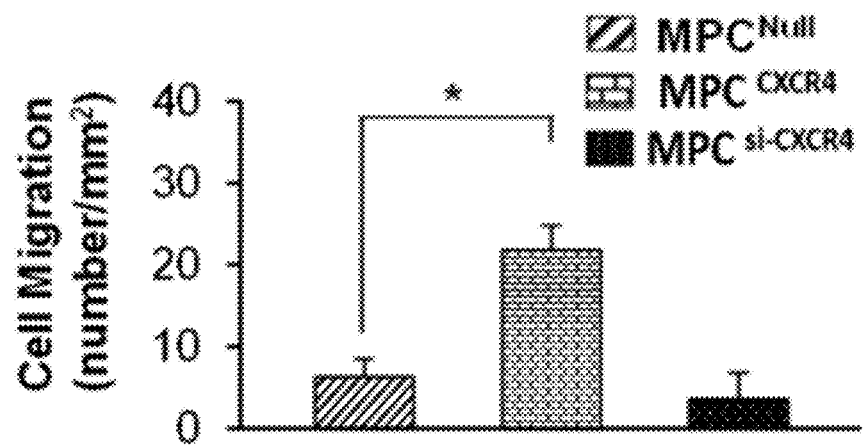

FIGS. 15A-15B show the effects of CXCR4 expression on muscle progenitor cell ("MPC") migration. Schematic representation of chemotaxis experiments for cell migration. FIG. 15A shown MPC invading the collagen gel were quantified by counting 30 optical fields per well. FIG. 15B shows MPC Null indicates GFP/dystrophin expressing control MPC; MPCCX4 indicates GFP/dystrophin expressing MPC that overexpress CXCR4; MPCsi-CXCR4 indicates MPC treated with siRNA targeting CXCR4 (MPCsi-CXCR4), for knock-down of CXCR4 gene. The data show increased migration of MPC overexpressing CXCR4. n=4, *p<0.05 vs. control.

DETAILED DESCRIPTION

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis (1989) Molecular Cloning: A Laboratory Manual, $2^{nd}$ edition; F. M. Ausubel, et al. eds. (1987) Current Protocols In Molecular Biology; the series Methods in Enzymology (Academic Press, Inc.): PCR 2: A Practical Approach (1995) (M. J. MacPherson, B. D. Hames and G. R. Taylor eds.); Harlow and Lane, eds. (1988) Antibodies, A Laboratory Manual; Harlow and Lane, eds. (1999) Using Antibodies, A Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

A "biocompatible scaffold" refers to a scaffold or matrix for tissue-engineering purposes with the ability to perform as a substrate that will support the appropriate cellular activity to generate the desired tissue, including the facilitation of molecular and mechanical signaling systems, without eliciting any undesirable effect in those cells or inducing any undesirable local or systemic responses in the eventual host. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. No. 6,638,369.

As used herein, a "cardiac patch" or "cardiac progenitor patch embedded in fibrin" or "Epicardial patch" is a bioengineered 2D or 3-dimensional (3D) tissue patch comprising or containing iPS cells or iPS cells derived cardiac lineage or cardiac progenitor cells.

A "cardiomyocyte" or "cardiac myocyte" is a specialized muscle cell which primarily forms the myocardium of the heart. Cardiomyocytes have five major components: 1. cell membrane (sarcolemma) and T-tubules, for impulse conduction, 2. sarcoplasmic reticulum, a calcium reservoir needed for contraction, 3. contractile elements, 4. mitochondria, and 5. a nucleus. Cardiomyocytes can be subdivided into subtypes including, but not limited to, atrial cardiomyocyte, ventricular cardiomyocyte, SA nodal cardiomyocyte, peripheral SA nodal cardiomyocyte, or central SA nodal cardiomyocyte. Stem cells can be propagated to mimic the physiological functions of cardiomyocytes or alternatively, differentiate into cardiomyocytes. This differentiation can be detected by the use of markers selected from, but not limited to, myosin heavy chain, myosin light chain, actinin, troponin, tropomyosin, GATA4, Mef2c, and Nkx-2.5.

The cardiomyocyte marker "myosin heavy chain" and "myosin light chain" are part of a large family of motor proteins found in muscle cells responsible for producing contractile force. These proteins have been sequenced and characterized, see for example GenBank Accession Nos. AAD29948, CAC70714, CAC70712, CAA29119, P12883, NP_000248, P13533, CAA37068, ABR18779, AAA59895, AAA59891, AAA59855, AAB91993, AAH31006, NP_000423, and ABC84220. The genes for these proteins has also been sequenced and characterized, see for example GenBank Accession Nos. NM_002472 and NM_000432.

The cardiomyocyte marker "actinin" is a mircrofilament protein which are the thinnest filaments of the cytoskeleton found in the cytoplasm of all eukaryotic cells. Actin polymers also play a role in actomyosin-driven contractile processes and serve as platforms for myosin's ATP hydrolysis-dependent pulling action in muscle contraction. This protein has been sequenced and characterized, see for example GenBank Accession Nos. NP_001093, NP_001095, NP_001094, NP_004915, P35609, NP_598917, NP_112267, AA107534, and NP_001029807. The gene for this protein has also been sequenced and characterized, see for example GenBank Accession Nos. NM_001102, NM_004924, and NM_001103.

The cardiomyocyte marker "troponin" is a complex of three proteins that is integral to muscle contraction in skeletal and cardiac muscle. Troponin is attached to the protein "tropomyosin" and lies within the groove between actin filaments in muscle tissue. Tropomyosin can be used as a cardiomyocyte marker. These proteins have been sequenced and characterized, see for example GenBank Accession Nos. NP_000354, NP_003272, P19429, NP_001001430, AAB59509, AAA36771, and NP_001018007. The gene for this protein has also been sequenced and characterized, see for example GenBank Accession Nos. NM_000363, NM_152263, and NM_001018007.

"Clonal proliferation" refers to the growth of a population of cells by the continuous division of single cells into two identical daughter cells and/or population of identical cells.

CTGF, also known as CCN2 or connective tissue growth factor, is a matricellular protein of the CCN family of extracellular matrix-associated heparin-binding proteins (see also CCN intercellular signaling protein).

Telomerase reverse transcriptase ("TERT") is a catalytic subunit of the enzyme telomerase, which, together with the telomerase RNA component (TERC), comprises the most important unit of the telomerase complex.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include biocompatible scaffolds, pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype). Additionally, when the purpose of the experiment is to determine if an agent effects the differentiation of a stem cell, it is preferable to use a positive control (a sample with an aspect that is known to affect differentiation) and a negative control (an agent known to not have an affect or a sample with no agent added).

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

"Differentially expressed" intends an up- or downward expression of a gene or marker as compared to a control. In one aspect, a control is a differentiated cell as compared to a pluripotent or stem cell.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

As used herein, the term "differentiates or differentiated" defines a cell that takes on a more committed ("differentiated") position within the lineage of a cell. "Dedifferentiated" defines a cell that reverts to a less committed position within the lineage of a cell.

A DNA methyltransferase inhibitor is a small molecule or other agent the ability to inhibit hypermethylation, restore suppressor gene expression and exert antitumor effects in in vitro and in vivo laboratory models. Goffin and Eisenhauer (2002) Ann. Oncol. November 13(11):1699-16716. One non-limiting example of such an inhibitor is N-phthalyl-L-tryptopha (C19H14N2O4, sold under the tradename RG108, Sigma-Aldrich). Additional examples include 5'-azacytidine, 5-azacytidine, antisense oligonucleotides to methyltransferase 1, e.g., MG98 (see Amato (2007) Clin. Gentourin Cancer, December, 5(7):422-426 and 1-(β-D-Ribofuranosyl)-2(1H)-pyrimidinone (a nucleoside analog of cytidine, sold under the name Zebularine (Abcam®).

DNA hypomethylation intends a lower than normal level of DNA methylation. Methods of determining the level of DNA methylation are known in the art, some of which are described herein.

The term effective amount refers to a concentration or amount of a reagent or composition, such as a composition as described herein, cell population or other agent, that is effective for producing an intended result, including cell growth and/or differentiation in vitro or in vivo, or for the treatment of a neurodegenerative condition as described herein. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

As used herein, the term chemically induced or chemically modified pluripotent stem (iPS) cell is intended to include an iPS treated with a small molecule such as isoxazole or isoxazole similar molecule.

The terms effective period (or time) and effective conditions refer to a period of time or other controllable conditions (e.g., temperature, humidity for in vitro methods), necessary or preferred for an agent or composition to achieve its intended result, e.g., the differentiation of cells to a pre-determined cell type.

"Embryoid bodies or EBs" are three-dimensional (3D) aggregates of embryonic stem cells formed during culture that facilitate subsequent differentiation. When grown in suspension culture, EBs cells form small aggregates of cells surrounded by an outer layer of visceral endoderm. Upon growth and differentiation, EBs develop into cystic embryoid bodies with fluid-filled cavities and an inner layer of ectoderm-like cells.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. "Differentially expressed" as applied to a gene or marker, refers to the differential production of the mRNA transcribed from the gene or the protein product encoded by the gene. A differentially expressed gene may be overexpressed or underexpressed (a.k.a. inhibited) as compared to the expression level of a normal, non-treated or control cell. In one aspect, it refers to overexpression that is 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher (i.e., and therefore overexpressed) or lower than the expression level detected in a control sample. The term "differentially expressed" also refers to nucleotide sequences in a cell or tissue which are expressed where silent in a control cell or not expressed where expressed in a control cell.

An "induced pluripotent cell" intends embryonic-like cells reprogrammed to the immature phenotype from adult cells. Various methods are known in the art, e.g., "A simple new way to induce pluripotency: Acid." Nature, 29 Jan. 2014 and available at sciencedaily.com/releases/2014/01/140129184445, last accessed on Feb. 5, 2014 and U.S. Patent Application Publication No. 2010/0041054. Human iPSCs also express stem cell markers and are capable of generating cells characteristic of all three germ layers.

"Isoxazole" is a class of compounds found in some natural products, such as ibotenic acid, as well as a number of drugs, including a COX-2 inhibitor, and furoxan, a nitric oxide donor. Isoxazoles are useful isosteres of pyridine, and have been found to inhibit voltage-gated sodium channels to control pain, enable the construction of tetracycline antibiotic derivatives, and as treatments for depression. Compounds of this class available from Sigma-Aldrich and methods to synthesize such are known in the art as described for example in U.S. Pat. Nos. 5,059,614 and 8,318,951 and PCT Publication No. WO 1999/002507. Structurally, isoxazole is a five membered heterocyclic compound containing oxygen and nitrogen atoms in the 1, 2 positions. Its partially saturated analogs are called isoxazolines and completely saturated analog is isoxazolidine. Examples of isoxazole-like compounds include derivatives, non-limiting examples of such include sulfamethoxazole, sulfisoxazole, oxacillin, cycloserine and acivicin. Isoxazoles, isoxazolines and isoxazolidines may be considered as useful synthons in organic synthesis. Isoxazoles may be efficiently transformed in to various classes of medicinally important molecules. For example, Anthracen-9-ylmethylene-(3,4-dimethylisoxazol-5-yl) amine may be synthesized in high yield by reaction of anthracene-9-carbaldehyde and 5-amino-3,4-dimethylisoxazole in ethanol. In an embodiment, all the derivatives of Isoxazole may be considered as "isoxazole-like compound" or "similar compound". In an embodiment, the Isoxazole derivatives such as 5-Amino-3-methyl-4-isoxazolecarboxylic acid semicarbazides and thiosemicarbazides may be synthesized. The reaction of 5-amino-3-methyl-4-isoxazolecarboxylic acid hydrazide with isocyanates and isothiocyanates may be designed and conducted. The isocyanates, in the reaction of nucleophilic addition with compounds containing the primary amino group, form urea derivatives and isothiocyanates the thiourea derivatives. Only the hydrazide terminal group (—NH2) participates in this reaction. The amino group in position 5 of isoxazole ring remains not reactive under the reaction conditions. The mechanism of the reaction consists in nucleophilic attack of the nitrogen atom in the hydrazide group (—NH2) on the carbon atom of isocyanate or isothiocyanate. The intermediate forms appear which undergo amidoiminole tautomerization leading to formation of substituted 5-amino-3-methyl-4-isoxazolecarboxylic acid semicarbazides and thiosemicarbazides. In an embodiment, examples of isoxazole derivatives may comprise 5-sulfanilamido-isoxazoles of the general formula wherein R and R are lower alkyl and/or lower alkoxy alkyl groups. Sulfanilamide derivatives with the isoxazole ring attached in 'N position of the sulfanilamide molecule may be generated. For example, sulfanilamide radical in 4-position of the isoxazole ring. Further, a sulfanilyl derivative of 5-amino-isoxazole namely, 5-sulfanilamido-3-methyl-isoxazole may also be considered as an isoxazole derivative. In an embodiment, both the 3- and 4-positions of the isoxazole ring of the sulfanilamide derivatives may be replaced by an alkyl and/or corresponding alkoxy alkyl radical to generate. Non-limiting examples of "isoxazole-like compound" or "similar compound" comprise 1,2-oxazole, 4-deuterio-1,2-oxazole, 1,2-oxazole;potassium, hydron;1,2-oxazole, 1-oxido-1,2-oxazol-1-ium, 1,2-oxazole;hydrobromide, 1,2-oxazole;hydrochloride, ethane;1,2-oxazole, potassium;1,2-oxazole;hydroxide, 1,2-oxazole;hydrate;hydrochloride, ethane;1,2-oxazole, 1,2-oxazole; cyanate, 2-oxido-1,2-oxazol-2-ium, carbon monoxide; chromium; 1,2-oxazole, ethane; 1,2-oxazole, ethane; 1,2-oxazole;propane, 1,2-oxazol-2- ium-2-sulfonate, carbonyl dichloride;1,2-oxazole, isocyanic acid;1,2-oxazole, ethoxyethane;1,2-oxazole, 2,2-dimethylpropane; ethane; 1,2-oxazole, ethane;methoxyethane; 1,2-oxazole, ethane;2-methylpropane;1,2-oxazole, 1,2-oxazole; urea, ethanol;1,2-oxazole, carbonic acid; 1,2-oxazole, 1,2-oxazol-1-ium-1-sulfonic acid, 1,2-oxazol-2-ium;iodide.

"Isoxazole 9" (ISX-9) is a small molecule inducer of adult neural stem cell differentiation both in vitro and in vivo (Schneider et al.). It has been shown to act through a calcium-activated signaling pathway dependent on myocyte-enhancer factor 2 (MEF2)-dependent gene expression (Schneider et al.; Petrik et al.). Compounds are also available from Sigma-Aldrich and StemCell Technologies. The molecular formula is $C_{11}H_{10}N_2O_2S$, and the chemical name is N-cyclopropyl-5-thiophen-2-yl-1,2-oxazole-3-carboxamide. The two dimensional structure is

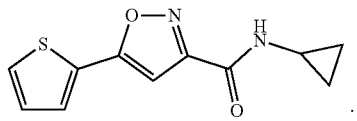 [SMILES: O=C(NC1CC1)c1cc(-c2cccs2)on1]

As used herein, the term "isoxazole-like compound" or "similar compound" intends an agent or small molecule that has the same functional property of the isoxazole as disclosed herein. Non-limiting examples include Cardionogen; CDNG1/vuc230, CDNG2/vuc198, and CDNG3/vuc247 (see Terri et al. (2011) Chem Biol., December 23 18(12): 1658-1668). Non-limiting examples further include sulfisoxazole as described herein below. Yet a further example is leflunomide (Arava), also known as 5-methyl-N-[4-(trifluoromethyl)phenyl]-1,2-oxazole-4-carboxamide.

"Sulfisoxazole" is a sulfonamide antibacterial with an oxazole substituent. It has antibiotic activity against a wide range of Gram-negative and Gram-positive organisms. Compounds of this class available from Sigma-Aldrich and methods to synthesize such are known in the art as described for example in U.S. Pat. No. 2,721,200. Non-limiting examples of sulfisoxazole include FDA approved drugs of AZO GANTRISIN, ERYTHROMYCIN ETHYLSUCCINATE and SULFISOXAZOLE ACETYL, ERYZOLE, GANTRISIN (with effective ingredients as SULFISOXAZOLE), GANTRISIN (with effective ingredients as SULFISOXAZOLE ACETYL), GANTRISIN (with effective ingredients as SULFISOXAZOLE ACETYL), GANTRISIN PEDIATRIC, ILOSONE SULFA, LIPO GANTRISIN, PEDIAZOLE, SOSOL, SOXAZOLE, SOXAZOLE, SULFISOXAZOLE, SULFISOXAZOLE DIOLAMINE, and SULSOXIN. (Drugs@FDA: FDA Approved Drug Products at the website of accessdata.fda.org).

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells or tissues that are isolated from other cells or tissues and is meant to encompass both cultured and engineered cells or tissues.

As used herein, the "lineage" of a cell defines the heredity of the cell, i.e. its predecessors and progeny. The lineage of a cell places the cell within a hereditary scheme of development and differentiation.

A "multi-lineage stem cell" or "multipotent stem cell" refers to a stem cell that reproduces itself (is self-renewing) and can differentiate to produce at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

A "parthenogenetic stem cell" refers to a stem cell arising from parthenogenetic activation of an egg. Methods of creating a parthenogenetic stem cell are known in the art. See, for example, Cibelli et al. (2002) Science 295(5556): 819 and Vrana et al. (2003) Proc. Natl. Acad. Sci. USA 100(Suppl. 1)11911-6.

The term "phenotype" refers to a description of an individual's trait or characteristic that is measurable and that is expressed only in a subset of individuals within a population. In one aspect of the invention, an individual's phenotype includes the phenotype of a single cell, a substantially homogeneous population of cells, a population of differentiated cells, or a tissue comprised of a population of cells.

As used herein, a "pluripotent stem cell" includes an Induced Pluripotent Stem Cell (iPSC) which is an artificially derived pluripotent stem cell made from a non-pluripotent cell, typically an adult somatic cell, that has historically been produced by inducing expression of one or more stem cell specific genes. Such stem cell specific genes include, but are not limited to, the family of octamer transcription factors, i.e. Oct-3/4; the family of Sox genes, i.e., Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e., OCT4, NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

A population of cells intends a collection of more than one cell that is identical (clonal) or non-identical in phenotype and/or genotype.

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of cardiac progenitor cells or cardiac cells.

ILS1 refers to an insulin gene enhancer protein, which plays an important role in regulating insulin gene expression. ISL1 is also found central to the development of pancreatic cell lineages and may also be required for motor neuron generation. ISL1 is identified as a marker for cardiac progenitor cells.

A "skeletal myoblast (SM)" is an immature cell that can be isolated from between the basal lamina and sarcolemma. They account for 2-5% of sub-laminar nuclei of mature skeletal muscle. Skeletal myoblasts are activated in response to muscle damage or disease-induced muscle degeneration. Skeletal myoblasts express desmin, CD56, Pax3, Pax7, c-met, myocyte nuclear factor, M-cadherin, VCAM1, N-CAM, CD34, Leu-19, and syndecan 3 and 4. Activated skeletal myoblasts first express Myf-5 and/or MyoD, and finally myogenin and MRF4 as the cells differentiate into multinucleated myotubes.

As used herein, the term "small juvenile stem cells (SJSCs)" intends stem cells isolated from aged bone marrow-derived stem cells (BMSCs) with high proliferation and differentiation potential. See Igura et al. (2013) 305(8): H1354-62. SJSCs express mesenchymal stem cell markers, CD29(+)/CD44(+)/CD59(+)/CD90(+), but are negative for CD45(−)/CD117(−) as examined by flow cytometry analysis. SJSCs show higher proliferation, colony formation, and differentiation abilities compared with BMSCs. They also are reported to significantly express cardiac lineage markers (Gata-4 and myocyte-specific enhancer factor 2C) and pluripotency markers (octamer-binding transcription factor 4, sex-determining region Y box 2, stage-specific embryonic antigen 1, and Nanog) as well as antiaging factors such as telomerase reverse transcriptase and sirtuin 1.

The term "stem cell" refers to a cell that is in an undifferentiated or partially differentiated state and has the capacity to self-renew and to generate differentiated progeny. Self-renewal is defined as the capability of a stem cell to proliferate and give rise to more such stem cells, while maintaining its developmental potential (i.e., totipotent, pluripotent, multipotent, etc.). The term "somatic stem cell" is used herein to refer to any stem cell derived from non-embryonic tissue, including juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells (MSCs) and neural stem cells (NSCs). An embryonic stem cell is a primitive (undifferentiated) cell from the embryo that has the potential to become a wide variety of specialized cell types (e.g., is pluripotent). Non-limiting examples of embryonic stem cells are the HES2 (also known as ES02) cell line available from ESI, Singapore and the H1 or H9 (also known as WA01) cell line available from WiCell, Madison, Wis. Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4.

A "marrow stromal cell" also referred to as "a bone marrow stromal cell" or a "mesenchymal stromal cell" is a multipotent stem cell that can differentiate into a variety of cell types. Cell types that MSCs have been shown to differentiate into in vitro or in vivo include osteoblasts, chondrocytes, myocytes, and adipocytes. Mesenchyme is embryonic connective tissue that is derived from the mesoderm and that differentiates into hematopoietic and connective tissue, whereas MSCs do not differentiate into hematopoietic cells. Stromal cells are connective tissue cells that form the supportive structure in which the functional cells of the tissue reside. While this is an accurate description for one function of MSCs, the term fails to convey the relatively recently-discovered roles of MSCs in repair of tissue. Methods to isolate such cells, propagate and differentiate such cells are known in the technical and patent literature, e.g., U.S. Patent Application Publication Nos. 2007/0224171, 2007/0054399, 2009/0010895, which are incorporated by reference in their entirety. In one embodiment, the bone marrow stromal cell has the phenotype CD34−/CD45−/CD105+/CD90+/CD73+. See also Dominici, M. et al. (2006) Cytotherapy 8(4):315-317, incorporated herein by reference.

Adipose stem cells are also known as adipose tissue-derived stem cells (ADSC) that are routinely isolated from the stromal vascular fraction (SVF) of homogenized adipose tissue. Similar to other types of mesenchymal stem cells (MSC), ADSC remain difficult to define due to the lack of definitive cellular markers. Adipose-derived stem cells (ASCs) are a mesenchymal stem cell source with self-renewal property and multipotential differentiation.

Hematopoietic stem cells are defined as a stem cell that gives rise to all red and white blood cells and platelets. They are commonly isolated by use of the markers CD34+. In another aspect, the hematopoietic stem cell is an adult stem cell comprising the marker profile of: $CD34^+$ and/or $CD34^+$/$Thy-1^-$ HSC). See also Andrews, R. G. et al. (1990) J. Exp. Med. 172(1):355-358, incorporated herein by reference.

Mesenchymal stem cells, or MSCs, are defined as multipotent stromal cells that can differentiate into a variety of cell types, including: osteoblasts (bone cells), chondrocytes (cartilage cells), myocytes (muscle cells) and adipocytes (fat cells).

A "subject," "individual" or "patient" is used interchangeably herein, and refers to a vertebrate, preferably a mammal, more preferably a human. Mammals include, but are not limited to, murines, rats, simians, bovines, canines, felines, humans, farm animals, sport animals and pets.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., cardiac arrhythmia. As is understood by those skilled in the art, "treatment" can include systemic amelioration of the symptoms associated with the pathology and/or a delay in onset of symptoms such as chest pain. Clinical and subclinical evidence of "treatment" will vary with the pathology, the individual and the treatment.

A juvenile or young stem cells intends from 2 months or younger mice possessing antiaging genes. In vitro, the cells average from about 3-5 µm in size and express the embryonic stem cell marker, OCT4 and surface markers, CD29, CD44, CD90.

Gαi is a heterotrimeric G protein subunit that inhibits the product of cAMP from ATP. An exemplary sequence is provided under GenBank Ref.: NM_002069 and UnProt P63096. Antibodies that recognize this marker are commercially available from Santa Cruz Biotechnology.

miR-133 refers to a microRNA that has been linked to an immature or undifferentiated phenotype. Methods to detect such include, for example, microarray-RT-PCR and RNA-seq. Commercially available kits to miR-133 is available from EMD Millipore (SmartFlare™ Detection Probes) which allow for the detection of miRNA in live cells.

miR-762 is a non-coding RNA that has been linked to post-transcriptional regulation of gene expression in multicellular organisms. The miR-762 human sequence is reported under Accession No. MI0003892 (last accessed on Apr. 16, 2014). The murine sequence is reported under NR_030428.1 (see ncbi.nlm.nih.gov/gene/79103, last accessed on Apr. 16, 2014). Methods to detect such are known in the art and kits are commercially available from, for example, Origene (miR-762, see origene.com, last accessed on Apr. 16, 2014).

miR-195 is an RNA gene, and is reported to be affiliated with the miRNA class. Diseases associated with miR-195 include tongue squamous cell carcinoma and primary peritoneal carcinoma. Among its related pathways are microRNAs in cancer and microRNAs in cardiomyocyte hypertrophy. It is also known as MIRN195, Has-MIR-195 and MiRNA 195. The sequence and homologs are reported in the GeneCards web page. Nucleic acid sequences are reported under GenBank Accession No. AK098506, last accessed on Nov. 18, 2015.

Tbx-5 is a cardiac transcription factor, also known as T-box transcription factor ("TBX5") is a protein that in humans is encoded by the TBX5 gene. As indicated on the GeneCards human gene database, this gene is a member of a phylogenetically conserved family of genes that share a common DNA-binding domain, the T-box. T-box genes encode transcription factors involved in the regulation of developmental processes. This gene is closely linked to related family member T-box 3 (ulnar mammary syndrome) on human chromosome 12. The encoded protein may play a role in heart development and specification of limb identity. Mutations in this gene have been associated with Holt-Oram syndrome, a developmental disorder affecting the heart and upper limbs. Several transcript variants encoding different isoforms have been described for this gene. The accession for the protein is Q99593 or alternatively A6ND77, or alternatively O15301, or alternatively Q96TBO. /antibodies to the protein are commercially available from R&D Systems, Browse EMD, OriGene Antibodies, and Novus Biologicals.

As used herein, the term "pluripotent gene or marker" intends an expressed gene or protein that has been correlated with an immature or undifferentiated phenotype, e.g., Oct¾, Sox2, Nanog, c-Myc and LIN-28. Methods to identify such are known in the art and systems to identify such are commercially available from, for example, EMD Millipore (MILLIPLEX® Map Kit).

The miR-290-295 cluster is a pluripotent cluster that codes for a family of microRNAs (miRNAs) that are expressed de novo during early embryogenesis and are specific for mouse embryonic stem cells (ESC) and embryonic carcinoma cells (ECC). Such are known in the art and described, for example, in Lichner et al. (2011) Differentiation, January 81(1):11-24.

Chemokine (C-C motif) ligand 7 (CCL7) is a small cytokine previously known as monocyte-specific chemokine 3 (MCP3). The protein sequence is available under Accession number NP_006264 and the murine sequence is available under NP_038682 (see also ncbi.nlm.nih.gov/gene/6354, last accessed on Apr. 16, 2014). An antibody and kit to detect CCL7 is available from Sino Biological Inc.

CXCR2 chemokine receptor 2 (CXCR2) is a protein encoded by this gene is a member of the G-protein-coupled receptor family. This protein is a receptor for interleukin 8 (IL8). It binds to IL8 with high affinity, and transduces the signal through a G-protein activated second messenger system. This receptor also binds to chemokine (C-X-C motif) ligand 1 (CXCL1/MGSA). Information regarding the protein and its gene is found on nchbi.nlm.nih.gov/gene/3579 (last accessed on Apr. 16, 2014).

Integral membrane protein 2A is a stem cell marker. The sequence of the human gene is reported at UniProtKB (O43736) and the murine sequence is reported at Q61500 (uniprot.org/uniprot, last accessed on Apr. 16, 2014).

DNA (cytosine-5)-methyltransferase 1 is an enzyme that is encoded by the DNMT1 gene. The complete sequence of the protein and its gene is available at genecards.org/cgi-bin/carddisp.pl?gene=DNMT1, last accessed on Apr. 16, 2014. Antibodies to detect the protein are commercially available, e.g., from Cell Signaling Technologies (DNMT1 (D63A6) XP® Rabbit mAb #5032). DNA (cytosine-5)-methyltransferase 3 is an enzyme that is encoded by the DNMT3 gene.

EFNA3 or ephrin A3 is a protein receptor. The human protein sequence is reported at ncbi.nlm.nih.gov/gene/1944. Antibodies useful for the detection and analysis of the protein are available from R&D Systems and Santa Cruz Biotechnology.

"Let-7" refers to a family of microRNAs. The sequences are reported at the miRBase at mirbase.org/cgi-bin/mirna_summary.pl?fam=MIPF000002, last accessed on Apr. 16, 2014. Methods for detecting such are known in the art, e.g., U.S. Patent Application Publication No. 2014/0005251.

Max is a pluripotency marker that binds MYC. See Chappell et al. (2013) Genes & Dev. 27:725-733.

Descriptive Embodiments

Induced Pluripotent Stem Cells

This disclosure provides an induced pluripotent stem cell (iPSC) characterized by DNA hypomethylation. In one aspect, the cell is additionally characterized by overexpression of one or more cardiac gene or marker selected from the group of Gαi, mir-133, mir-762, CCL7, CXCR2, CXC5, integral membrane protein 2A, and ephrin A3. Nkx-2.5, ISL1, GATA4, Sarcomeric actin, Gαi, mir-133, mir-762, CCL7, CXCR2, CXC5, integral membrane protein 2A, and ephrin A3. In another aspect, the cell under expresses one or more pluripotent genes or markers, non-limiting examples of such include one or more of miR-290-295 cluster, let-7 family, Max and under expresses one or more DNA methyltransferase genes Dnmt1, Dnmt3b. In one aspect, the one or more cardiac gene or marker is Gαi. In one aspect, the one or more cardiac gene or marker is overexpressed at least 1.5 fold, or alternatively at least 2 fold, or alternatively at least 3 fold, over that of a control cell. In another aspect, the cell is characterized by underexpression of one or more other cardiac gene or marker selected from the group of miR-290 cluster, miR-574-5P, let-7 family, Dnmt1, Dnmt3b, and Max. In one aspect, the one or more cardiac gene or marker is not expressed or underexpressed by at least 1.5 fold, or alternatively at least 2 fold, or alternatively at least 3 fold, under that of a control cell. Methods to identify and quantitate genes and markers are known in the art and described herein to supplement well known methods.

The cell can be from any animal species, such as a mammal, e.g., an equine, a murine, a bovine, a canine, a feline, or a human patient.

The iPS cell is derived from any suitable parent cell. Non-limiting examples of such include, without limitation, a cell selected from the group consisting of a bone marrow cell, a myoblast, a skin fibroblast, a cord blood cell, an adult peripheral blood, a cardiac progenitor cell, a small juvenile stem cell (SJST), a marrow stromal cell, a mesenchymal stem cell, a hematopoietic stem cell, or a mononuclear cell.

Methods to derive or prepare an iPSC from these parent cell types are known in the art. In one aspect, the iPSC was created by a method comprising contacting the parent cell with an effective amount of a DNA methyltransferase inhibitor to upregulate Oct4. Non-limiting examples of DNA methyltransferase inhibitors include 5'-azacytidine, 5-aza-2'-deoxycytidine, MG98, zebularine and RG108. In another aspect, the iPS cell was created by a method that excludes the insertion of exogenous genes into the parent cell.

In a yet further embodiment, the parent cells are progenitor cells, e.g., cardiac progenitor cells, prepared by preconditioning the cells with electrical stimulation. In one aspect, the parent cell is a stem cell that expresses Sca 1 and pluripotency and cardiac genes as described herein. The cells are subsequently contacted with isoxazole or an isoxazole similar compound as described herein.

In one aspect, the parent cell is a small juvenile stem cell or young stem cell that is not modified or programmed to an iPSC. In this aspect, the SJST is treated with the isoxazole or isoxazole similar compound and used diagnostically, in research or therapeutically. In another aspect, the disclosure provides a method to direct an immature or progenitor cell, e.g., a SJST cell, a circulating blood or heart derived stem cell) to a cardiac progenitor phenotype by contacting the cell with an effective amount of an isoxazole or isoxazole similar compound as described herein. In another aspect, the parent cells are juvenile or young stem cells that can be identified by low expression of miR-195 as compared to a cell that does not express the characteristics of a young or juvenile cell as described herein. In a further aspect, the parent cell is further characterized by low expression of one or more marker selected from miR-29b, miR-205, miR-378, and miR-542-3p as compared to a cell that does not express the characteristics of a young or juvenile cell as described herein. In a further or alternative aspect, the parent cell has been pre-conditioned with an effective amount of electrical stimulation. In another aspect, isoxazole or isoxazole similar compound is injected therapeutically in the ischemic heart where BMSC, skeletal myoblasts, peripheral blood-derived endothelial progenitor cells (EPC), resident cardiac stem/progenitor cells and fibroblasts are mobilized to the injury area by the art described (Konoplyannikov M1, Haider K H, Lai V K, Ahmed R P, Jiang S, Ashraf M Activation of diverse signaling pathways by ex-vivo delivery of multiple cytokines for myocardial repair. Stem Cells Dev. 2013 Jan. 15; 22(2):204-15) prior to treatment for maximum drug contact to induce regeneration.

The chemically modified iPS cell as described herein is prepared by contacting the cell with an effective amount of an isoxazole or isoxazole similar compound, e.g., an amount that is selected from the group of from about 0.3 to about 30 µM; from about 0.5 to about 25 µM; from about 12 to about 25 µM and from about 0.5 µM to about 20 µM. See also FIG. 14C.

While methods to prepare an iPS cell are known in the art, Applicant has determined that an iPS cell created by a method comprising contacting a parent cell with an effective amount of a DNA methyltransferase inhibitor, e.g., 5'-azacytidine or RG108 (Sigma-Aldrich) to upregulate Oct4 is particularly useful. In one aspect, the iPS cells are additionally prepared by a method that excludes the insertion of exogenous genes into the parent cell thereby enhancing the safety of the cells for clinical use. In another aspect, the cells are modified to an iPS cell by insertion of genes and other factors known in the art.

This disclosure also provides a population of cultured cells as described herein, by culturing the chemically modified cells to expand the cells as described herein. In one aspect the population is substantially homogenous, e.g., at least 70% identical in phenotype, or alternatively at least 75% identical in phenotype, or alternatively at least 80% identical in phenotype, or alternatively at least 85% identical in phenotype, or alternatively at least 90% identical in phenotype, or alternatively at least 95% identical in phenotype, or alternatively at least 98% identical in phenotype or alternatively, a clonal population of cells. In one aspect, the population is a clonal population. In one aspect, the cells are cultured under conditions that favor differentiation into a particular cell type, e.g., a cardiac cell. These culturing conditions are known in the art.

The cells and populations of cells can be further modified for therapeutic or research use, for by example, further comprising a detectable label or exogenous polynucleotide or polypeptide. Methods and appropriate polynucleotides for therapeutic use are described in Durrani et al. (2010) Regen. Med. 5(6):919-932.

Method for Preparing the Cells

This disclosure also provides a method for preparing a cardiac lineage cell from a stem cell, comprising contacting the stem cell with an effective amount of an isoxazole or isoxazole similar compound. Stem cells useful in the method includes, without limitation, a one or more of an iPS cell, such as an iPS cell derived from a bone marrow cell, bone marrow stromal cell, a mesenchymal stem cell, a hematopoietic stem cell, a myoblast, a skin fibroblast, a cord blood cell, an adult peripheral blood, a SJSC, a cardiac progenitor cell, or mononuclear cell. Methods to derive or prepare an iPSC from these parent cell types are known in the art. The cells prepared by this method are characterized in overexpressing one or more cardiac gene or marker, e.g., Nkx-2.5, ISL1, Tbx-5, GATA4, αMHC, Sarcomeric actin, Gαi, miR-133, miR-762, CCL7, CXCR2, CXC5, integral membrane protein 2A, or ephrin A3 and/or underexpressing one or more cardiac gene or marker, e.g., miR-290-295 cluster, let-7 family, Dnmt1, Dnmt3b, and Max, each as compared to a control cell such as a cell that has not been contacted with or exposed to the isoxazole or isoxazole similar compound. In one aspect, the over- or under-expression is at least 1.5 fold over- or under-that of the control cell.

In one aspect, the cell is a small juvenile stem cell (SJSC) that is not modified or programmed to an iPSC. In this aspect, the SJST is treated with the isoxazole or isoxazole similar compound and used diagnostically, in research or therapeutically. In another aspect, the disclosure provides a method to direct an immature or progenitor cell, e.g., a SJST cell, (contained with a population of circulating blood or heart derived stem cells) to a cardiac progenitor phenotype by contacting the cell with an effective amount of an isoxazole or isoxazole similar compound as described herein. An effective amount of electrical stimulation can be applied to the cell or tissue in need of the treatment, alone or in combination with the isoxazole or isoxazole similar compound. In another aspect, the parental cell is selected for chemical modification because it is characterized by low expression of miR-195 and the cell may or may not be pre-condition by application of an effective amount electrical stimulation.

In a particular aspect, the method comprises, or alternatively consists essentially of, or yet further consists of, contacting the cells with an effective amount of the isoxazole or isoxazole similar compound for at least 3 days, or alternatively at least 4 days, or alternatively at least 5 days, or alternatively at least 6 days, or alternatively at least 7 days, in DMEM F12 supplemented with from about 10% to about 30%, or alternatively 20% Knockout Serum Replacement (KSR; Invitrogen, USA), and from about 0.05 mM to about 0.2 mM, or about 0.1 mM MEM Non-Essential Amino Acids solution (Invitrogen, CA, USA), and from about 0.1 mM to about 0.3 mM or about 0.2 mM L-glutamine (Invitrogen, USA); and from about 0.05 mM to about 0.2 mM or alternatively from about 0.1 mM β-mercaptoethanol (Invitrogen, CA, USA); and from about 750 U/ml to about 1250 U/ml or alternatively from about 1000 U/ml LIF (Millipore); and an effective amount of 0.5% penicillin and streptomycin. The cells are then kept in the media without drug for five days. The media is changed every day otherwise due to increase in cell number the pH of the media get changed and effect the cell survival and gene expression. An effective amount of the isoxazole or isoxazole similar compound comprises, or alternatively consists essentially of, or yet further consists of from about 0.3 to about 30 μM; or from about 0.5 to about 25 μM; or from about 12 to about 25 μM; or from about 0.5 μM to about 20 μM. As used herein, isoxazole or isoxazole similar intends a class of compounds as described herein.

In another particular aspect, the method comprises, or alternatively consists essentially of, or yet further consists of, contacting the cells with an effective amount of the isoxazole or isoxazole similar compound for at least 3 days, or alternatively at least 4 days, or alternatively at least 5 days, or alternatively at least 6 days, or alternatively at least 7 days, in RPMI F12 without insulin. An effective amount of the isoxazole or isoxazole similar compound comprises, or alternatively consists essentially of, or yet further consists of from about 0.3 to about 30 μM; or from about 0.5 to about 25 μM; or from about 12 to about 25 μM; or from about 0.5 μM to about 20 μM. In yet another particular aspect, an isoxazole is an ISX-9 as described herein above. As used herein, isoxazole or isoxazole similar intends a class of compounds as described above.

The cells are then kept in RPMI F12 with insulin for another about 7-10 days to generate cardiomyocyte differentiation. The cells are then kept in EGM-2 medium (Lonza, Lonza Walkersville Inc., Walkersville Md. 21793-0127) for about 10 days to generate endothelial cell differentiation. The cells are kept in TGFβ (2 ng/ml) and PDGFBB (long/ml, R&D Systems, Inc, Minneapolis, Minn. 55413) about 10 days to generate smooth muscle cell differentiation.

Methods to identify and quantitate genes and markers are known in the art and described herein to supplement well known methods.

One can determine if the methods of this disclosure have been effective by molecular, clinical and other techniques. In one aspect, Nkx2.5, GATA4, Tbx5, ISL-1 and Mef2c upregulation is started after 3 days after contacting and expression of these markers can be determined by application histochemistry and/or PCR, as appropriate. Additional lineage identifying markers are shown in FIG. 14C. The cells can be further evaluated for 7 day treatment by qPCR. Immunofluorescence staining also showed that transcription factors (Nkx2.5, GATA4 and ISL-1) were highly expressed in hiPSC with 7 day small molecule treatment. The purity of Nkx2.5 positive cells in these small molecule treated cells by FACS was 96.5±2.5% cells. To establish that the Nkx2.5+ cells are truly committed cardiovascular precursors, Applicant found that these Nkx2.5+ cells were multipotent and directly differentiated into all three cardiovascular lineages, including CMs, ECs and SMCs in basal differentiation conditions without any specific induction signaling molecules with percentage of 95.2±2.1% CMs (TnT+), 90.3±2.5% ECs (CD31+) and 92.3±1.8% SMCs (α-SMA+). In addition, Applicant determined that the differentiated ECs exhibited phenotype and function similar to primary endothelial cells (ECs) (FIGS. 14A-14H)

The cell can be from any animal species, such as a mammal, e.g., an equine, a murine, a bovine, a canine, a feline, or a human patient. The cell can be autologous or allogeneic to the animal or patient being treated.

The contacting can be performed in vitro, e.g., in a tissue culture dish or plate as described herein or in vivo, by administering an effective amount of the isoxazole or isoxazole similar compound to a cell culture or in vivo by administering an effective amount of the compound or alternatively, compound and iPS cells to a patient or subject in need of such treatment. Methods for administering, systemically or locally, such are described below. The compounds and/or cells can be combined with a pharmaceutically acceptable carrier for ease of use. This treatment can, in one aspect, be combined with the administration of an effective amount of electrical stimulation to the tissue in need of such treatment. The electrical stimulation can be administered prior to, concurrently or subsequent to the administration of the isoxazole or isoxazole similar compound.

In one aspect, the stem cell contacted with the compound is an iPS cell. Methods to generate iPS cell from terminally differentiated cells are known in the art, e.g., by a method comprising contacting the parent cell with an effective amount of a DNA methyltransferase inhibitor, e.g., RG108 (Sigma-Aldrich) to upregulate Oct4. In another aspect, the iPS cell is created by a method that excludes the insertion of exogenous genes into the parent cell.

This disclosure also provides an isolated cell prepared by a method as described herein by further comprising isolating the cells. Yet further, the method further comprises culturing the cells to prepare a population of cells. In one aspect, the population is cultured under conditions to prepare a substantially homogenous, e.g., at least 70% identical in phenotype, or alternatively at least 75% identical in phenotype, or alternatively at least 80% identical in phenotype, or alternatively at least 85% identical in phenotype, or alternatively at least 90% identical in phenotype, or alternatively at least 95% identical in phenotype, or alternatively at least 98% identical in phenotype. In one aspect, the method further comprises culturing the cells under conditions that favor clonal expansion of the cells to a clonal population. In one aspect, the cells are cultured under conditions that favor differentiation into a particular cell type, e.g., a cardiac cell. These culturing conditions are known in the art.

The methods can be further modified by inserting into the cells and populations of cells a detectable label or exogenous polynucleotide or polypeptide. Methods and appropriate polynucleotides for therapeutic use are described in Durrani et al. (2010) Regen. Med. 5(6):919-932.

Compositions

This invention also provides compositions containing the cells, population of cells and/or differentiated cells in combination with a carrier, such as a biocompatible scaffold or a pharmaceutically acceptable carrier. In one embodiment, the composition is intended for therapeutic use and therefore, an effective amount of the modified cell, population of cells or differentiated cells are provided, alone or in combination with the isoxazole or isoxazole similar compound, in the composition.

Uses of the Cells and Cell Populations

Yet another embodiment of the invention is a method for restoring cardiac function in a tissue or host in need thereof. This and other therapeutic, diagnostic, and research uses are described herein.

In one embodiment, the invention provides methods for one or more of: regenerating cardiac muscle tissue that in one aspect, is scar tissue in the damaged or diseased heart; improving cardiac function or for treating a cardiac disease or condition in a patient in need thereof. The methods comprise contacting the tissue to be regenerated with an effective amount of isoxazole or isoxazole similar compound or by administering to a subject in need thereof, and/or an effective amount of the chemically modified cell or population of chemically modified cells described above. In a further aspect, the isolated cell, e.g., an iPS cell or other progenitor or stem cell is locally administered within an effective amount of isoxazole or isoxazole similar compound. In one aspect, the treated iPS cells were differentiated into myocytes forming myofibers in the scar tissue of the heart. The cells can be autologous or allogeneic to the host or patient. The subject and cells can be any species as described herein.

Yet another embodiment of the invention is a method for regenerating cardiac muscle tissue in a suitable host by administering to the host an effective amount of the chemically modified cell or population of chemically modified cells as described above. The cells can be autologous or allogeneic to the host or patient. The subject and cells can be any species as described above.

In another aspect, the method comprises, or alternatively consists essentially of, or yet further consists of administering to a patient in need thereof an effective amount of an iPS cell and an effective amount an isoxazole or isoxazole similar compound. Administration can be local to the site of damage, and can include direct injection of the cells and isoxazole or isoxazole similar compound into the heart of the patient. The method also includes combination therapy as described herein. For example, the method can be combined with an effective amount of electrical stimulation, before, after or concurrent to this therapy. The method can also be combined with an effective amount of other cardiac-inducing small molecules including:

1) Wnt/beta-catenin inhibitors, e.g., IWR-1, IWP-1. Include an FDA approved drug called Pyrvinium (common brand name is Vanquin). Another novel small molecule includes ICG-001(Chemical Name: (6S,9aS)-Hexahydro-6-[(4-hydroxyphenyl)methyl]-8-(1-naphthalenylmethyl)-4,7-dioxo-N-(phenylmethyl)-2H-pyrazino[1,2-a]pyrimidine-1(6H)-carboxamide) that targets the Wnt/β-catenin pathway.

2) TGF-β inhibitors, such as the small molecule ITD-1 defined as Chemical Name: 4-[1,1'-Biphenyl]-4-yl-1,4,5,6,7,8-hexahydro-2,7,7-trimethyl-5-oxo-3-quinolinecarboxylic acid ethyl ester).

3) Prostaglandins and COX-2. Activation of cyclooxygenase 2 (COX-2) and subsequent production of prostaglandin E2 (PGE2) induced by MI (PGE2 is an FDA-approved treatment for induction of labor under the brand name Dinoprostone. Another example includes small molecule ONO-1301—a small molecule agonist of PGI2 with a synymom of 7,8-Dihydro-5-[(E)-[[α-(3 pyridyl)benzylidene]aminooxy]ethyl]-1-naphthyloxy]acetic acid and supplied by Sigma-Aldrich.

4) DPP-IV inhibitors in combination with granulocyte colony stimulating factor or G-CSF. (This approach combines two molecules: a small molecule inhibitor of dipeptidylpeptidase IV (DPP-IV), an enzyme that degrades SDF-1α, and granulocyte colony-stimulating factor (G-CSF), a biological molecule that enhances the release of stem cells from the bone marrow through matrix metalloproteinase 2.

5) Angiotensin (1-7) and Mas receptor (formula: $C_{41}H_{62}N_{12}O_{11}$ and supplied by Tochris).

The combination therapy can be sequential or concurrent, as determined by the condition being treated, the health of the patient and the selection of the particular combination therapy.

In one aspect, the stem cells or iPS cells are administered in the form of a cardiac patch derived from stem cells (e.g., adult or bone marrow derived progenitors cells, iPS cells, iPS cells derived cardiac lineage cells, small juvenile stem cells and/or engineered tissue cardiac patch transplantation for the heart repair in heart diseases). Thus, in one aspect, the stem cells comprise very small juvenile stem cells that are present in the bone marrow (that are comprised within bone marrow stem cells) and/or peripheral blood cells (that are comprised within circulating blood and heart-derived stem cells). These cells are with significantly high proliferative and differentiation potentials and can also be easily reprogrammed and/or converted to cardiac progenitors with isoxazole or isoxazole similar compounds or Wnt inhibitors.

Thus, this method would not require the derivation of iPS cells for safe cell transplantation. This disclosure also provides a method for promoting stem cell survival and differentiation by applying cardiac patches with derivatives of iPS cells treated with isoxazole or isoxazole similar compounds and Wnt inhibitors administered over scar area allowing better penetration, migration and integration of patch cells (myocytes, endothelial cells, smooth muscle cells. (FIGS. 14A-14H) with host heart.

This disclosure also provides a method for promoting stem cell survival and differentiation in vitro, comprising applying an effective amount of electrical stimulation to the stem cell. In one aspect, the effective amount comprises wherein the electrical stimulation comprises from about 1.0V/1.5 cm to about 2.0V/2.0 cm for about 1 to about 5 hours.

This disclosure also provides a method for generating iPSC derived muscle progenitor cells (MPC) by isoxazole and isoxazole like compounds and their preconditioning or treatment of skeletal muscle that will induce functional CXCR4 expression in MPC to facilitate mobilization and engraftment of progenitor cells in dystrophic skeletal muscles. See FIGS. 15A-15B. For the MPC to be a viable therapeutic option for DMD, dystrophin gene expression must be sufficient to restore muscle contractility. Hence MPC from the disclosed methods provide an abundant source of cells for transplantation and provide an effective and safe therapy for regeneration of dystrophic muscle. Transplantation of iPSC-derived progenitors coupled with methods to optimize the host muscle microenvironment, such as treatment with an effective amount of a steroid will more effectively ameliorate dystrophic pathology and improve the quality of life for patients with DMD.

Patients suitably treated by this method include those suffering from a disease or disorder associated with cardiac malfunction including, but not limited to, congestive heart failure, isolated diastolic heart failure, myocardial infarction, and cardiac arrhythmia. There are several forms of cardiac arrhythmia that can be treated including, but not limited to, sick sinus syndrome, bradyarrhythmia, abnormal sinus node function, atrioventricular block, and atrial and ventricular tachyarrhythmia.

Local or systemic administration, by use of a catheter or cardiac patch with isoxazole or similar compound treated iPS cells, of the cells or compositions can be effected in one dose, continuously or intermittently throughout the course of treatment. Methods of determining the most effective means and dosage of administration are known to those of skill in the art and will vary with the composition and/or cells used for therapy, the purpose of the therapy and the subject being treated. Single or multiple administrations can be carried out with the dose level and pattern being selected by the treating physician. Suitable dosage formulations and methods of administering the cell or agents are known in the art. In a further aspect, the cells and composition of the invention can be administered in combination with other treatments.

The cells and populations of cell are administered to the host using methods known in the art and described, for example, in U.S. Pat. No. 6,638,369. This administration of the cells or compositions of the invention can be done to treat disease as noted herein, and to produce an animal model of the desired disease, disorder, or condition for experimental and screening assays.

Screening Assays

The present invention provides methods for screening various agents that modulate cardiac function. For the purposes of this invention, an "agent" is intended to include, but not be limited to a biological or chemical compound such as a simple or complex organic or inorganic molecule, a peptide, a protein (e.g., antibody), a polynucleotide (e.g., anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

To practice the screening method in vitro, suitable cell cultures or tissue cultures containing the modified cell(s) are first provided. When the agent is a composition other than a DNA or RNA, such as a small molecule as described above, the agent can be directly added to the cell culture or added to culture medium for addition. As is apparent to those skilled in the art, an "effective" a mount must be added which can be empirically determined. When agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

Also provided herein is a method for selecting a cell or cell population for reprogramming, comprising determining the expression level of miR-195 in a sample wherein low expression of miR-195 selects the cell or population and lack of low expression of miR-195 does not select the cell or population. In a further aspect, the method further comprises determining the expression level of one or more of marker selected from miR-29b, miR-205, miR-378, and miR-542-3p, wherein low expression of the one or more marker selects the cell or population and lack of low expression of miR-195 does not select the cell or population.

Exemplary Embodiments

Applicant has discovered that iPSc can be chemically induced to DNA hypomethylation causing upregulation of cardiac genes and allowing successful propagation in the diseased heart with no or limited chances for tumorgenicity.

Skeletal myoblasts (SMs) purified from young male Oct3/4-GFP$^+$ transgenic mouse were treated with DNA methyltransferase inhibitor 500 μM RG-108 in 0.5% DMSO in knock out DMEM for 5-days. Two weeks later, GFP$^+$ colonies of SM derived iPS cells (SiPS) expressing GFP and morphological features of mouse embryonic stem cells were isolated and propagated in vitro. SiPS were positive for alkaline phosphatase activity, expressed SSEA1 and displayed a panel of pluripotency markers (FIG. 1) similar to ES cells and developed teratomas in nude mice. Although the research described herein was conducted in a murine model, the use of the same markers and agents will provide similar if not identical results in human cells and tissue.

Figure 2:
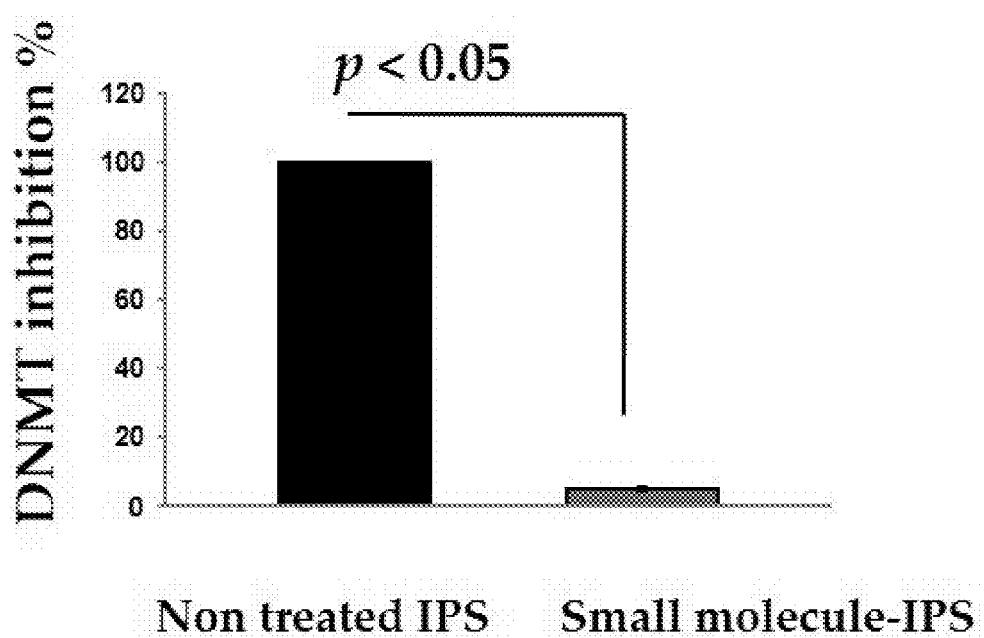
FIG. 2 shows the results of DNA methyltransferase (DNMT) activity assay. DNA methylation analysis showing significant (95%) inhibition of DNA methyltransferase activity in small molecule, isoxazole or isoxazole like compounds treated IPS cells in comparison to the nontreated IPS cells.
Figure 3A:
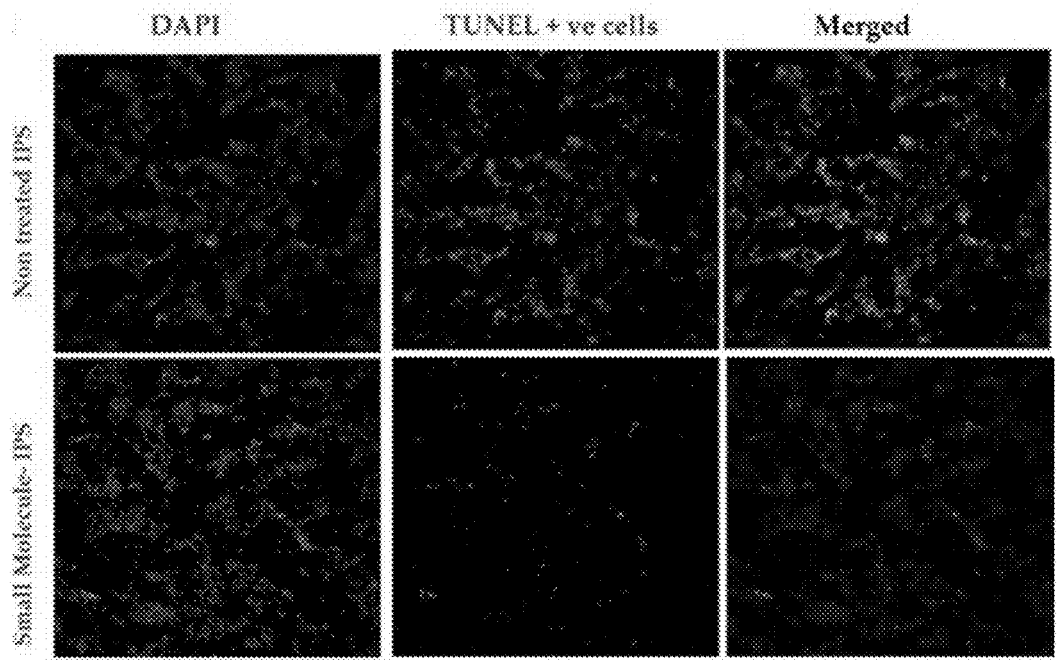
FIGS. 3A-3B show that small molecule, isoxazole or isoxazole like compounds treatment induces cytoprotection in vitro and that small molecule treatment prevents oxidant induced apoptosis and increases the proliferation.
Figure 3B:
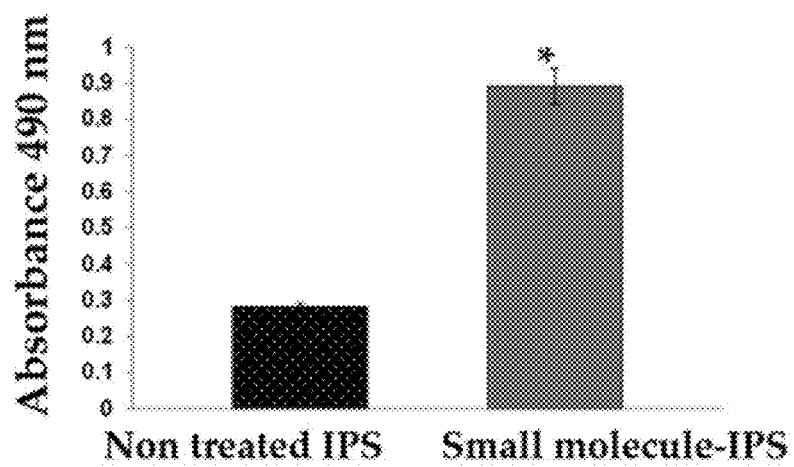
Figure 4:
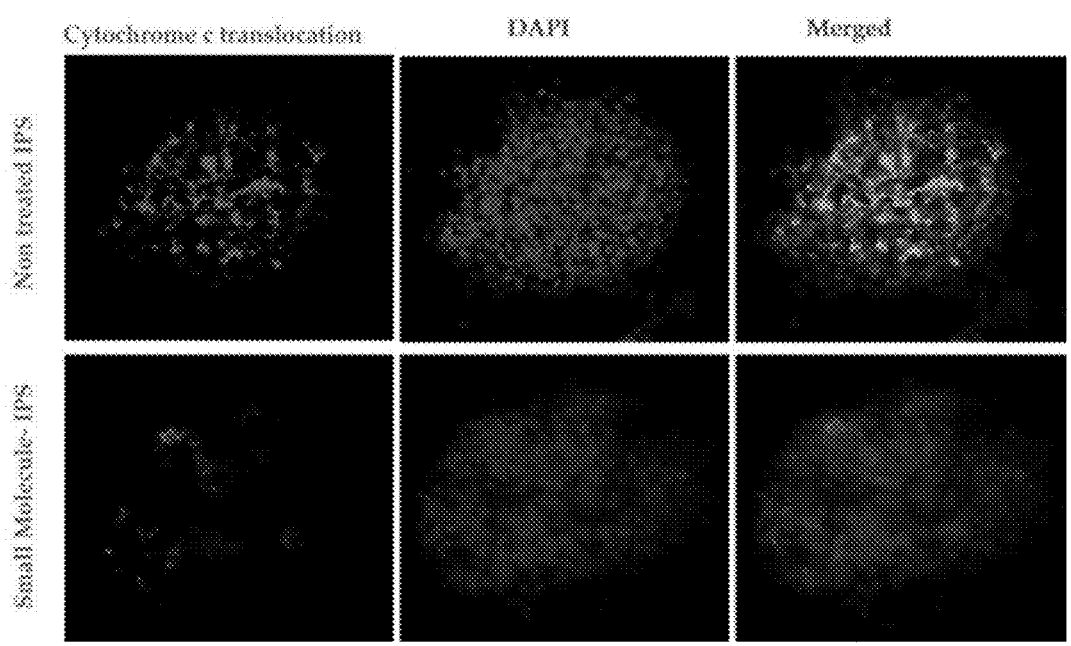
FIG. 4 shows cytochrome c translocation to cytoplasm (a sign of cell injury). Immunostaining of cytochrome c in non-treated and small molecule, isoxazole or isoxazole like compounds treated IPS cells after exposure to $H_2O_2$ (100 µmol), (merged images with DAPI), (original magnifications; 200×). Small molecule, isoxazole or isoxazole like compounds treated IPS cells show a significant decrease in cytochrome c translocation to cytoplasm as compared to the non-treated IPS cells.

In order to direct SiPS towards cardiac lineage cells, they were treated with a small molecule (Isoxazole, 20 uM, Sigma-Aldrich or ISX-9, StemCell Technologies, Inc Vancouver, BC) for five days and analyzed for DNA methyltransferase (Dnmt) activity, cell proliferation, and cardiac gene expression. DNMT activity was completely abolished with 95% reduction in global DNA methylation in small molecule treated SiPS (FIG. 2). These SiPS showed increased proliferative activity (p<0.01 vs. non treated Sips) evaluated by cell proliferation assay and also become tolerant to apoptosis (FIGS. 3A-3B) an important consideration for preventing cell death in the ischemic environment. Small molecule treated IPS cells show a significant decrease in cytochrome c translocation to cytoplasm as compared to the untreated IPS cells (FIG. 4).

Figure 5A:
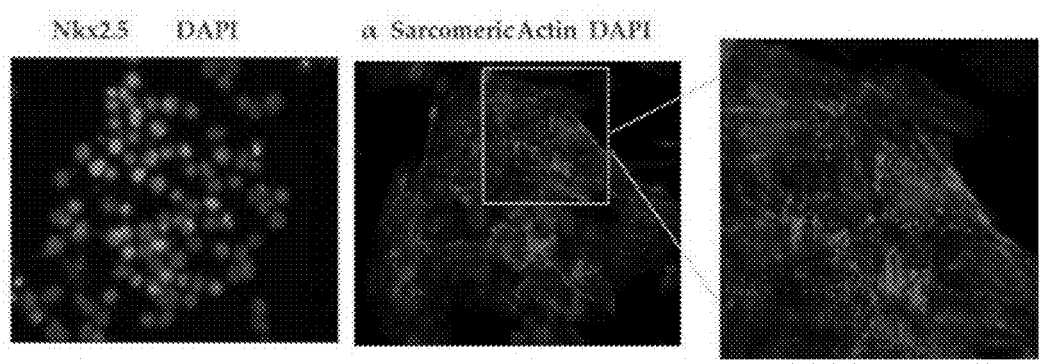
FIGS. 5A-5B show small molecule, isoxazole or isoxazole like compounds mediated cardiac differentiation of IPS cells in vitro.
Figure 5B:
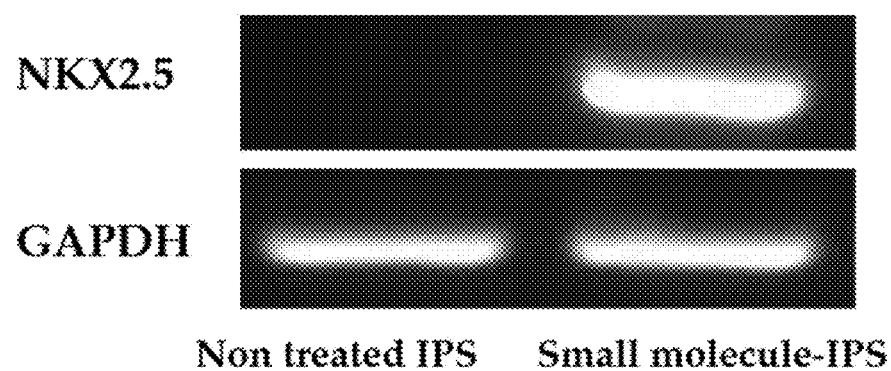
Figure 6:
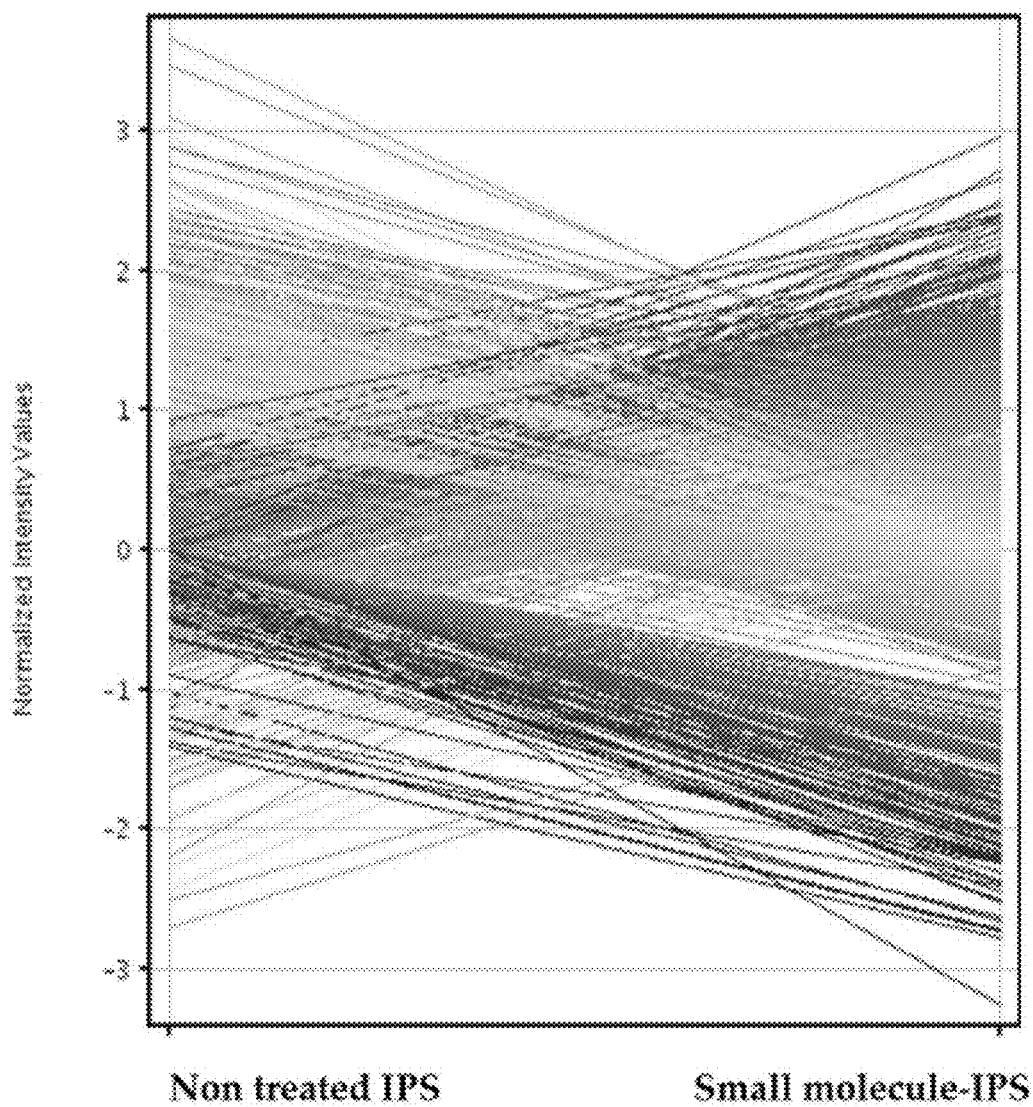
FIG. 6 shows small molecule, isoxazole or isoxazole like compounds treatment induces Global DNA hypomethylation by targeting G-protein coupled receptor (GPCR) signaling.
Figure 7E:
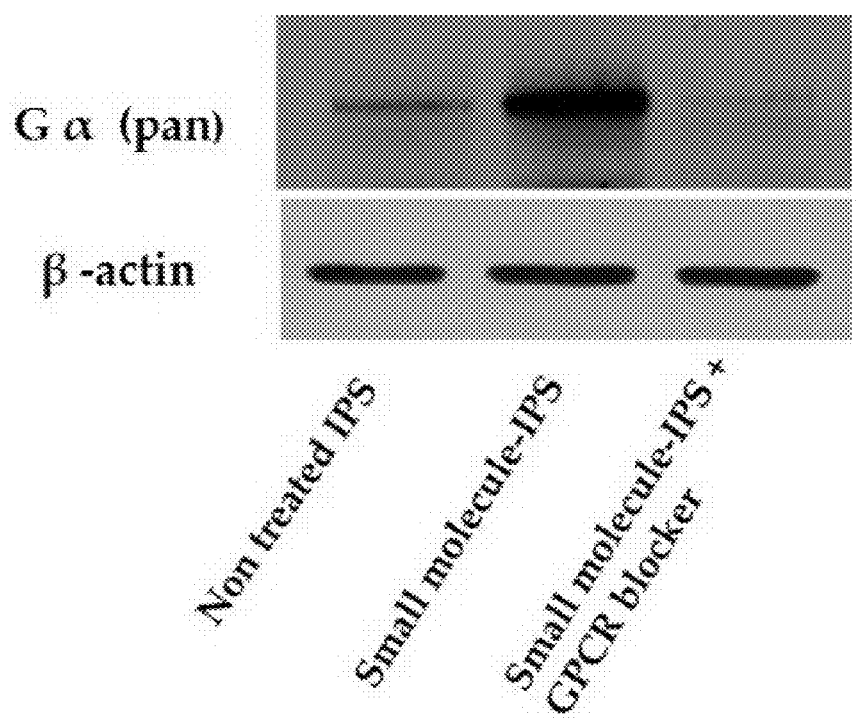

RT PCR analysis showed cardiomyocyte-like gene expression profile with significant upregulation of Nkx-2.5 (p<0.01 vs non treated IPS; see FIGS. 5A-5B). Approximately 60% treated iPS cells were positive for Nkx-2.5. Given that posttranscriptional regulation is crucial for gene expression and cell survival molecular phenotypic analysis was performed, Affymetrix array-based gene expression profiling further confirmed 2-3 folds downregulation of Dnmt1, Dnmt3b and Max gene associated protein which were associated with global DNA hypomethylation and myc dependent cell transformation (see Table 1). Additionally, there was a 2-3 fold concomitant upregulation in the CCL7, CXCR2, CXCR5, integral membrane protein 2A, and ephrin A3. (FIG. 6). These were associated with DNA synthesis, cell proliferation, cell matrix interaction and chemoattraction. miR microarray analysis showed upregulation of cardiac specific miR-133, 762 and down regulation of pluripotency associated miR-290 cluster, miR-574-5p and let-7 family (see FIGS. 7A-7D). Western blot analysis showed significant upregulation of Gαi protein levels as compared to untreated IPS cells (see FIG. 7E).

Figures 8A, 8B, 8C, 8D:
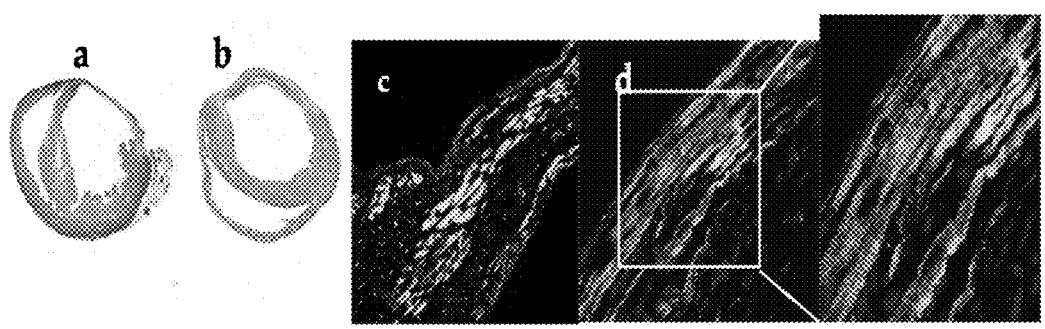
FIGS. 8A-8F show transplantation of iPS cell treated with isoxazole or isoxazole like compounds attenuated infarct size expansion and regeneration into fully developed myofibers in vivo. A total 3.6λ10^5 cells were injected per animal in the infarct and peri infarct regions after coronary artery ligation. The animals were sacrificed 7 days and 6 weeks after transplantation. A significant attenuation of infarct size and growth of new myocytes in scar tissue in hearts from transplanted animals (b) as compared to the control group (a) was observed. A significant regeneration of infracted heart with new fibers resulted in reduced infarct size. There were very limited number of iPS derived growing cells observed in hearts transplanted with non-treated iPS cells (not shown).
Figure 8E:
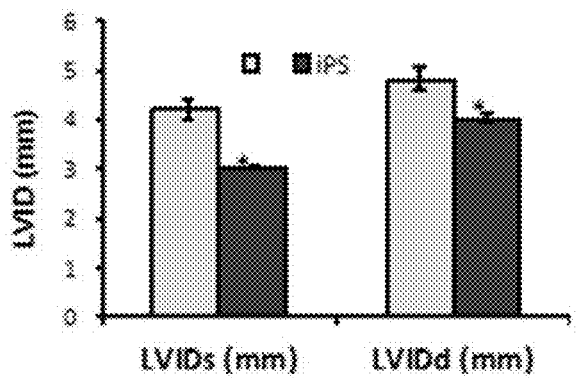

The SiPs treated with the small molecule were stained with PKH 26 for locating them in the heart and transplanted in the myocardium after 30 minutes of coronary artery ligation for 6 weeks. Before harvesting the hearts for visualizing the fate of transplanted SiPs, cardiac function was monitored with echocardiography. The treated SiPs were differentiated into myocytes forming myofibers in the scar tissue. The scar area in the left ventricle was muscularized with the treatment with ISX treated SiPS (FIGS. 8B, 8C, 8D) compared to untreated/control hearts (FIG. 8A) These are significant findings and have been reported previously in an initial patent application as only new pictures are graphically shown in figures (see FIGS. 8A-8F).

Figure 8F:
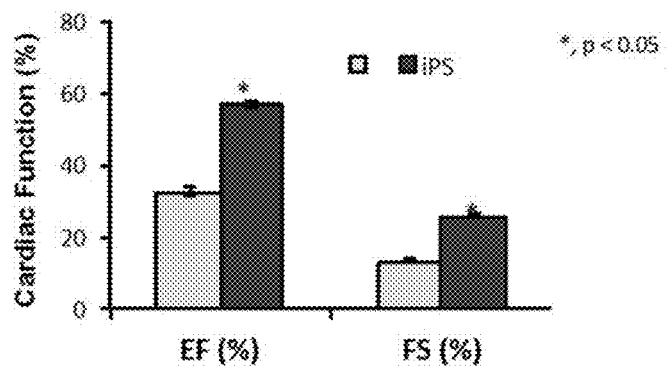
Figure 9A:
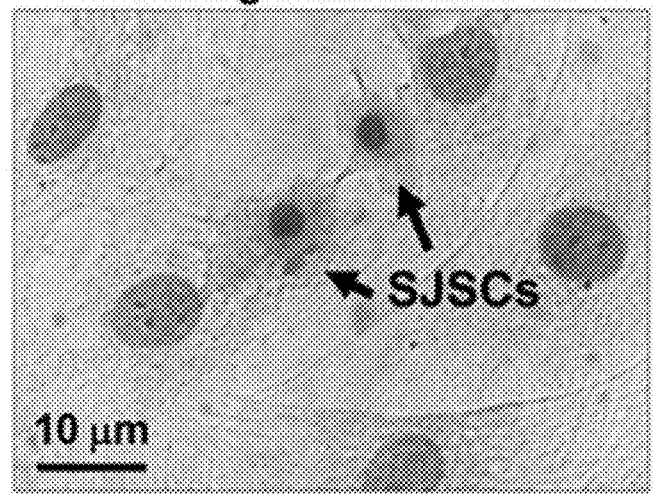
Figure 9B:
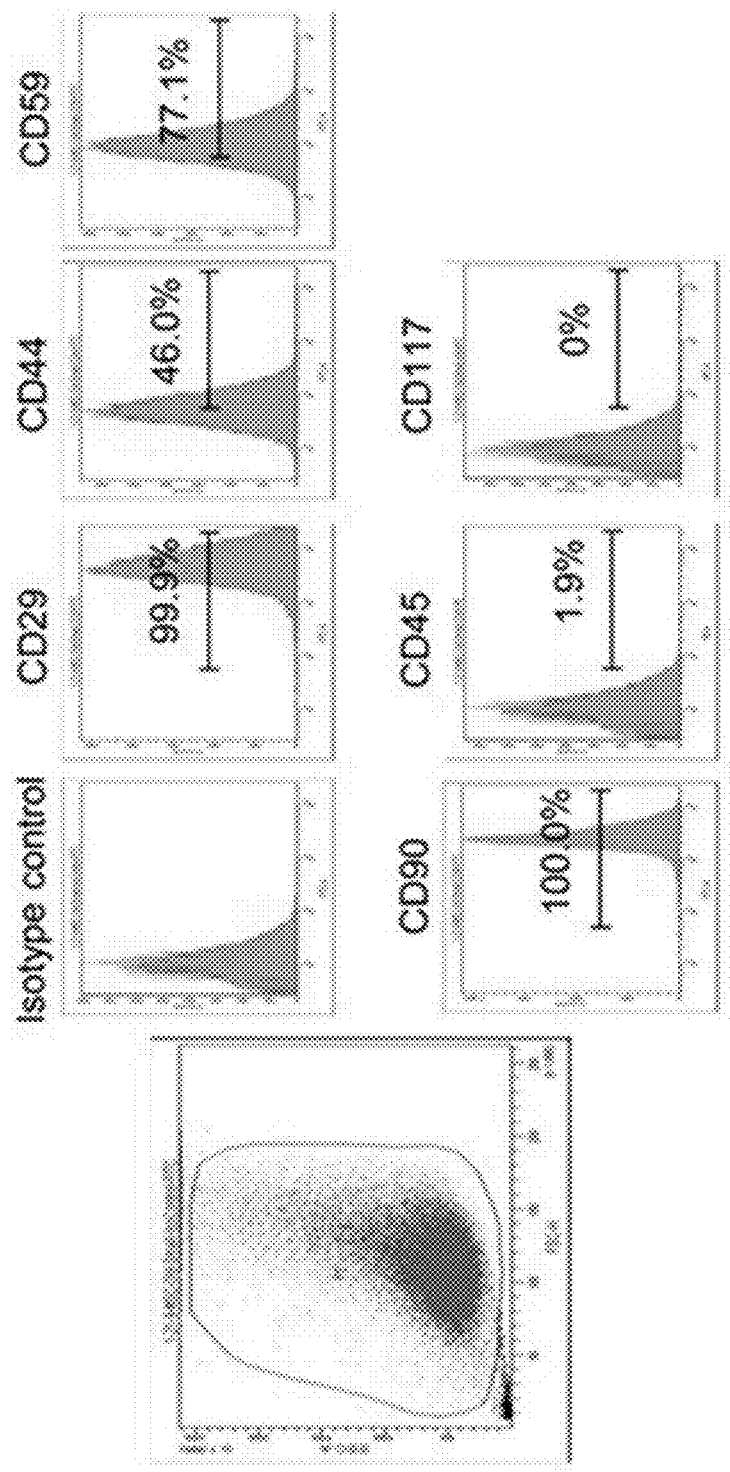
Figure 9C:
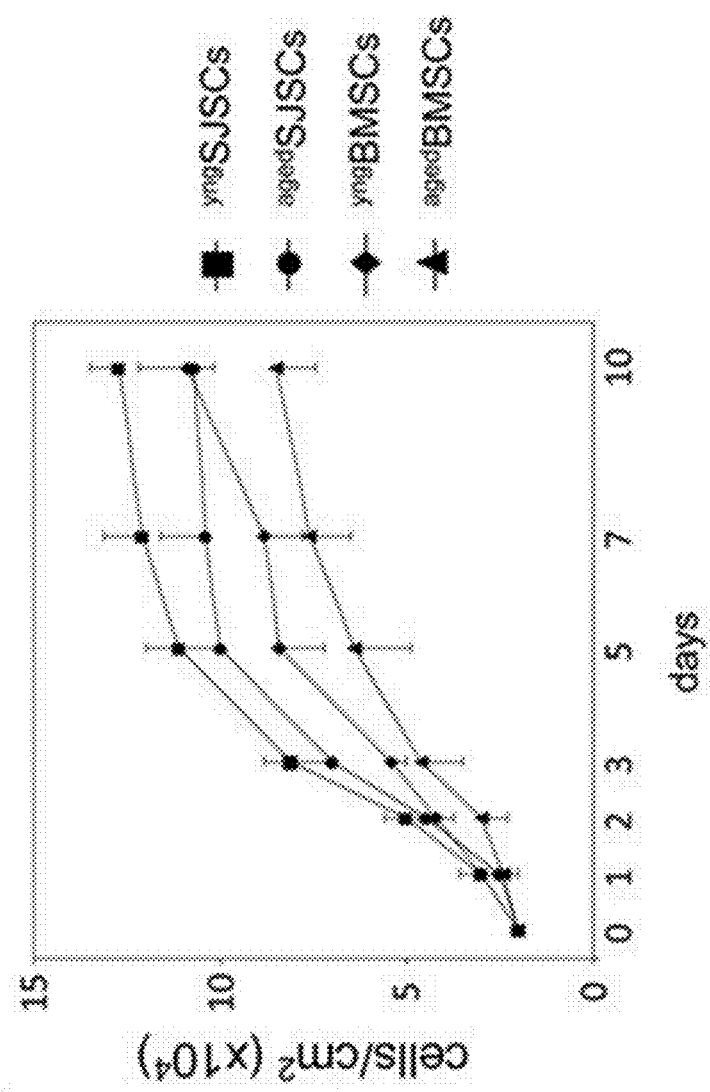
Figures 9D, 9E, 9F:
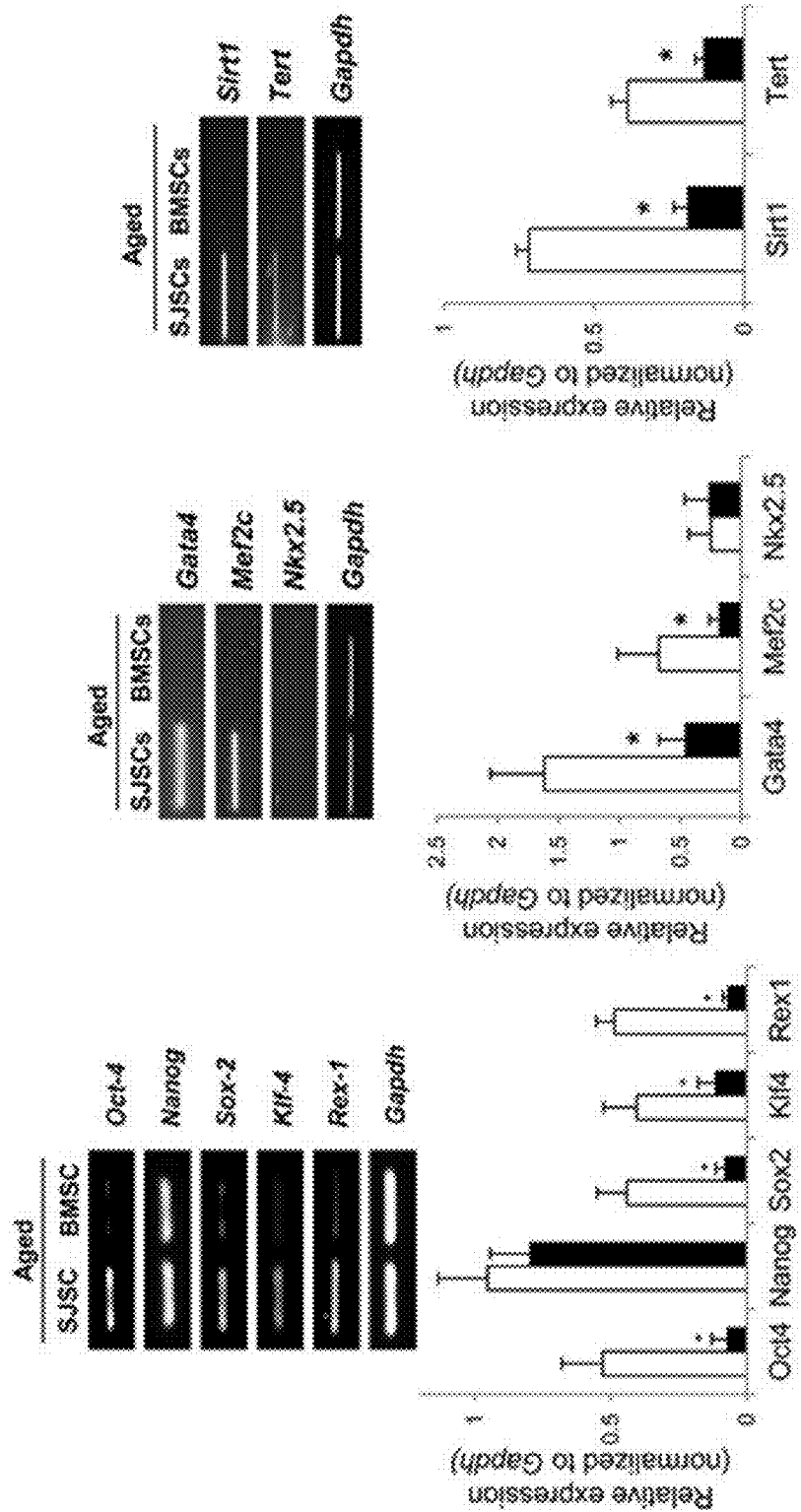
Figure 10A:
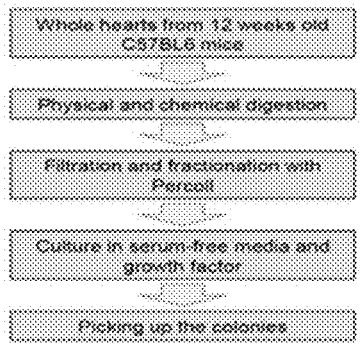
FIGS. 10A-10D show characterization of Sca-1$^+$ CSCs.
Figure 10B:
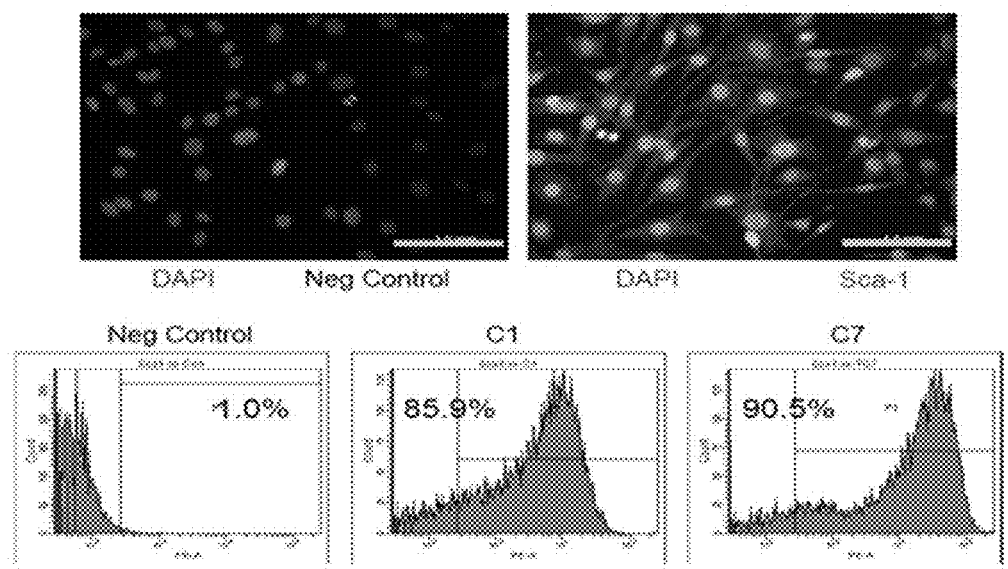
Figure 10C:
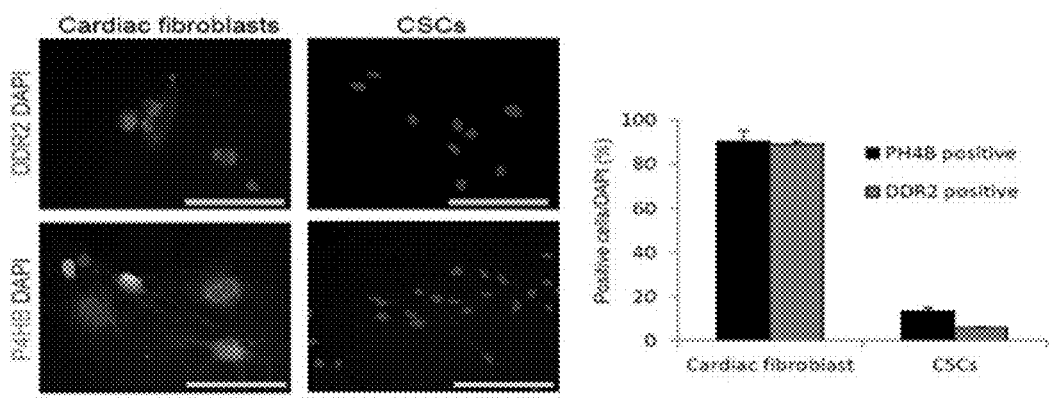
Figure 10D:
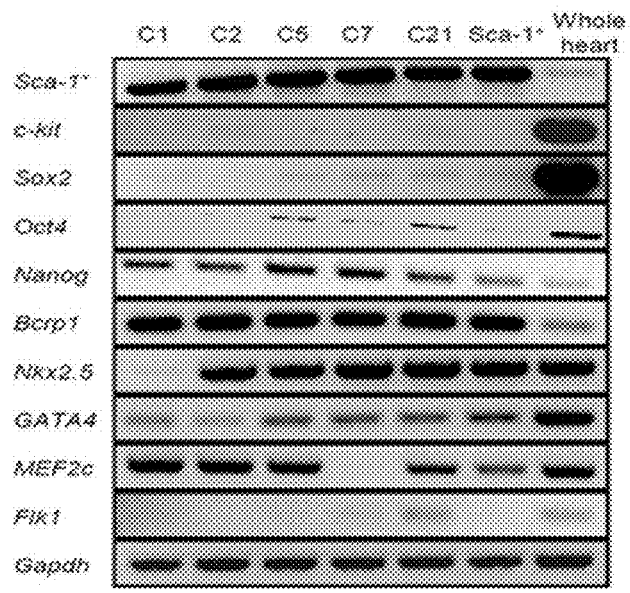

Cardiac function: The temporal changes in global heart function including left ventricle ejection fraction (LVEF) and left ventricle fractional shortening (LVFS) were measured in control infarcted and treated infarcted hearts. The pathological remodeling of left ventricle chamber dimensions during systole (LVDs) and diastole (LVDd) was also significantly reduced in CPs treated hearts (2.97 mm and 3.99 mm) as compared with DMEM treated hearts (4.77 mm- and 4.78). See FIG. 8E. Transplantation of CPs significantly improved LVEF and LVFS (56.8+−1.32%; 25.5+−0.4%) in comparison with the DMEM injected infarcted hearts (n=4; 32.42+−1.03% and 13.0+−0.4% respectively). FIG. 8F.

Applicant also discovered that isoxazoles induced DNA hypomethylation and myc dependent cell transformation in the iPS cells and were associated with DNA synthesis, cell proliferation, cell matrix interaction and chemotexis. The isoxazoles compound upregulated the CXC chemokine receptors and integral membrane proteins, Epherin family and related receptors that specifically involved in the development of erythropoiesis.

Applicant further discovered that isoxazoles upregulated cardiac specific miR-133, miR-762 and down regulation of pluripotency associated miR-290 cluster and let-7 family in iPS cells as compared to untreated iPS cells.

Thus, the above reports that small molecule-mediated modification of iPS cells can grow in the infarcted heart and replace the scar tissue with working myocytes coupled together with electrical connections (gap junctions). The sulfonyl-hydrazone family of small molecules can induce cardiac genes in iPS cells derived from myoblasts. These small molecules are known to induce muscle differentiation in Notch activated epicardium derived progenitors (Russell, J. L. et al. (2012) ACS Chem Biol. 7(6):1067-1076). Small molecule induced iPS cells were engrafted in post ischemic model and improved global cardiac function compared to non-treated iPS cells. Recovery of cardiac function was dependent on the survival of the iPS cell-derived progenitors cells. Small molecules are innovative in inducing the tissue-specific gene expression in iPS cell towards tissue differentiation, as well as determining the temporal and spatial patterns of development.

Applicant has discovered that the induced pluripotent stem cells, if treated with the appropriate small molecule, can pharmacologically inhibit the DNA methylation, hence a critical player in the regulation of cardiac developmental genes. Without being bound by theory, the effect of small molecule on epherin family may manipulate the process of hematopoietic progenitor generation and could be beneficial for clinical hematopoietic malignancies.

Applicant also discovered that isoxazoles upregulated cardiac specific miR-133, miR-762 and down regulation of pluripotency associated miR-290 cluster and let-7 family in iPS cells as compared to nontreated iPS cells.

Eric Oslon in U.S. Pat. No. 8,318,951 (951 patent) previously reported the use of these compounds in neurogenesis, epicardial progenitor cells. Regardless of these studies, the findings reported herein are unique and innovative in that the findings address the small molecule induced epigenetic changes that can be manipulated for rendering the iPS cells for propagation in the infarcted heart. This work emphasizes the iPS cells which can be made from a patient cell (in this case skeletal muscle) and reintroduced into the same patient after pretreatment with small molecule. These findings are distinct from the work of Oslon since iPS cells of the present disclosure were therapeutically predesigned (or pretreated) for propagation in the scar tissue of the mice heart after coronary artery ligation or heart attack. There was significant regeneration in the scar tissue by iPS cells. On the other hand, Olson injected the drug into live mice to act on heart progenitors present in the heart. It is Applicant's belief that the drug worked on different cells of the heart. Here, the composition and methods predesigned the iPS cells into cardiac progenitors in the dish and then reintroduced into damaged hearts.

Applicant also found that IPS pretreatment with small molecule reduced the apoptosis which is also novel finding. For example, less apoptosis was observed in small molecule induced iPS cells as compared to non-induced iPS cells. The results reported in the '951 patent were generated only using the Trypan blue exclusion assay for cell viability not cell apoptosis which is critical in cell survival under ischemic condition.

Applicant also found that DNA methyltransferase (DNMT) activity was completely abolished in the chemically modified IPS cells. There was 2-3 folds downregulation of Dnmt1, Dnmt3b and Max gene associated protein in small molecule modified iPS cells which are associated with DNA hypomethylation and cell transformation. There was 2-3 folds upregulation of CCL7, CXCR2, CXCR5, integral membrane protein 2A, and EphrinA3 which are associated with cell mobilization, chemotaxis, cancer and erythropoiesis was also observed. Applicant further observed upregulation of cardiogenic specific miR-133, miR-762 and down regulation of pluripotency markers and pluripotency associated miR-290-295 cluster and let-7 family which confirms the induction of the cardiac regulatory genes by Micro RNAs by down regulating the pluripotency genes.

In addition, the '951 patent didn't observe Gα protein level, as compared to the work reported here, which did observe the Gα protein level upregulation which was blocked when the chemically modified iPS cells were treated with GPCR blocker and abolished the all in vitro effect in small molecule induced iPS cells. Oslon previously has reported the use of these compounds in neurogenesis, epicardial progenitor cells. Regardless of the previous studies, it is Applicant's belief that the current findings are unique and innovative that address the small molecule induced epigenetic changes that can be manipulated for rendering the iPS cells suitable for propagation in the infracted heart. Another novelty is shown here that initially iPS cells primed with isoxazoles and similar small molecules can be converted into vascular (endothelial) progenitors and smooth muscle cells as well besides myocytes.

To the best of Applicant's knowledge and the results reported in Example 2, below, that isoxazoles and other similar small molecules work on other stem cells from the body. For example, stem cells derived from the bone marrow and the heart can be directly reprogrammed into myoctyes or endothelial cells and smooth muscles with small molecule drugs like isoxazoles. Thus, isoxazoles and similar small molecules can be directly administered, e.g., by injection into the hearts of patients, e.g., heart attack patients, for converting inflammatory cells and stem cells mobilized to the ischemic sites into cardiac cells in order to replace the scar tissue. The net effect is to assist with the regrowth of the damaged heart after the heart attack. The disclosed methods have the advantage of being non-viral based, using a previously approved compound, that simplifies clinical adoptions. Moreover, it is Applicant's belief that the disclosed methods will dramatically increase cardiac progenitors in one step treatment of iPSC in mono layer without converting them into embryoid bodies within a few short weeks after treating with isoxazoles or other similar small molecules like cardionogin; CDNG1/vuc230, CDNG2/vuc198, and CDNG3/vuc247.

Current approaches in using iPS cells include limitations such as genetic mutations and or tumor (i.e., cancer) growth versus Applicant's methods, approach and technique. The methods are beneficial in that genetic mutations are not necessary, improving safety for clinical use.

It is Applicant's belief and to the best of his knowledge, the current reported study provides the first evidence that iPS cells can be therapeutically rendered safe for use by altering their chromatin configuration for upregulation of cardiac genes. These so called cardiac progenitors can propagate and regenerate the dying myocardium with limited cell death. Chemical reprogramming iPS cells to desired cardiac lineage would be smart strategy in cardiac therapeutics.

EXPERIMENTAL METHODS

Experiment No. 1

Maintenance of Mouse SiPS

SiPS were maintained on mitomycin C-treated mouse embryonic fibroblasts (MEFs) dishes in Knock out Dulbecco's Modified Eagle's Medium (knock out-DMEM, Invitrogen, CA, USA) supplemented with 20% Knockout Serum Replacement (KSR; Invitrogen, USA), 0.1 mM MEM Non-Essential Amino Acids solution (Invitrogen, CA, USA), 0.2 mM L-glutamine (Invitrogen, USA), 0.1 mM β-mercaptoethanol (Invitrogen, CA, USA) and 1000 U/ml LIF (Millipore) 0.5% penicillin and streptomycin. The colonies thus generated were detached regularly at an interval of 3-4 days with 0.2% collagenase-1V (Invitrogen, CA, USA) dissociated into single cell suspension with 0.025% trypsin (Sigma Aldrich, MO, USA) and re-plated onto MEFs for propagation.

Cell Proliferation Assay

The cell proliferation assay was performed with the use of the MTS [3-(4,5-dimethylthiazol-2-yl)-5-(3-carboxymethoxyphenyl)-2-(4-sulfophenyl)-2H-tetrazolium] assay according to the manufacturer's recommendations (Promega). The plates were read at 490 nm using an automated ELISA plate-reader for the quantity of formazan product which was directly proportional to the number of living cells in culture.

DNA Methyltransferase (DNMT) Activity Assay

Nuclear extracts were isolated using the NE-PER Nuclear and Cytoplasmic Extraction Kit (Thermo Scientific, IL USA). Total DNMT activity was determined using an EpiQuik DNA methyltransferase activity assay kit (Epigentek, Brooklyn, N.Y.) per manufacturer's protocol. Enzyme activity for samples and controls was measured on a microplate reader (Hidex Chameleon, Finland) at 450 nm and DNMT activity (OD/h/ml) was calculated according to the formula: (Sample OD−blank OD)/(sample volume)×1000.

RT-PCR and Quantitative RT-PCR

Total RNA from small molecule treated and non-treated SiPS cells was isolated using RNeasy mini kit (Qiagen, Maryland, USA) and Omniscript Reverse Transcription kit (Qiagen, Maryland, USA) was used for the respective cDNA synthesis per manufacturer's instructions. For PCR amplification, 1 μg of the cDNA from the reverse transcription reaction was added to PCR mix containing the suggested quantity of the PCR buffer, Q solution, dNTP mix, reverse and forward primers, Taq DNA polymerase and distilled water. PCR conditions included initial denaturation at 95° C. for 4 minutes, 32 cycles of denaturation at 95° C. for 1 minute, annealing at 55° C. for 1 minute, extension at 72° C. for 1 minute and final extension at 72° C. for 7 minutes. The PCR products were separated on 1.5% agarose gel, stained with ethidium bromide and visualized and photographed on a UV transluminator (Bio-Rad, USA).

Myocardial Infarction Model

The animals were anesthetized with (ketamine/xylazine 0.05 ml intra-peritonealy). A midline cervical skin incision was performed for intubation. The animals were mechanically ventilated with room air supplemented with oxygen (1.5 L/min) using a rodent ventilator (Model 683, Harvard Apparatus, MA, USA). Body temperature was carefully monitored with a probe (Cole-Parmer Instrument, IL, USA) and was maintained at 37° C. throughout the surgical procedure. The heart was exposed by left-sided limited thoracotomy and the left anterior descending (LAD) coronary artery was ligated with a prolene #9-0 suture. Myocardial ischemia was confirmed by color change of the left ventricular wall. The animals were grouped (n=12 per group) for intramyocardial injection of 10 μL of basal DMEM without cells (group-1) or containing $3.6 \times 10^5$ SiPS (group-2) or $3.6 \times 10^{-5}$ SiPS-CPs (group-3). The cells were injected 10 minutes after coronary artery ligation at multiple sites (3-4 sites per heart) around the periphery of ischemic area of the free wall of the left ventricle under direct vision. For post-engraftment tracking of the transplanted cells and determination of their fate, the cells were labeled with PKH26 (Sigma, Product# PKH26-GL) according to manufacturer's instructions. The chest was closed and the animals were allowed to recover. To alleviate pain, Buprinex (0.05 ml) was injected subcutaneously in first 24 hours of surgery. The animals were euthanized on 7 days 4 weeks and 6-8 weeks after transthoracic echocardiography for the heart function evaluation. The hearts were frozen or fixed with 10% formalin solution and processed for embedding in paraffin for immunohistological studies.

Transthoracic Echocardiography

The animals (n=8 per group) were anesthetized and lightly secured in the supine position on a warm pad. After the chest was shaven, Acoustic gel was applied and transthoracic echocardiography was performed using HDI-5000 SONOS-CT (HP) ultrasound machine with a 7-MHz transducer. The heart was imaged in the two-dimensional mode in the parasternal long-axis and/or parasternal short-axis views which were subsequently used to position the M-mode cursor perpendicular to the ventricular septum and left ventricle posterior wall, after which M-mode images were obtained. For each animal, measurements were obtained from 4-5 consecutive heart cycles. Measurements of ventricular septal thickness (VST), left ventricle internal dimension (LVID), and left ventricle posterior wall thickness (LVPW) were made from two-dimensionally directed M-mode images of the left ventricle in both systole and diastole. The average value from all measurements in an animal were used to determine the indices of left ventricle contractile function, i.e., left ventricle fractional shortening (LVFS) and left ventricle ejection fraction (LVEF) using the following relations LVFS=(LVEDd2LVESd)/LVEDd6100 and LVEF=[(LVEDd32LVESd3)/LVEDd3]6100 and expressed as percentages.

Immunocytochemistry

For immunocytochemistry, differentiated colonies of SiPS were immunostained with respective specific primary antibodies (anti-Oct3/4, anti-Sox2, anti-Nanog antibodies, all at 1:100 concentration; Cell Signaling, Danvers, USA). Small molecule treated SIPs were seeded on 0.1% gelatin coated chambered slides for immunostaining. The cells were fixed with PBS containing 4% paraformaldehyde for 10 minutes at room temperature. After washing with PBS, the cells were blocked for 45 minutes at room temperature by CAS block (Invitrogen, CA, USA) and were immunostained with antigen specific primary antibodies Nkx-2.5, Gata 4,α Sarcomeric actin. (Santa Cruz, Calif., USA). The primary antibody-antigen reaction was detected with fluorescently conjugated specific secondary antibodies. Nuclei were stained with 5 µg/ml 4'6-diamidino-2-phenyl indole (DAPI; Invitrogen, CA, USA) staining. Fluorescence signals were observed and photographed using fluorescence microscopy (Olympus; Tokyo, Japan).

Gene Expression Profiling

Affymetrix array-based gene expression profiling further confirmed 2-3 folds downregulation of Dnmt1, Dnmt3b and Max gene associated protein which were associated with global DNA hypomethylation and myc dependent cell transformation. In addition, there was 2-3 folds concomitant upregulation of CCL7, CXCR2, CXCR5, integral membrane protein 2A, and EphrinA3.

| Fold change | | Regulation | Genes description | Genes symbol |
|---|---|---|---|---|
| IPS | IPs + Small Molecule | | | |
| 1.7296195 | 3.3164034 | up | chemokine (C-C motif) ligand 7 | Ccl7 |
| 1.4497509 | 2.7316089 | up | chemokine (C—X—C motif) ligand 2 | Cxcl2 |
| 1.0954261 | 2.136762 | up | chemokine (C—X—C motif) ligand 5 | Cxcl5 |
| 1.1732435 | 2.2551816 | up | integral membrane protein 2A | Itm2a |
| 1.1245799 | 2.1803806 | up | integral membrane protein 2B | Itm2b |
| 1.0622039 | 2.088119 | up | ephrin A3 | Efna3 |
| 1.5880175 | 3.0063593 | up | COX16 cytochrome c oxidase assembly homolog | Cox16 |
| 1.3481197 | 2.5458012 | up | cytochrome coxidase, subunit VIb polypeptide 1/Electron Transport Chain | Cox6b1 |
| 1.2005587 | 2.2982864 | up | ubiquinol-cytochrome c reductase, complex III subunit X | Uqcr10 |
| 3.056267 | −1.6117706 | down | DNA methyltransferase | Dnmt1 |
| 2.431835 | −1.2820454 | down | DNA methyltransferase 3B | Dnmt3b |
| 2.1499553 | −1.1043067 | down | MAX gene associated protein | Mga |

Experiment No. 2

Applicant has identified a bone marrow stem cell population named small juvenile stem cells (SJSCs) from aged mouse which express pluripotency and cardiac markers. Applicant expects when these cells are treated with isoxazole compound, would be more appropriate for cardiac differentiation and can be used as an alternate to IPS cells (Igura, K. et al. (2013) Am J Physiol Heart Circ Physiol. 305(9):H1354-H1362).

Experiment No. 3

This experiment discloses an alternate method of generating cardiac progenitors by preconditioning with electrical stimulation supplemented with cardiogenic small molecules. Applicant identified another cell population (Kim, S. W. et al. (2013) Cardiovasc Res. 100(2):241-251) that expresses hematopoietic progenitor marker (c-kit), pluripotency markers (Oct-4, Sox2, Nanog), a stem cell side population marker (Bcrp1), early cardiac lineage markers (Nkx-2.5, GATA4, MEF2C), and a vascular progenitor marker (Flk1). Preconditioning (PC) of stem cells either through a brief period of ischaemia/anoxia or treatment with alternative mimetic improves their post-engraftment survival and differentiation characteristics. However, there is no known report regarding the role of PC with electric stimulation (EleS) in stem cell survival, adhesion and cardiac differentiation. The heart generates a constant electrical field, the effect of which has not been explored in stem cells prior to transplantation. This study demonstrated that EleS provided PC effects on the survival of cardiac stem cells (Sca-1+ CSCs) through an increase in cell adhesion via focal adhesion kinase (FAK) activation, and releasing connective tissue growth factor (CTGF) by miR-378 down-regulation. It was found that connective tissue growth factor (Ctgf) was responsible for EleS-induced CSC($^{EleS}$CSCs) survival and adhesion. Importantly, knockdown of Ctgf abolished EleS-induced cytoprotective effects and recovery of cardiac function. Furthermore, miR-378 was identified as a potential Ctgf regulator in $^{EleS}$CSCs. This is another stem cell type which expresses both pluripotency and cardiac genes, and these cells can be further exploited with isoxazoles for cardiac progenitors.
Isolation of Sca-1$^+$ CSCs C57BL6 mice (Harlan) were used for isolation of CSCs. 12 weeks old C57BL6 mice were anesthetized by intraperitoneal injection of ketamine/xylazine (87-100 mg and 13-15 mg/kg, respectively). The depth of anesthesia was monitored by positive toe pinch and muscle relaxation. Hearts were extracted and washed with ice-cold PBS to remove blood cells. After removal of aorta, pulmonary artery, and pericardium, the whole hearts were minced and digested for 20 min at 37° C. with 0.1% type-II collagenase (Invitrogen) and 0.01% DNase I (Worthington Biochemical Corporation). The cells obtained were passed through 40 µm filter to remove the debris, fractionated with 70% Percoll (Fluka) and cultured in maintenance medium containing serum-free DMEM/F12 (Invitrogen) supplemented with B27 (Invitrogen), 20 ng/ml EGF (Sigma), and 40 ng/ml bFGF (basic fibroblast growth factor, Peprotech). One week later, the cells were transferred to new dishes with serum-free maintenance medium with a density of 100 cells/cm$^2$ to initiate colony formation and each colony was mechanically picked up for individual sub-culture in 24 well dishes in DMEM/F12 (Invitrogen) supplemented with 2% FBS, B27 supplement, 20 ng/ml EGF, 40 ng/ml bFGF, and 10 ng/ml LIF (Leukemia inhibitory factor, Millipore). Colony-derived cells were re-seeded on new dishes at 90% confluence and were maintained with DMEM/F12 with 2% FBS.
EleS of CSCs Twenty four hours after seeding at a cell density of $3\times10^5$ cells/35 mm dish, the cells were serum-starved for 15 hr followed by EleS ($^{EleS}$CSCs) using a culture cell pacer system (IonOptix). Cells were subjected to EleS for 0, 1, and 3 hr at 1.5 V/1.8 cm with biphasic square pulse (5 ms) at 5 Hz frequency. Cells without EleS ($^{Non-EleS}$CSC) were used as baseline controls. The cells were later harvested and used for various molecular and cellular studies.

Experiment No. 4

Isolation of Old Mesenchymal Stem Cells (OMSCs) and Young Mesenchymal Stem Cells (YMSCs) from Bone Marrow This study followed the Guide for the Care and Use of Laboratory Animals published by the US National Institutes of Health (NIH Publication #85-23, revised 1985) and protocol approved by the Institutional Animal Care and Use Committee, University of Cincinnati. BMSCs were isolated from bone marrow of C57BL/6 mice (young; 2 months, old; 24 months, respectively) as described previously in Igura K, et al. (2013) Am J Physiol. Heart Circ. Physiol 305:H1354-H1362. Briefly, BMSCs were cultured in 100 mm dishes with low glucose Dulbecco's modified Eagle's medium (DMEM) (HyClone Laboratories, Logan, Utah, hyclone.com) supplemented with 10% fetal bovine serum (FBS) for 6-10 days. The nonadherent hematopoietic bone marrow cells were discarded during the routine fresh medium replacement. YMSCs were isolated from old bone marrow by sieving through wells with 3-µm pores (cell culture insert; BD Bioscience, San Diego, Calif., bdbiosciences.com). The homogenicity of YMSC population was confirmed with surface marker expression by fluorescence activated cell sorting analysis as described previously in Igura, K. et al. (2013) Am J Physiol Heart Circ Physiol 305:H1354-H1362.

Quantitative Fluorescence In Situ Hybridization for Telomere Length Measurement

Telomere was detected by fluorescence in situ hybridization (FISH) with PNA Telomere Cy3-labeled probe (F1002; TelC-Cy3, PNA Bio) according to manufacturer's instructions. Briefly, cells were fixed with 4% paraformaldehyde for 1 hour. After washing with phosphate buffer solution (PBS), cells were incubated with RNase 100 ng/1 L for 20 minutes and 0.005% pepsin for 5 minutes at 37° C. After dehydration with 70%, 85%, and 100% of cold ethanol, cells were incubated with 200 nM PNA Telomere probe for 10 minutes at 85° C. and incubated for 2 hours at room temperature. Then, cells were incubated with 2 3 saline-sodium citrate (SSC) buffer for 10 minutes at 60° C. 4',6-diamidino-2-phenylindole (DAPI) and Cy3 signals were acquired simultaneously into separate channels using a confocal microscope (Fluoview FV1000, Olympus, Tokyo, olympus-global.com), and maximum projection from image stacks (10 sections at steps of 1 mm) were generated for image quantification. Telomere length was analyzed by using TFL-TeloV2-2 free software (Vancouver, Canada). With the program, the integrated fluorescence intensity value for each telomere, which is proportional to the number of hybridized probes, is calculated and presented. TFL-Telo is an application program used to estimate the length of telomeres from captured images of metaphases that have been stained for quantitative FISH (Q-FISH) analysis as described in Poon et al. (1999) Cytometry 36:267-278.
Reverse Transcription-Polymerase Chain Reaction Analysis Total RNA was isolated from various treatment groups of the cells with RNeasy Mini Kit (Qiagen, MD, qiagen.com), and cDNA was prepared using Omniscript-RT Kit (Qiagen), according to the manufacturer's instructions. For polymerase chain reaction (PCR) amplification, 1 µg of the cDNA from the reverse transcription reaction was then added to a PCR mix containing the suggested quantity of Qiagen PCR buffer, Q-Solution, dNTP mix, reverse and forward primers, Taq DNA polymerase, and distilled water. Each PCR reaction was performed with specific primers.
Isolation and Detection of miRNA Extraction of miRNAs was performed by using mirVana miRNA Isolation Kit, and miR-195 expression was detected by using mirVana qRT-PCR miRNA Detection Kit (Ambion, Life Technologies, Austin, Tex., ambion.com) and Quanti-Tect SYBR green PCR kit (Qiagen) as previously described in Kim et al. (2012) J. Mol. Med. 90:997-1010. Specific miRNA primers were purchased from Ambion.
miRNA Microarray Total RNA samples obtained from OMSCs and YMSCs were sent to Exiqon (Denmark, exiqon.com/) for miRNA microarray profiling. Data were analyzed by Exiqon with in-house developed computer programs. Intensity values were transformed into log 2 scale, and fold changes were given in log 2 scale. A t test was performed between OMSCs and YMSCs profiling, and statistically significant difference was considered at p <0.01.
FISH to Detect miR-195

In situ detection of miR-195 was performed in OMSCs and YMSCs plated on chamber slide. Samples were fixed in 4% para-formaldehyde for cell culture at room temperature for 20 minutes followed by two washes in PBS. Fixed cells were then prehybridized in hybridization solution (Bio-Chain, CA) for 3 hours at room temperature before hybridization. Probe (3 pmol; LNA-modified and fluorescein isothiocyanate (FITC)-labeled oligonucleotide; purchased from Exiqon) complementary to miR-195 was hybridized to the cells for 13-16 hours at 22° C. lower than predicted Tm of the probe. Subsequent to post hybridization washes with SSC buffer, in situ hybridization signals were detected with confocal microscope (Fluoview FV1000, Olympus).

Luciferase Activity Assay

Precursor miR-195 expression vector was constructed in a feline immunodeficiency virus-based lentiviral vector system (GeneCopoeia). Luciferase reporter constructs containing 3'-untranslational region (UTR) of mouse Tert was designed to encompass mmu-miR-195 binding sites. Cells were plated into 24-well plates in triplicate and cotransfected with miR-195 vector (or scramble vector) and reporter construct with Lipofectamine 2000 (Invitrogen, Carlsbad, Calif., invitrogen.com). Firefly luciferase activities were measured by using Dual Luciferase Reporter Assay System kit (Promega, Madison, Wis., promega.com) per manufacturer's instructions. Transfection efficiency was normalized by Renilla luciferase activity.

Lentivirus-Mediated miR-195 Inhibition in OMSCs

Lentivirus containing miR-195 inhibitor-expressing vector was generated by using Lenti-Pac HIV Expression Packaging System (GeneCopoeia) per manufacturer's protocol. Briefly, 2.5 µl of lentiviral miR-195 inhibitor expression plasmid or scramble, 5.0 mL of EndoFectin Lenti and EndoFectin Lenti reagent were added in Opti-MEM I, and formed the DNA-EndoFectine complex. After incubating the complex at room temperature for 10-25 minutes, the DNA-EndoFectine complex was added to 293Ta cells in DMEM with 10% FBS, and then, incubated in 5% CO2 at 37° C. overnight. The culture medium was replaced with fresh DMEM with 5% FBS and 1/500 volume of the TiterBoost reagent to the culture medium. The virus pseudovirus-containing culture medium was collected at 48 hours post-transfection and concentrated after filtration. For the transduction of OMSCs with lentivirus, $10 \times 10^6$ of OMSCs was plated, and 20 µl of virus suspension was added. To enhance lentiviral transduction efficiency, cells were placed at 4° C. for 2 hours and then incubated in a 5% CO2 at 37° C. for 48 hours/Senescence-Associated β-Galactosidase (gal) Staining Senescence-associated β-gal was detected by Senescence Detection Kit (BioVision, CA, biovision.com/) per manufacturer's instruction.

Terminal Deoxynucleotidyl Transferase dUTP Nick End Labeling Assay

Apoptotic cell death was detected by terminal deoxynucleotidyl transferase dUTP nick end labeling (TUNEL) according to instructions of the manufacturer (TMR Red; Roche Applied Science, roche-applied-science.com). For quantification, the numbers of TUNEL positive cells were counted in at least five randomly selected high-power fields (magnification 3 200) with three independent samples.

Western Blot Analysis

Western blot was carried out as previously described in Kim et al. (2009) Cardiovasc Res. 100:241-251. Briefly, cells were lysed in lysis buffer, pH 7.4 [(in mM) 50 HEPES, 5 EDTA, 50 NaCl], 1% Triton X-100, protease inhibitors [(10 mg/mL aprotinin, 1 mM phenylmethylsulfonyl fluoride, 10 mg/mL leupep-tin) and phosphatase inhibitors [(in mM) 50 sodium fluoride, 1 sodium orthovanadate, 10 sodium pyrophosphate]. The protein samples (40 mg) were electrophoresed using SDS-polyacrylamide gel and electroimmunoblotted. The specific antibodies used for the detection of Tert (sc-68720) was purchased from Santa Cruz (Santa Cruz, Calif., scbt.com), p53 (#2524), Sirt-1 (#2028), Phospho-FoxO1 (#2599), Bcl-2 (#3498), cleaved caspase-3 (#9661), Akt (#2920), Phospho Akt (#4060), and Actin (#4968) were purchased from Cell Signaling (Beverly, Mass., cellsignal-.com). All antibodies were used as diluted with 1:1,000.

Determination of Cell Proliferation Rate

Cell proliferation rate was determined by cell growth assay and colony formation assay as previously reported in Igura, K. et al. (2013) Heart Circ. Physiol. 305:H1354-1362.

Experimental Model of Acute Myocardial Infarction and Cell Transplantation

In vivo cell transplantation using mouse acute myocardial infarction (AMI) model was performed in accordance with Applicant's previous report in Kim et al. (2013) Cardiovasc. Res. 100:241-251. Briefly, C57BL/6 mice (male 24 months old, 30-35 g b. wt.; n 5 10 animals per group) were prepared for left anterior descending (LAD) coronary artery ligation. Intraperitoneal anesthesia was administered with 0.1% of ketamine and 0.02% of xylene per body weight (g) for anesthesia. After endotracheal intubation and mechanical ventilation using Rodent Ventilator (Harvard Apparatus Model 683), the heart was exposed by left-sided minimal thoracotomy and LAD coronary artery was ligated with 6-0 silk. Immediately after ligation, 20 µl DMEM without cells or containing $2 \times 10^5$ cells (scrOMSCs or anti-195OMSCs) were injected into infarction and border zones. Following injection, the opened chests of mice were sutured and all mice were allowed to recover.

miR-195 Expression is Markedly Upregulated in OMSCs

To profile miRNA expression induced with aging, Applicant isolated total RNA from OMSCs and YMSCs, and performed microarray analysis in OMSCs and YMSCs). Per these results, the expression of miR-140, miR-146a/b, and miR-195 was significantly upregulated in OMSCs whereas expression of miR-29b, miR-205, miR-378, and miR-542-3p was down regulated in OMSCs. Reverse transcriptase PCR (RT-PCR) and real time PCR confirmed microarray result that miR-195 expression was significantly upregulated in OMSCs as compared to YMSCs. FISH analysis for miR-195 visualization further confirmed that miR-195 was highly expressed in OMSCs. This result led Applicant to hypothesize that miR-195 was induced with aging, and its abrogation in OMSCs may restore the regenerative capacity of OMSCs. Applicant transfected OMSCs with anti-miR-195 and confirmed that transfected OMSCs showed reduced expression of miR-195 while scramble did not affect it, as shown by real-time RT-PCR, indicating that miR-195 inhibitor Applicant used was specific for reduction of miR-195 expression in stem cells.

Tert is a Direct Target of miR-195 in Aging Stem Cells

To investigate the biological relevance of miR-195 induction during stem cell aging and its participation in OMSCs senescence, Applicant first carried out target prediction analysis by in silico search to find potential target genes of miR-195 responsible for aging and senescence.

Interestingly, computational analysis predicted that mmu-miR-195 directly binds to 3'-UTR of mouse Tert gene. To experimentally validate this result, Applicant performed RT-PCR and Western blot analysis to examine whether Tert expression is altered by miR-195 knockdown in OMSCs. Interestingly, expression of both mRNA and protein of Tert was significantly increased by miR-195 abrogation in OMSCs (FIGS. 12B and 12C), indicating that Tert is a putative target of miR-195. Tert as a target gene of miR-195 was confirmed by luciferase activity assay which showed that cotransfection of a miR-195 expression vector (pEZX-miR-195) with the vector containing 3'-UTR of Tert gene significantly reduced luciferase activity in comparison to cotransfection with miR-scramble vector (pEZX-miR-Sc) (FIG. 12D). These results demonstrated that Tert is a direct target of miR-195 in stem cell aging.

Abrogation of miR-195 Rejuvenates OMSCs Through Telomere Relengthening and Antiaging Markers Reactivation To examine the mechanistic participation of miR-195 in stem cell aging, Applicant knocked down miR-195 expression by using a lentiviral miR-195 inhibitor vector (Lenti-anti-miR-195) which could successfully transfect OMSCs to achieve abrogation of miR-195 (FIG. 4). mCherry signal (red fluorescence) in this vector system allowed Applicant to recognize the transfected OSMCs with miR-195 inhibitor or scramble vector (FIG. 13B, upper panel). Interestingly, abrogation of miR-195 significantly reduced senescence-associated β-gal expression in OSMCs as compared to scramble transfected OMSCs (FIG. 13B, 20.6% 64.9% vs. 54.5% 68.1%, p<0.01). More importantly, OMSCs transfected with miR-195 inhibitor induced significant telomere relengthening (2.9-fold higher as compared to scramble transfection, FIG. 13C). Furthermore, inhibition of miR-195 reduced TUNEL-positive apoptotic cell death in OMSCs (FIG. 13D, 19.7% 64.5% vs. 60.8% 62.7%, p<0.01), suggesting that rejuvenated OMSCs by miR-195 abrogation survive better under apoptotic condition such as ischemia. Furthermore, expression of antiaging makers (Tert and Sirt-1) and prosurvival markers (p-Akt and Bcl-2) were significantly increased by transfection of anti-miR-195 in OMSCs whereas expression of senescence-associated markers (p53) and proapoptotic marker (cleaved caspase-3) was markedly reduced by miR-195 abrogation (FIG. 13E), supporting Applicant's hypothesis that inhibition of age-induced miR-195 can rejuvenate OMSCs by reactivation of antiaging factors and suppression of senescence-associated markers. It is important to note that knockdown of miR-195 significantly restored the impaired cell proliferative abilities in OMSCs as evaluated by cell proliferation assay and colony formation assay (FIGS. 13F and 13G). These results demonstrated that miR-195 induced during stem cell aging plays critical roles in their fate and behaviors.

Experiment No. 5

Generation of Cardiac Progenitor Cells from Human iPS Cells (hiPSCs) and Generation of Cells of Multiple Cell Lineages Therefrom Cells of Human iPSC line (ACS-1021™) from American Type Culture Collection, Manassas, Va., 20110 USA (ATCC) were maintained on a vitronectin coated six-well plate in mTeSR1 medium and dissociated into single cells using accutase (Invitrogen) at 37° C. for 10 min. Afterwards, the cells were seeded on to a vitronectin-coated six-well plate at 1×106 cell/well in mTeSR1 supplemented with 5 µM ROCK inhibitor (Y-27632, StemCell Technologies, Vancouver, British Columbia, Canada) (day-3) for 24 hours. Further, the pluripotency of those iPS cells were confirmed by immunostaining, for example, to confirm the marker expression for OCT4, SOX2, TRA-1-60, TRA-1-81 and SSEA4 (FIGS. 14A-14B).

The cells then were then cultured in mTesR1 medium, which was changed daily according to an exemplary schematic outline as shown in FIG. 14C. At day 0, the medium was changed to RPMFB27 medium minus insulin supplemented with 20 µM ISX-9 (StemCell Technologies) for 7 days. At the end of day 7 treatment, the expression of CPC markers including Nkx2.5 and GATA4 were observed by RT-PCR and Immunostaining (FIG. 14D).

For cardio myocyte differentiation, after 7 days ISX-9 treatment, the medium was switched to RPMI/B27 medium with insulin for another 7-10 days. At the end of 20 days, all the cells began spontaneous beating as shown in FIG. 14E.

For endothelial cells differentiation, 2×105/cm2 ISX-9 induced CPC were cultured in EGM-2 medium (Lonza, Lonza Walkersville Inc., Walkersville Md. 21793-0127) for 10 days. At the end of treatment, the endothelia cell makers, CD31 and VE-cadherin were expressed (FIG. 14F). To analyze tube formation on matrigel in vitro, cells were seeded on top of a thin layer of matrigel at a density of 1.2×105 cells/well of a 24-well plate. After 16 hours, cells were labeled with calcein AM (Corning, Tewksbury Mass. 01876, USA) and were examined under the fluorescent microscope to visualize formation of tube-like structures (FIG. 14G).

For smooth muscle cells differentiation, induced CPC were cultured in DMEM-F12 medium supplemented with TGFβ (2 ng/ml) and PDGFBB (long/ml, R&D Systems, Inc, Minneapolis, Minn. 55413) for 10 days. At the end of this period, a-SMA and calponin expression were observed by immunostaining (FIG. 14H).

Experiment No. 6

One Step Generation of Cardiac Progenitors from Monolayer Human Induced Pluripotent Stem Cells Using Isoxazole or Isoxazole Like Compounds Currently in order to generate cardiac progenitors (CPC) from induced pluripotent stem cells (iPSC) in large numbers to repair heart after sudden heart attack or chronically weakened heart due to congestive heart failure, iPSC have to be converted into embryoid bodies or treated with multiple small molecules. These steps are costly and time consuming. Despite of these developments the progress is slow and at the same time, the purity of CPC preparations is not guaranteed. The one step use of isoxazole or isoxazole compounds such as ISX-9 has been extremely efficient in generating CPCs without the use of other growth factors (activin, BMP4), glycogen synthase kinase 3 inhibitor, Wnt inhibitor as well other small molecules. This small molecule has been previously reported for neuronal cell differentiation (Schneider et al. (2008) Nat Chem Biol. 4(7):408-10. doi: 10.1038/nchembio.95) and for reprogramming of fibroblasts into neurons in combination with other small molecules (Li et al. (2015) Cell Stem Cell 17(2):195-203).

Figure 1:
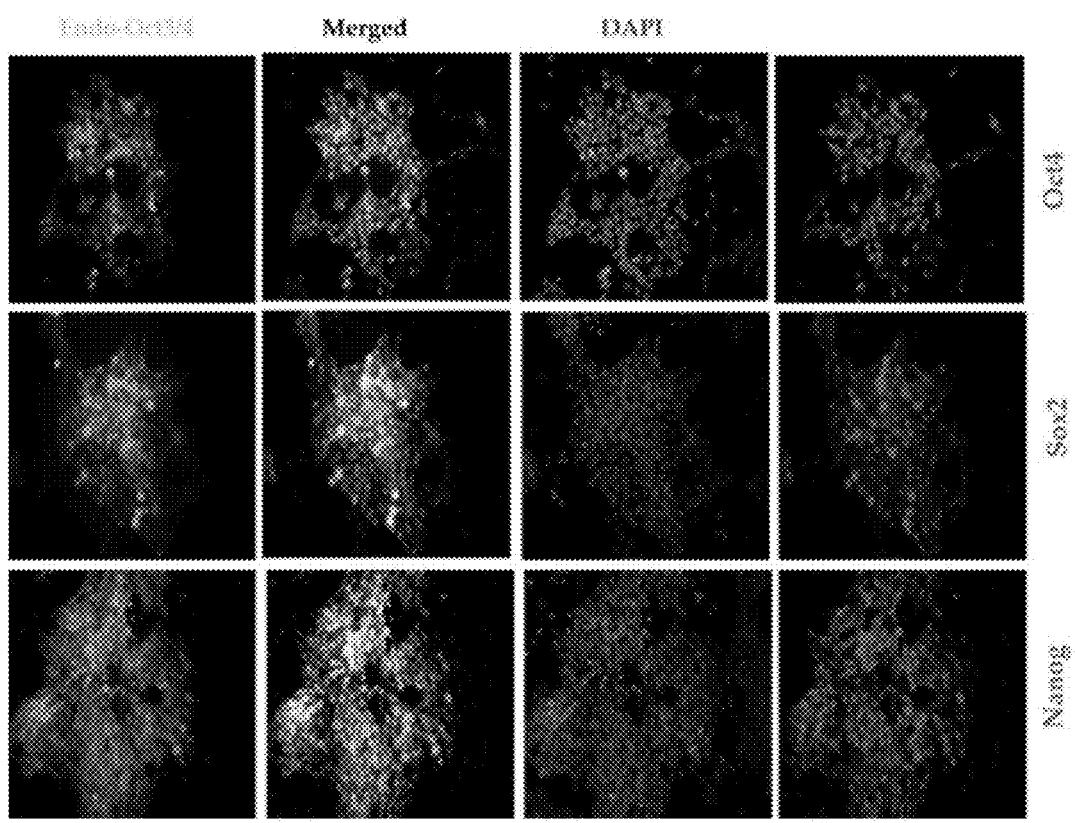
FIG. 1 shows characterization of IPS cells for the expression of pluripotency markers. Representative photomicrographs showing IPS clones expressing embryonic stem cells (ESC) specific markers Oct3/4, Sox2, Nanog and endogenous Oct4. Nuclei were stained with DAPI.

To test this rationale, Applicant also purchased human iPSC line (ACS-1021™) from American Type Culture Collection, Manassas, Va., 20110 USA (ATCC). iPSC maintained on vitronectin coated six-well plate in mTeSR1 medium were dissociated into single cells using accutase (Invitrogen) at 37° C. for 10 min and then were seeded on to a vitronectin-coated six-well plate at 1×10$^6$ cell/well in mTeSR1 supplemented with 5 µM ROCK inhibitor (Y-27632, StemCell Technologies, Vancouver, British Columbia, Canada) (day-3) for 24 h (FIG. 14A). iPSC were confirmed for their pluripotency by Immunostaining (FIG. 14A,B). Cells then were cultured in mTesR1 medium, which was changed daily according to our schematic outline (FIG. 14C). At day 0, the medium was changed to RPMI/B27 medium minus insulin supplemented with 20 µM ISX-9 (StemCell Technologies) for 7 days. At the end of day 7 treatment, the expression of CPC markers including Nkx2.5 and GATA4 were observed by RT-PCR and Immunostaining (FIG. 14D). For cardiomyocyte differentiation, after 7 days ISX-9 treatment, the medium was switched to RPMFB27 medium with insulin for another 7-10 days. At the end of 20 days, all cells began spontaneous beating (FIG. 14E). For endothelial cells differentiation, 2×10$^5$/cm$^2$ ISX-9 induced CPC were cultured in EGM-2 medium (Lonza, Lonza Walkersville Inc., Walkersville Md. 21793-0127) for 10 days. At the end of treatment, the endothelia cell makers, CD31 and VE-cadherin were expressed (FIG. 14F). To analyze tube formation on matrigel in vitro, cells were seeded on top of a thin layer of matrigel at a density of $1.2 \times 10^5$ cells/well of a 24-well plate. After 16 hr, cells were labeled with calcein AM (Corning, Tewksbury Mass. 01876, USA) and were examined under the fluorescent microscope to visualize formation of tube-like structures (FIG. 14G). For smooth muscle cells differentiation, induced CPC were cultured in DMEM-F12 medium supplemented with TGFβ (2 ng/ml) and PDGFBB (long/ml, R&D Systems, Inc, Minneapolis, Minn. 55413) for 10 days. At the end of this period, α-SMA and calponin expression were observed by immunostaining (FIG. 14I1).

In conclusion, Isx-9 was very effective small molecule for converting iPSC consistently into cardiac progenitors including endothelial/vascular progenitors and smooth muscle cells.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Shi Y, Do J T, Desponts C, Hahm H S, Schöler H R, Ding S (2008). A combined chemical and genetic approach for the generation of induced pluripotent stem cells. Cell Stem Cell. June 5; 2(6):525-8.
2. Huangfu D, Maehr R, Guo W, Eijkelenboom A, Snitow M, Chen A E, Melton D A (2008). Induction of pluripotent stem cells by defined factors is greatly improved by small-molecule compounds. Nat Biotechnol. July; 26(7): 795-7.
3. Zhu S, Li W, Zhou H, Wei W, Ambasudhan R, Lin T, Kim J, Zhang K, Ding S (2010). Reprogramming of human primary somatic cells by OCT4 and chemical compounds. Cell Stem Cell, vol. 7, no. 6, pp. 651-655.
4. C. Desponts and S. Ding (2010). Using small molecules to improve generation of induced pluripotent stem cells from somatic cells. Methods in Molecular Biology, vol. 636, pp. 207-218.
5. Pasha Z, Haider H K h, Ashraf M (2011). Efficient non-viral reprogramming of myoblasts to stemness with a single small molecule to generate cardiac progenitor cells. PLoS One.; 6(8):e23667.
6. Sadek H, Hannack B, Choe E, Wang J, Latif S, Garry M G, Garry D J, Longgood J, Frantz D E, Olson E N, Hsieh J, Schneider J W (2008). Cardiogenic small molecules that enhance myocardial repair by stem cells. Proc Natl Acad Sci USA. April 22; 105(16):6063-8.
7. Russell J L, Goetsch S C, Aguilar H R, Frantz D E, Schneider J W. Targeting native adult heart progenitors with cardiogenic small molecules. ACS Chem Biol. 2012 Jun. 15; 7(6):1067-76.
8. Igura K, Okada M, Kim H W, Ashraf M. Identification of small juvenile stem cells in aged bone marrow and their therapeutic potential for repair of the ischemic heart. Am J Physiol Heart Circ Physiol. 2013 Nov. 1; 305(9):H1354-62.
9. Kim S W, Kim H W, Huang W, Okada M, Welge J A, Wang Y, Ashraf M. Cardiac stem cells with electrical stimulation improve ischaemic heart function through regulation of connective tissue growth factor and miR-378. Cardiovasc Res. 2013 Nov. 1; 100(2):241-51.
10. Jay W Schneider, Zhengliang Gao, Shijie Li, Midhat Farooqi, Tie-Shan Tang, Ilya Bezprozvanny, Doug E Frantz & Jenny Hsieh. Small-molecule activation of neuronal cell fate. Nat Chem Biol. 2008 July; 4(7):408-10. doi: 10.1038/nchembio.95. Epub 2008 Jun. 15.
11. Li X et al. (2015) Small-molecule-driven direct reprogramming of mouse fibroblasts into functional neurons. Cell Stem Cell 17(2): 195-203.
12. Dioum, E. M., Osborne, J. K., Goetsch, S., Russell, J., Schneider, J. W., and Cobb, M. H. (2011) A small molecule differentiation inducer increases insulin production by pancreatic beta cells. Proc. Natl. Acad. Sci. U.S.A. 108, 20713-20718.

What is claimed is:

1. A method of repairing cardiac tissue, said method comprising:
   a) culturing human parent cells in a medium without insulin and with isoxazole or isoxazole-9 in an amount effective to induce differentiation into cardiac progenitor cells for 3-7 days and then culturing in said medium with insulin and without said isoxazole or isoxazole-9 for 7-10 days, wherein said human parent cells are induced pluripotent stem cells (iPSCs) or pluripotent stem cells (PSCs);
   b) injecting said cardiac progenitor cells or progeny thereof into damaged cardiac tissue of a heart of a human patient with in an amount sufficient for cardiac tissue repair.

2. The method of claim 1, further comprising culturing said cardiac progenitor cells to expand the cardiac progenitor cells before said injecting in step b).

3. The method of claim 1, further comprising culturing said cardiac progenitor cells with i) insulin, or ii) TGFB1 and PDGFBB, or iii) EGM to induce further differentiation into i) cardiomyocytes, ii) smooth muscle cells, or iii) endothelial cells before said injecting in step b).

4. The method of claim 1, wherein said human parent cells are from said patient or are allogenic to said patient.

5. The method of claim 1, wherein said human parent cells are iPSCs made by treating human adult somatic cells with a DNA methyltransferase inhibitor in an amount sufficient to elevate OCT4, as compared with untreated human adult somatic cells.

6. The method of claim 1, wherein said human parent cells are iPSCs made by treating human adult somatic cells from skeletal muscle with a DNA methyltransferase inhibitor in an amount sufficient to elevate OCT4, as compared with untreated human adult somatic cells.

7. The method of claim 1, wherein said method excludes insertion of an exogenous gene(s) into said human parent cells.

8. The method of claim 1, wherein said cardiac progenitor cells are characterized by:
   i) over-expression of Nkx-2.5; and
   ii) decreased of one or more pluripotency genes selected from a miR-290-295 cluster, let-7 family, or max; and
   iii) underexpression of Dnmt1 and Dnmt3b;
   as compared with untreated human parent cells.

9. The method of claim 1, wherein step c) uses 0.1-30 µM of isoxazole or isoxazole-9.

10. The method of claim 1, further comprising conditioning said PSCs or iPSCs with a period of ischaemia before said injecting in step b).

11. The method of claim 1, wherein said injecting in step b) is direct injection into a site of damage of said heart.

12. A method of cardiac tissue repair in a human patient in need thereof, said method comprising:
   a) obtaining human induced pluripotent stem cells (iPSCs) or pluripotent stem cells (PSCs);
   b) culturing said iPSCs or PSCs in a medium without insulin and with isoxazole or isoxazole-9 in an amount effective to induce differentiation for 3-7 days and then culturing in said medium with insulin and without said isoxazole or isoxazole-9 for 7-10 days to make cardiac progenitor cells or cardiomyocytes;
   c) wherein said cardiac progenitor cells or cardiomyocytes are characterized by:
      i) overexpression of Nkx-2.5 and one or more cardiac markers selected from ISL1, GATA4, ΔMHC, sarcomeric actin, Gαi, mir-133, mir-762, CCL7, CXCR2, CXC5, integral membrane protein 2A, and ephrin A3, and
      ii) underexpression of one or more pluripotency markers selected from a miR-290-295 cluster, let-7 family, Dnmt1, Dnmt3b, and Max, and
      iii) underexpression of one or more DNA methyltransferase genes,
   each as compared with untreated iPSCs or PSCs;
   d) injecting said cardiac progenitor cells or said cardiomyocytes into damaged cardiac tissue of a heart of a human patient in an amount sufficient for cardiac tissue repair.

* * * * *

SEQUENCE LISTING

<160> NUMBER OF SEQ ID NOS: 2

<210> SEQ ID NO 1
<211> LENGTH: 21
<212> TYPE: RNA

```
<213> ORGANISM: Mus musculus

<400> SEQUENCE: 1
uagcagcaca gaaauauugg c                                              21

<210> SEQ ID NO 2
<211> LENGTH: 22
<212> TYPE: RNA
<213> ORGANISM: Mus musculus

<400> SEQUENCE: 2
agcuaugguc uugcagcugc uc                                             22
```